(12) United States Patent
Dunsmore et al.

(10) Patent No.: US 8,534,284 B2
(45) Date of Patent: *Sep. 17, 2013

(54) RESPIRATORY THERAPY DEVICE

(75) Inventors: Thomas J. Dunsmore, Glendora, CA (US); Geoffrey C. Wise, Benicia, CA (US); Thomas C. Wilschke, Riverside, CA (US); Christopher J. Matice, Bellbrook, OH (US); Christopher L. Gillum, Middletown, OH (US); Shannon Rice Read, Lebanon, OH (US)

(73) Assignee: CareFusion 2200, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/246,320

(22) Filed: Sep. 27, 2011

(65) Prior Publication Data

US 2012/0012112 A1 Jan. 19, 2012

Related U.S. Application Data

(63) Continuation of application No. 11/670,867, filed on Feb. 2, 2007, now Pat. No. 8,025,054, which is a continuation of application No. 11/559,288, filed on Nov. 13, 2006, now Pat. No. 7,779,841.

(51) Int. Cl.
*A62B 9/02* (2006.01)

(52) U.S. Cl.
USPC ............ 128/205.24; 128/200.24; 128/204.18; 128/200.14

(58) Field of Classification Search
USPC ............ 128/205.24, 203.12, 203.19, 200.23, 128/200.24, 200.14, 200.16–18, 203.13–14, 128/203.16, 203.23, 203.11, 203.15, 204.18, 128/204.19, 204.21, 205.23, 207.16, 207.18; 222/334, 389, 386.5, 387; 239/338, 569, 239/570

See application file for complete search history.

(56) References Cited

U.S. PATENT DOCUMENTS

| | | |
|---|---|---|
| 3,191,596 A | 6/1965 | Bird et al. |
| 3,301,255 A | 1/1967 | Thompson |

(Continued)

FOREIGN PATENT DOCUMENTS

| | | |
|---|---|---|
| RU | 2004260 C1 | 12/1993 |
| SU | 1703135 A1 | 1/1992 |

OTHER PUBLICATIONS

Dean R. Hess, PhD, article entitled "The Evidence for Secretion Clearance Techniques;" Respiratory Care, Nov. 2001, vol. 46, No. 11, pp. 1276-1293.

(Continued)

*Primary Examiner* — Justine Yu
*Assistant Examiner* — Colin W Stuart
(74) *Attorney, Agent, or Firm* — McDermott Will & Emery LLP

(57) ABSTRACT

A respiratory therapy device including a housing and an interrupter valve assembly. The housing is sized for handling by a patient and defines a patient breathing passage extending from a patient end and through which a patient inhales and exhales air. The interrupter valve assembly is carried by the housing and includes a control port, a valve body, and a drive mechanism. Expiratory airflow is released from the patient breathing passage through the control port. The valve body is sized to at least partially obstruct fluid flow through the control port. The drive mechanism moves the valve body relative to the control port in response to the expiratory airflow such that the valve body repeatedly transitions between a position of maximum obstruction and a position of minimum obstruction relative to the control port to create an oscillatory positive expiratory pressure effect.

13 Claims, 36 Drawing Sheets

(56) References Cited

U.S. PATENT DOCUMENTS

| | | |
|---|---|---|
| 3,580,249 A | 5/1971 | Takaoka |
| 3,581,742 A | 6/1971 | Glenn |
| 3,584,621 A | 6/1971 | Bird et al. |
| 3,610,237 A | 10/1971 | Barkalow |
| 3,630,196 A | 12/1971 | Bird |
| 3,664,337 A | 5/1972 | Lindsey et al. |
| 3,769,973 A | 11/1973 | Esbenshade, Jr. |
| 3,881,480 A | 5/1975 | Lafourcade |
| 3,903,884 A | 9/1975 | Huston et al. |
| 3,974,828 A | 8/1976 | Bird |
| 3,984,133 A | 10/1976 | Bird |
| 4,020,834 A | 5/1977 | Bird |
| 4,037,994 A | 7/1977 | Bird |
| 4,039,139 A | 8/1977 | Bird |
| 4,044,763 A | 8/1977 | Bird |
| 4,054,134 A | 10/1977 | Kritzer |
| 4,060,078 A | 11/1977 | Bird |
| 4,080,103 A | 3/1978 | Bird |
| 4,121,579 A | 10/1978 | Bird |
| 4,127,123 A | 11/1978 | Bird |
| 4,148,312 A | 4/1979 | Bird |
| 4,148,313 A | 4/1979 | Bird et al. |
| 4,164,219 A | 8/1979 | Bird |
| 4,197,843 A | 4/1980 | Bird |
| 4,231,973 A | 11/1980 | Young et al. |
| 4,351,329 A | 9/1982 | Ellestad et al. |
| 4,592,349 A | 6/1986 | Bird |
| 4,739,987 A | 4/1988 | Nicholson |
| 4,742,823 A | 5/1988 | Bird |
| 4,805,612 A | 2/1989 | Jensen |
| 4,805,613 A | 2/1989 | Bird |
| 4,823,828 A | 4/1989 | McGinnis |
| 4,838,260 A | 6/1989 | Bird |
| 4,867,151 A | 9/1989 | Bird |
| 4,930,501 A | 6/1990 | Bird |
| 5,007,420 A | 4/1991 | Bird |
| 5,018,517 A | 5/1991 | Liardet |
| 5,107,831 A | 4/1992 | Halpern et al. |
| 5,116,088 A | 5/1992 | Bird |
| 5,165,398 A | 11/1992 | Bird |
| 5,253,641 A | 10/1993 | Choate |
| 5,345,930 A | 9/1994 | Cardinal et al. |
| 5,381,789 A | 1/1995 | Marquardt |
| 5,451,190 A | 9/1995 | Liardet |
| 5,479,920 A | 1/1996 | Piper et al. |
| 5,570,682 A | 11/1996 | Johnson |
| 5,598,839 A | 2/1997 | Niles et al. |
| 5,613,489 A | 3/1997 | Miller et al. |
| 5,655,520 A | 8/1997 | Howe et al. |
| 5,658,221 A | 8/1997 | Hougen |
| 5,791,339 A | 8/1998 | Winter |
| 5,862,802 A | 1/1999 | Bird |
| 5,890,998 A | 4/1999 | Hougen |
| 5,899,832 A | 5/1999 | Hougen |
| 5,910,071 A | 6/1999 | Hougen |
| 6,083,141 A | 7/2000 | Hougen |
| 6,102,038 A | 8/2000 | DeVries |
| 6,253,766 B1 | 7/2001 | Niles et al. |
| 6,340,025 B1 | 1/2002 | Van Brunt |
| 6,500,095 B1 | 12/2002 | Hougen |
| 6,557,549 B2 | 5/2003 | Schmidt et al. |
| 6,581,596 B1 | 6/2003 | Truitt et al. |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand et al. |
| 6,615,831 B1 | 9/2003 | Tuitt et al. |
| 6,631,721 B1 | 10/2003 | Salter et al. |
| 6,659,100 B2 | 12/2003 | O'Rourke |
| 6,708,690 B1 | 3/2004 | Hete et al. |
| 6,726,598 B1 | 4/2004 | Jarvis et al. |
| 6,776,159 B2 | 8/2004 | Pelerossi et al. |
| 6,848,443 B2 | 2/2005 | Schmidt et al. |
| 6,851,598 B2 | 2/2005 | Gebauer et al. |
| 6,904,906 B2 | 6/2005 | Salter et al. |
| 6,929,007 B2 | 8/2005 | Emerson |
| 7,059,324 B2 | 6/2006 | Pelerossi et al. |
| 7,779,841 B2 | 8/2010 | Dunsmore et al. |
| 2001/0003984 A1 * | 6/2001 | Bennarsten et al. ..... 128/204.21 |
| 2003/0000531 A1 | 1/2003 | Tuck |
| 2003/0005931 A1 | 1/2003 | D. Jaffre et al. |
| 2003/0051729 A1 | 3/2003 | Be'eri et al. |
| 2003/0127092 A1 | 7/2003 | Pelerossi et al. |
| 2003/0192545 A1 | 10/2003 | Truitt et al. |
| 2003/0209247 A1 | 11/2003 | O'Rourke |
| 2003/0234017 A1 | 12/2003 | Pelerossi et al. |
| 2004/0035422 A1 | 2/2004 | Truitt et al. |
| 2005/0051168 A1 | 3/2005 | DeVries et al. |
| 2005/0061318 A1 | 3/2005 | Faram |
| 2006/0090753 A1 | 5/2006 | Pelerossi et al. |
| 2006/0107956 A1 | 5/2006 | Hendricksen et al. |
| 2008/0078383 A1 | 4/2008 | Richards et al. |

OTHER PUBLICATIONS

James B. Fink, article entitled "Positive Pressure Techniques for Airway Clearance;" Respiratory Care, Jul. 2002, vol. 47, No. 7, pp. 786-796.

James B. Fink, article entitled "High-Frequency Oscillation of the Airway and Chest Wall;" Respiratory Care, Jul. 2002, vol. 47, No. 7, pp. 797-807.

PCT Search Report, mailed Apr. 24, 2008; 4 pgs.

* cited by examiner

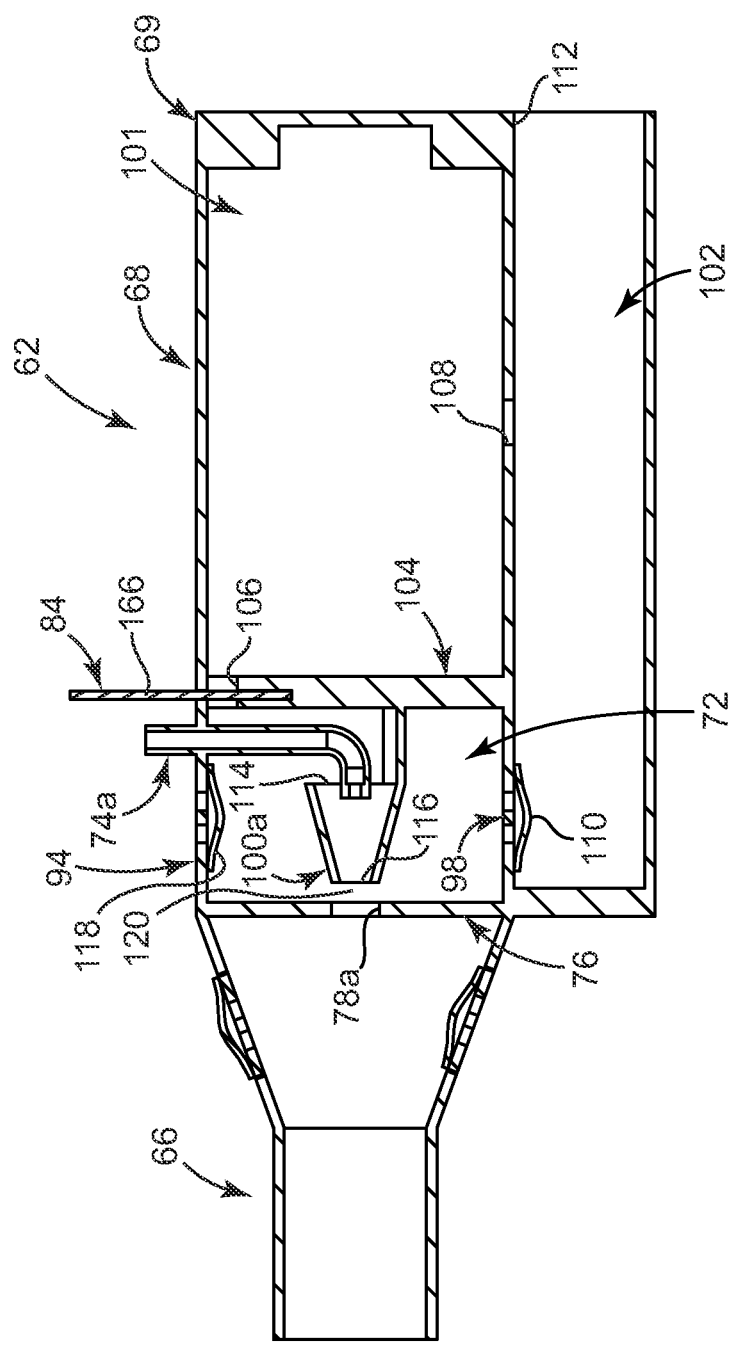

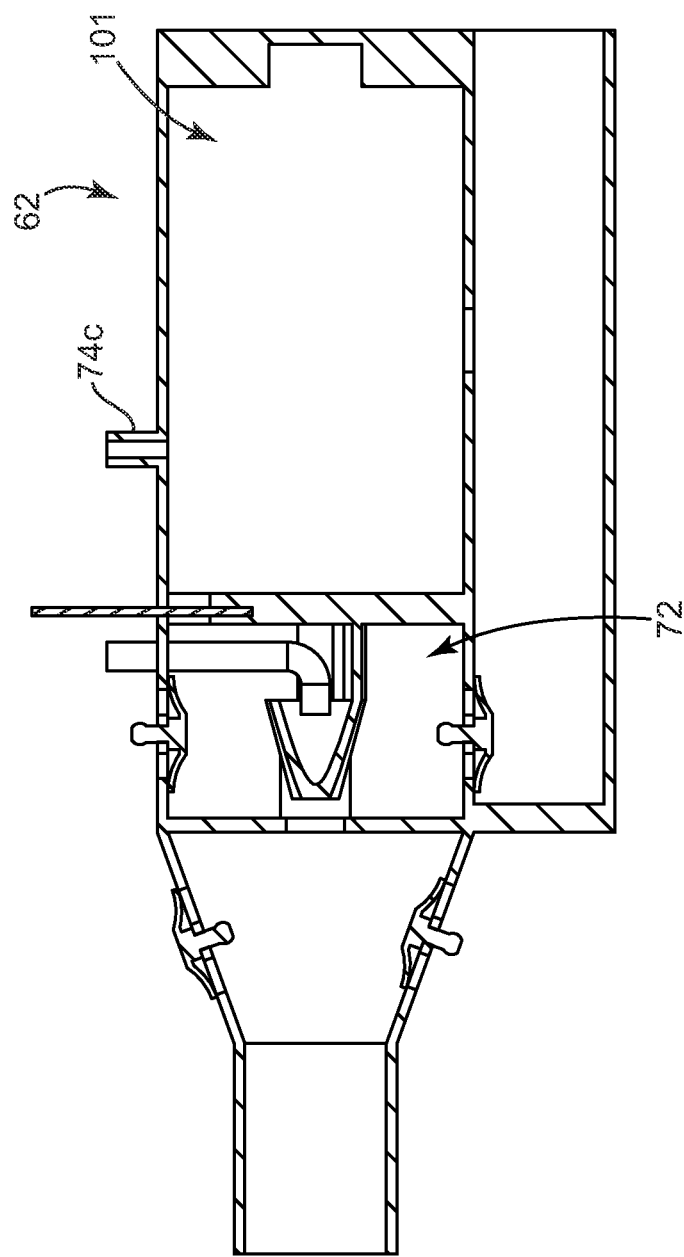

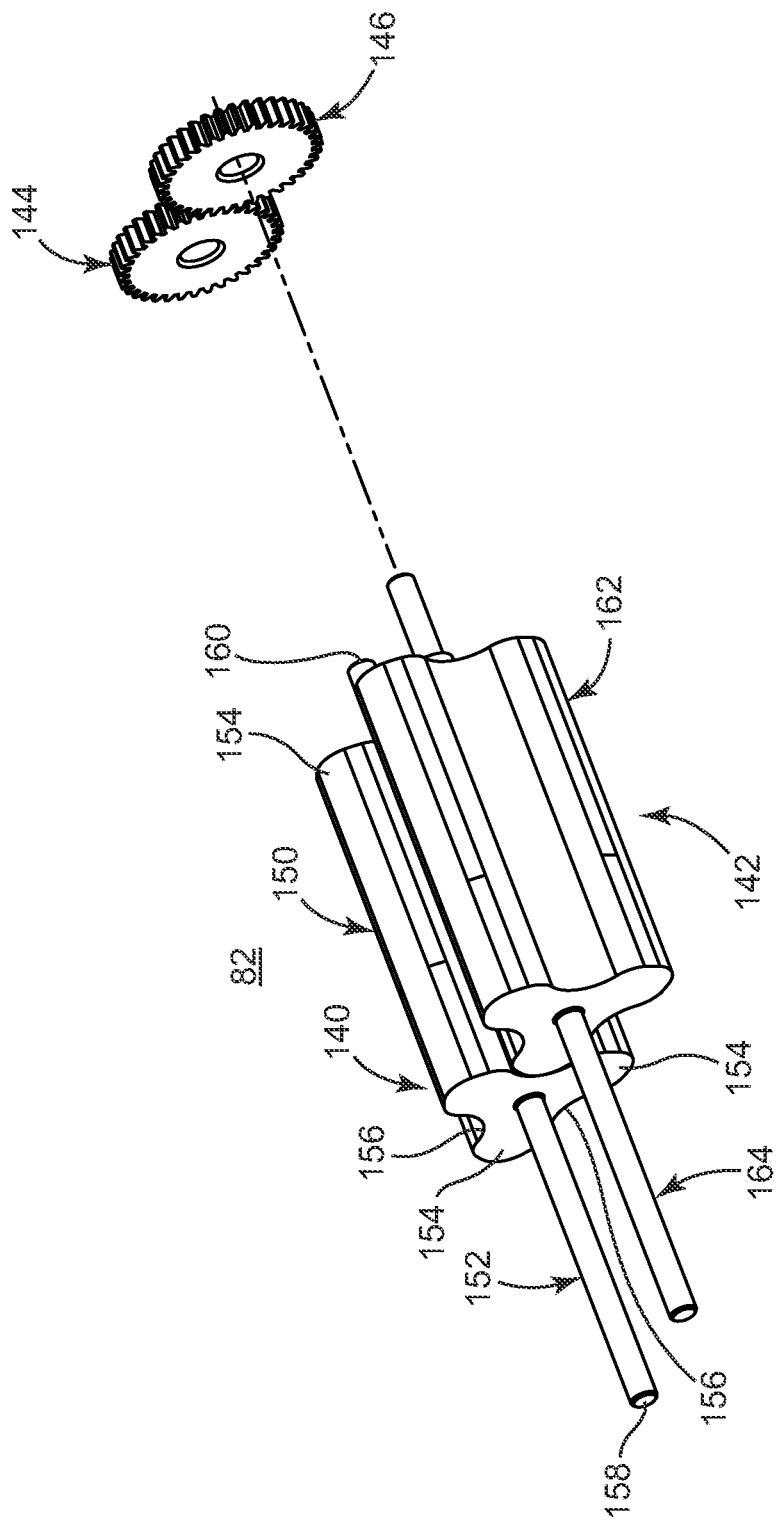

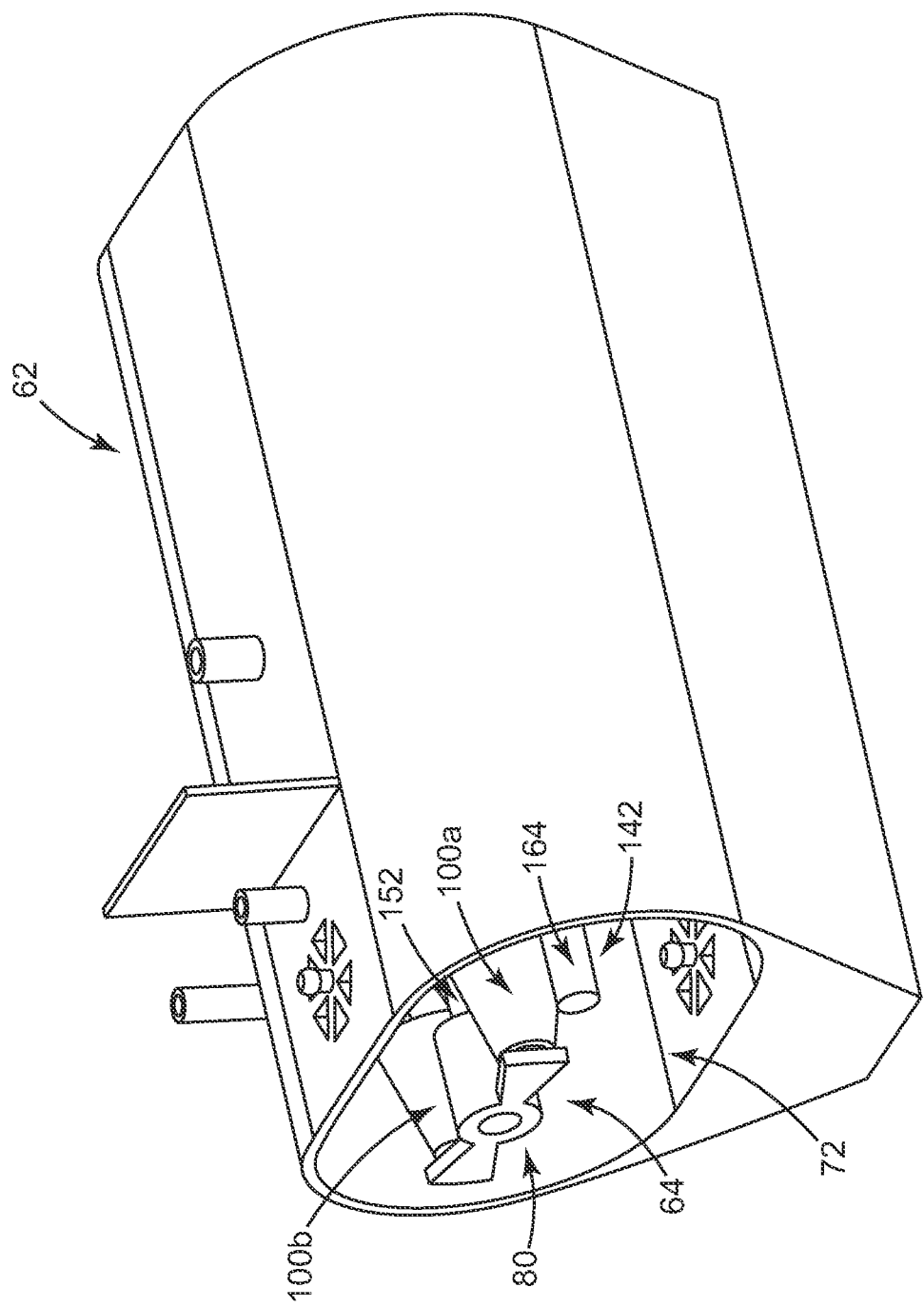

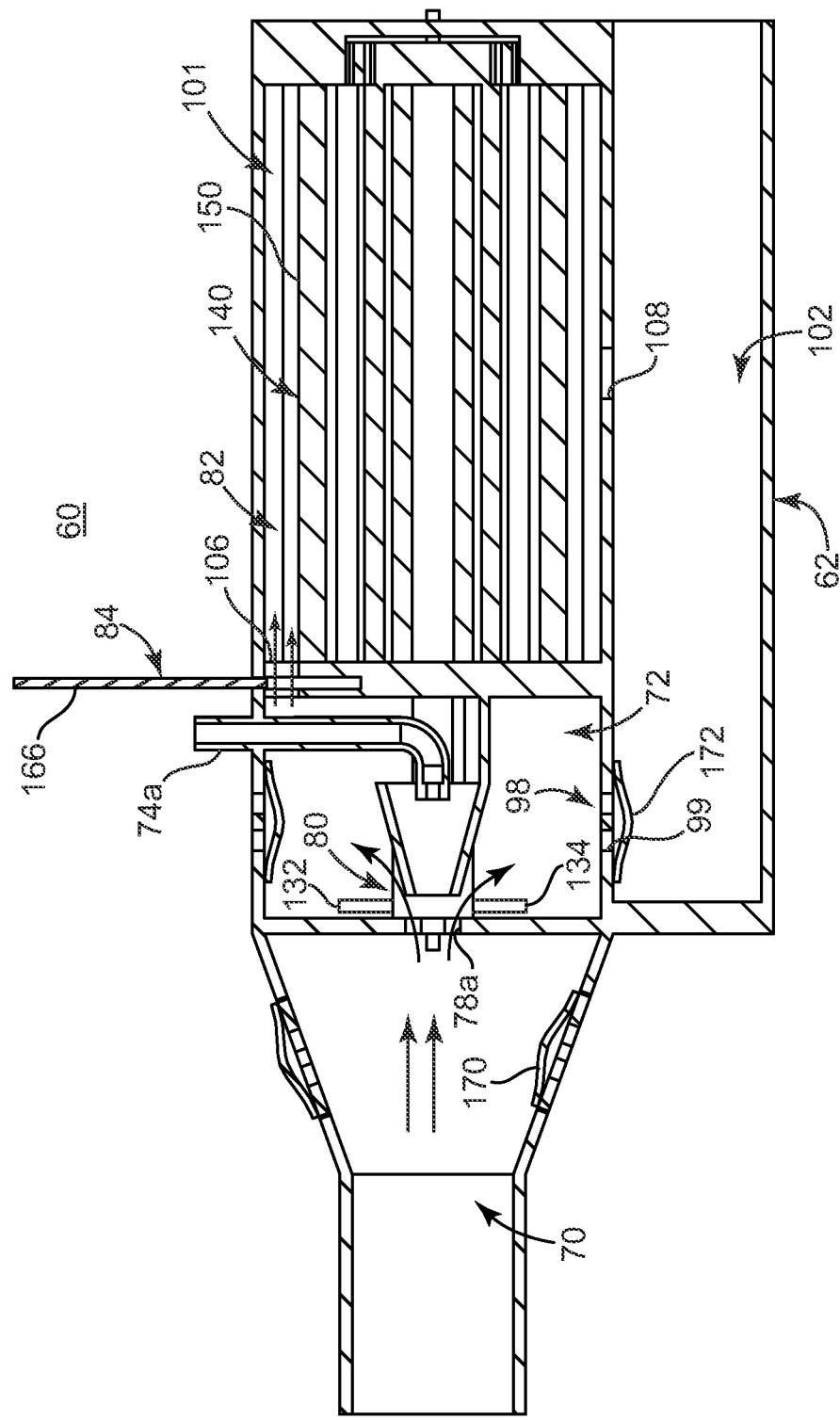

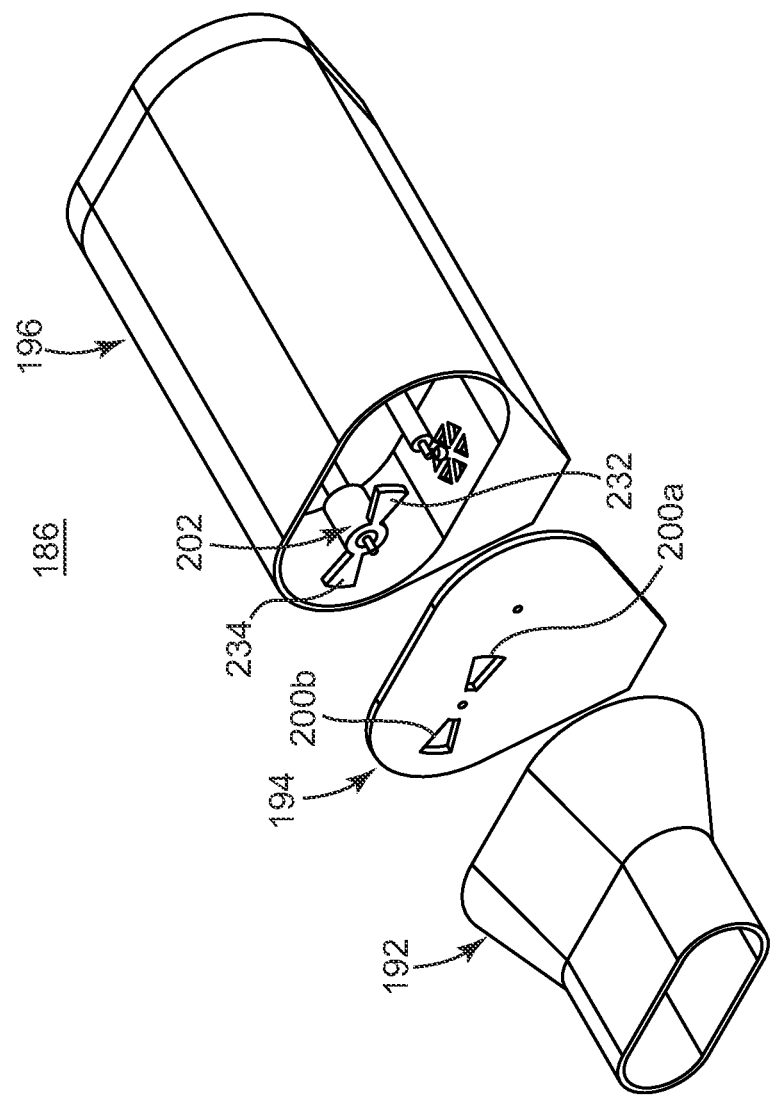

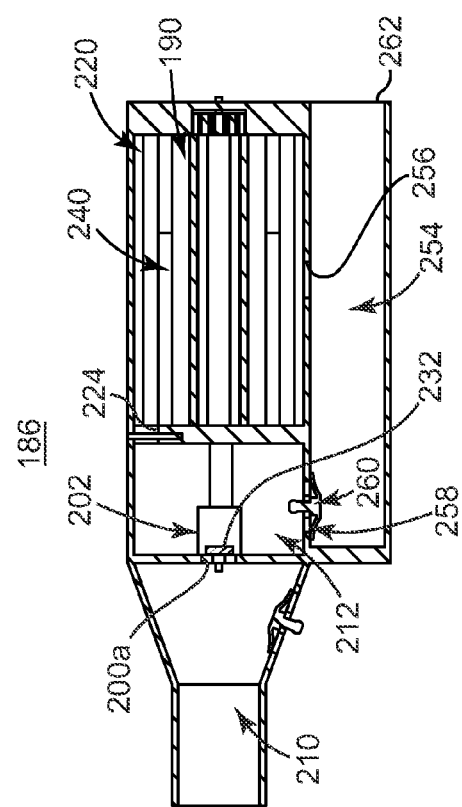
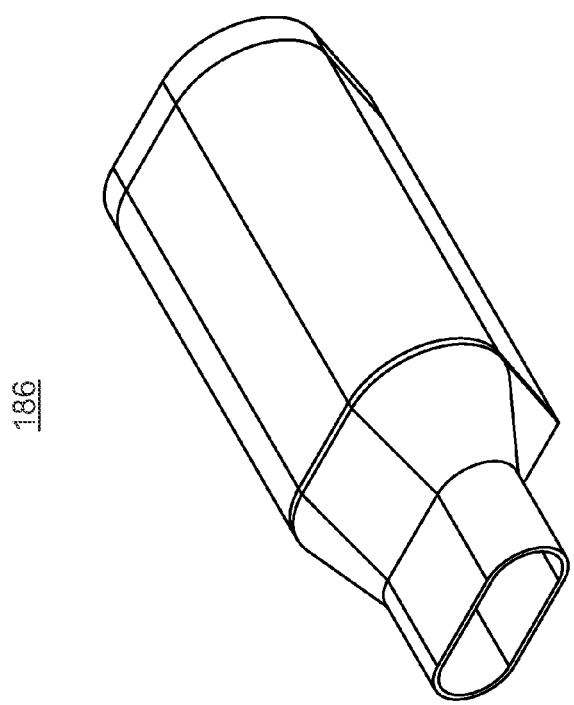
Fig. 13B
Fig. 13A

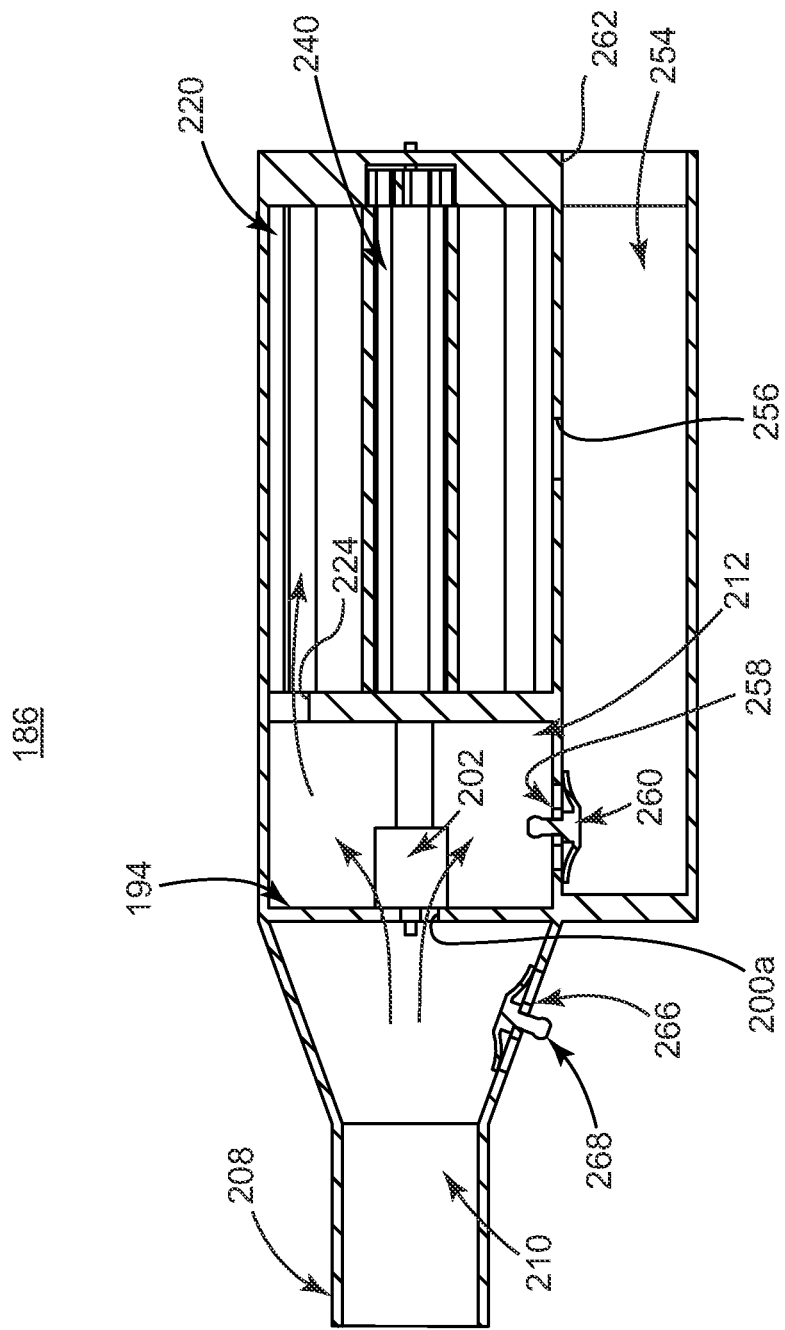

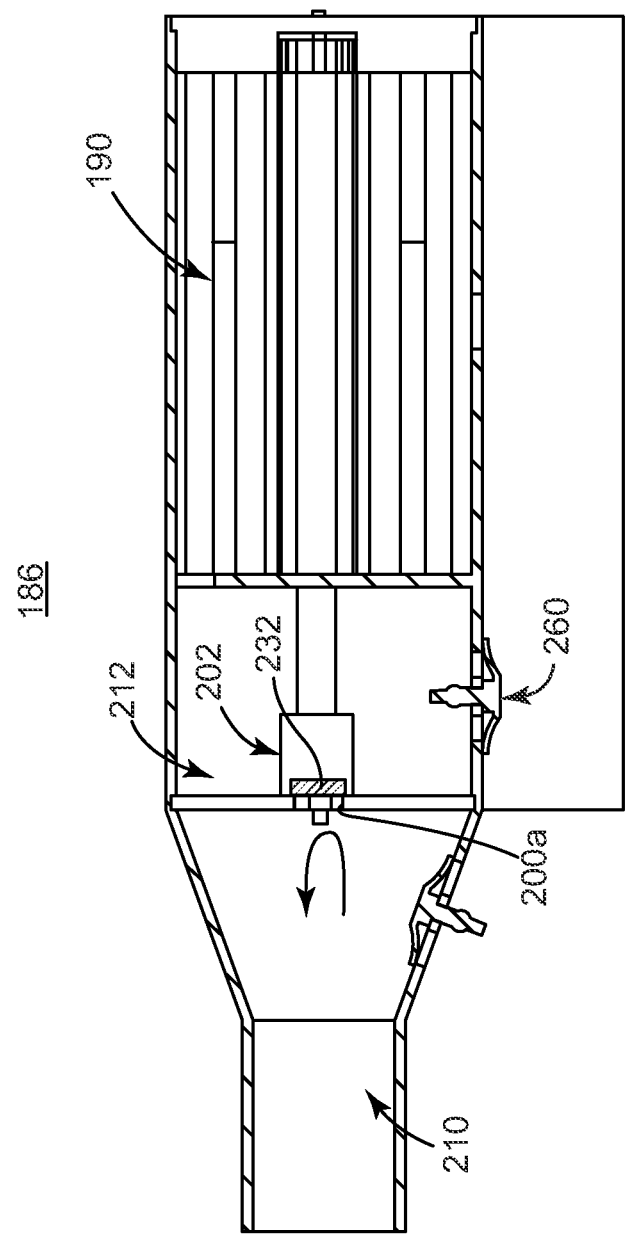

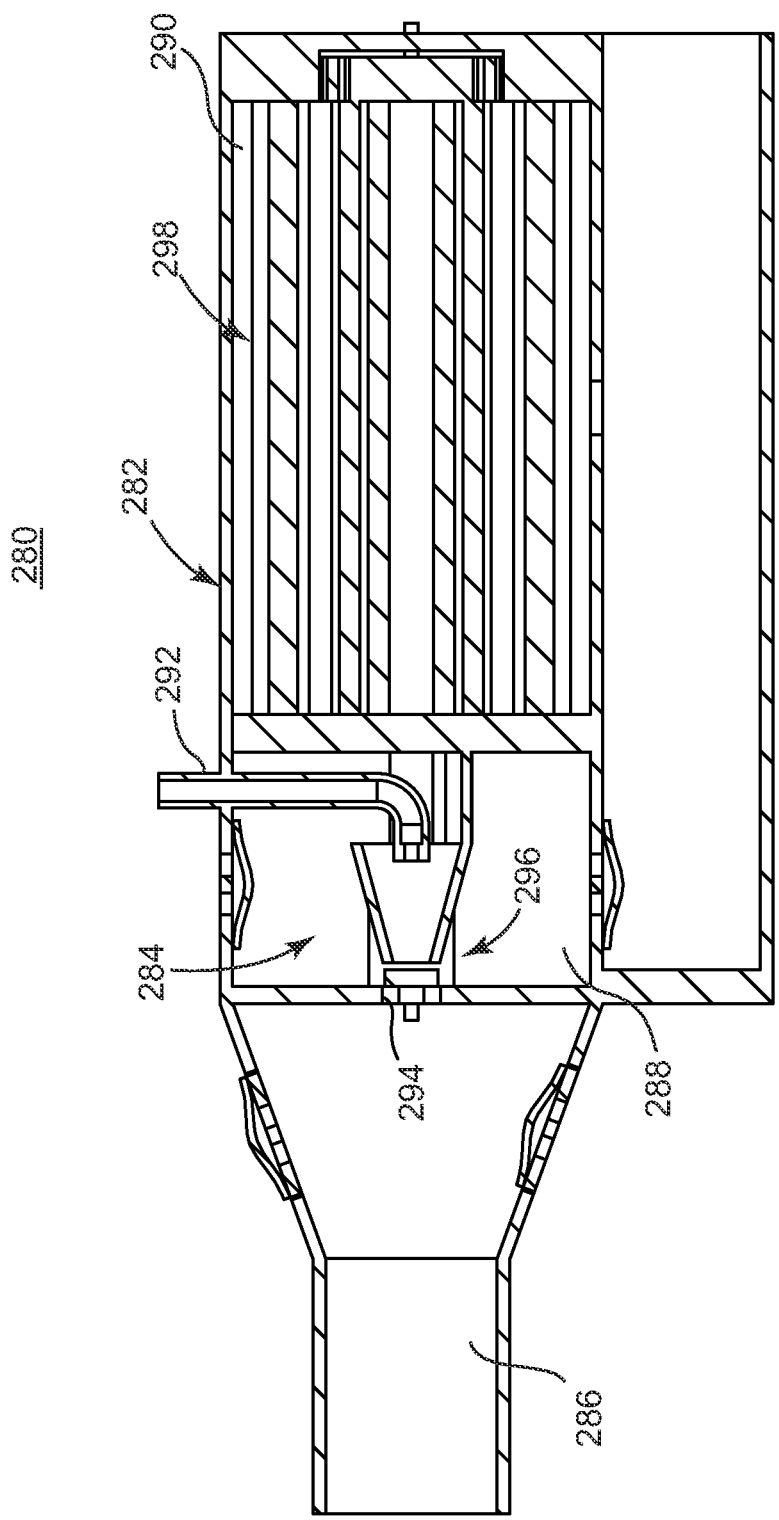

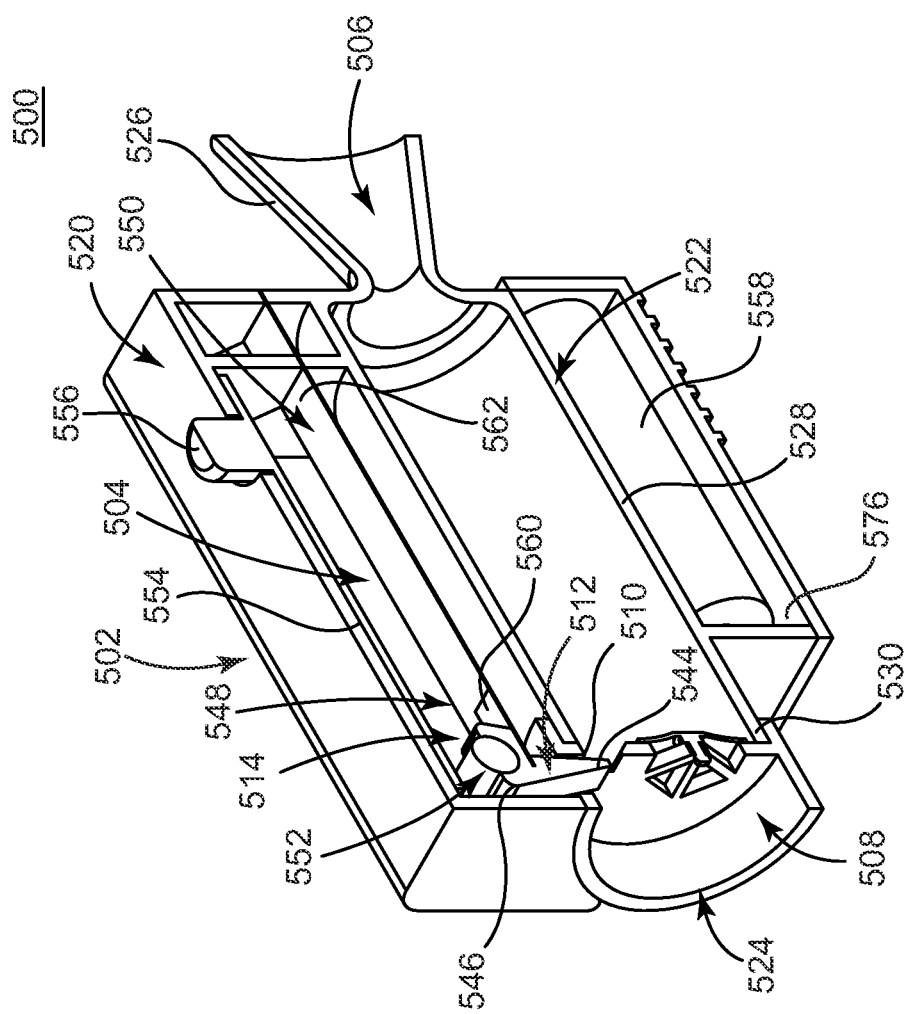

RESPIRATORY THERAPY DEVICE

CROSS-REFERENCE TO RELATED APPLICATION

This application is a continuation of U.S. patent application Ser. No. 11/670,867, entitled "Passive Respiratory Therapy Device" filed on Feb. 2, 2007, which is a continuation of U.S. patent application Ser. No. 11/559,288, entitled "Respiratory Therapy Device and Method" filed on Nov. 13, 2006; the teachings of which are incorporated herein by reference.

BACKGROUND OF THE INVENTION

The present disclosure relates to respiratory therapy devices and methods for administering breathing-relating treatments (e.g., oscillatory, continuous, etc.) to a patient. More particularly, it relates to respiratory therapy devices capable of creating oscillatory respiratory pressure pulses in response to the patient's expiratory airflow alone, or when connected to a source of positive pressure fluid (e.g., air, oxygen, etc.), or both. One or more additional therapies (e.g., continuous positive airway pressure, continuous positive expiratory pressure, delivery of aerosolized medication, etc.) are optionally available in some embodiments.

A wide variety of respiratory therapy devices are currently available for assisting, treating, or improving a patient's respiratory health. For example, positive airway pressure (PAP) has long been recognized to be an effective tool in promoting bronchial hygiene by facilitating improved oxygenation, increased lung volumes, and reduced venous return in patients with congestive heart failure. More recently, positive airway pressure has been recognized as useful in promoting mobilization and clearance of secretions (e.g., mucous) from a patient's lungs. In this regard, expiratory positive airway pressure (EPAP) in the form of high frequency oscillation (HFO) of the patient's air column is a recognized technique that facilitates secretion removal. In general terms, HFO reduces the viscosity of sputum in vitro, which in turn has a positive effect on clearance induced by an in vitro simulated cough. In this regard, HFO can be delivered or created via a force applied to the patient's chest wall (i.e., chest physical therapy (CPT), such as an electrically driven pad that vibrates against the patient's chest), or by applying forces directly to the patient's airway (i.e., breathing treatment, such as high frequency airway oscillation). Many patients and caregivers prefer the breathing treatment approach as it is less obtrusive and can more easily be administered. To this end, PAP bronchial hygiene techniques have emerged as an effective alternative to CPT for expanding the lungs and mobilizing secretions.

In the context of high frequency oscillatory breathing treatments, various devices are available. In general terms, respiratory therapy devices typically include one or more tubular bodies through which a patient breaths, with the tubular body or bodies creating or defining a patient breathing circuit. With this in mind, the oscillatory airflow effect can be created by periodically generating a pressure or positive airflow in the patient breathing circuit during one or both of an inspiratory phase or expiratory phase of the patient's breathing cycle. For example, a positive expiratory pressure (PEP) can work "against" the patient's breath during the expiratory phase of breathing. The pressure can be generated by creating a periodic (or in some instances continuous) resistance or restriction in the patient breathing circuit to expiratory airflow from the patient, or by introducing a forced fluid flow (from a positive pressure gas source) into the patient's breathing circuit in a direction opposite of the patient's exhaled air. With the airflow resistance approach, a separate, positive pressure gas source is not required. More particularly, many oscillatory positive expiratory pressure ("oscillatory PEP") therapy devices utilize the patient's breath alone to drive an oscillatory fluid flow restriction, and thus can be referred to as "passive" devices (in contrast to an "active" respiratory therapy device that relies on a separate source of positive pressure gas as described below). Passive oscillatory PEP devices are self-administering and portable.

The Flutter® mucus clearance device (available from Axcan Scandipharm Inc., of Birmingham, Ala.), is one example of an available passive, oscillatory PEP therapy device. In general terms, the Flutter device is pipe-shaped, with a steel ball in a "bowl" portion of a housing that is loosely covered by a perforated cap. The ball is situated within an airway path defined by the device's housing; when the patient exhales into the housing, then, the ball temporarily obstructs airflow, thus creating an expiratory positive airway pressure. The bowl within which the ball is located allows the ball to repeatedly move (e.g., roll and/or bounce) or flutter to create an oscillatory or vibrational resistance to the exhaled airflow. While relatively inexpensive and viable, the Flutter device is fairly sensitive, requiring the patient to maintain the device at a particular angle to achieve a consistent PEP effect. Other passive oscillatory positive expiratory pressure devices, such as the Acapella® vibratory PEP therapy system (available from Smiths Medical of London, England) and the Quake® secretion clearance therapy device (available from Thayer Medical Corp., of Tucson, Ariz.) are known alternatives to the Flutter device, and purport to be less sensitive to the position in which the patient holds the device during use. While these and other portable oscillatory PEP therapy devices are viable, opportunities for improvement remain, and patients continue to desire more uniform oscillatory PEP results.

As an alternative to the passive oscillatory PEP devices described above, continuous high frequency oscillatory (CHFO) treatment systems are also available. In general terms, the CHFO system includes a hand-held device establishing a patient breathing circuit to which a source of positive pressure gas (e.g., air, oxygen, etc.), is fluidly connected. The pressure source and/or the device further include appropriate mechanisms (e.g., control valves provided as part of a driver unit apart from the hand-held device) that effectuate intermittent flow of gas into the patient breathing circuit, and thus percussive ventilation of the patient's lungs. With this approach, the patient breathes through a mouthpiece that delivers high-flow, "mini-bursts" of gas. During these percussive bursts, a continuous airway pressure above ambient is maintained while the pulsatile percussive airflow periodically increases airway pressure. Each percussive cycle can be programmed by the patient or caregiver with certain systems, and can be used throughout both inspiratory and expiratory phases of the breathing cycle.

Examples of CHFO devices include the IPV® ventilator device (from PercussionAire Corp., of Sandpoint, Id.) and a PercussiveNeb™ system (from Vortran Medical Technology 1, Inc., of Sacramento, Calif.). These and other similar "active" systems are readily capable of providing not only CHFO treatments, but also other positive airflow modes of operation (e.g., continuous positive airway pressure (CPAP)). However, a positive pressure source is required, such that available active respiratory therapy systems are not readily portable, and are relatively expensive (especially as compared to the passive oscillatory PEP devices described above). Oftentimes, then, active respiratory treatment systems are only available at the caregiver's facility, and the patient is unable to continue the respiratory therapy at home. Instead, a separate device, such as a portable, passive oscillatory PEP device as described above must also be provided. Further, the hand-held portion of some conventional active respiratory therapy systems must be connected to an appropriate driver unit that in turn is programmed to effectuate the desired fluid flow to the patient (e.g., CHFO, CPAP, etc.). That is to say, the hand-held portion of some active systems is not self-operating, but instead relies on the driver unit for applications. Any efforts to address these and other limitations of available active respiratory therapy devices would be well-received. This limitation represents a significant drawback.

In light of the above, a need exists for respiratory devices capable of providing oscillatory PEP therapy utilizing the patient's breath alone, as well as CHFO therapy (and optionally other therapies such as CPAP) when connected to a positive pressure source. In addition, improved passive oscillatory PEP or active respiratory therapy devices are also needed.

SUMMARY OF THE INVENTION

Some aspects in accordance with principles of the present disclosure relate to a device for providing respiratory therapy to a patient during at least a portion of a patient breathing cycle otherwise including an inspiratory phase and an expiratory phase. The device includes a housing and an interrupter valve assembly. The housing includes a patient inlet, an exhaust outlet, a chamber, and a pressurized fluid supply inlet. The chamber is fluidly disposed between the patient inlet and the exhaust outlet. The interrupter valve assembly is associated with the housing and includes a control port fluidly connecting the patient inlet and the chamber. Further, the interrupter valve assembly includes a valve body adapted to selectively obstruct fluid flow through the control port. With this in mind, the device is adapted to operate in a first, passive mode and a second, active mode. In the passive mode, positive airflow to the supply inlet does not occur. The interrupter valve assembly interacts with exhaled air from the patient to create an oscillatory positive expiratory pressure effect during at least the expiratory phase. Conversely, in the active mode, positive fluid flow to the fluid supply inlet occurs and the interrupter valve assembly interacts with this fluid flow to create a continuous high frequency oscillation effect. With this configuration, then, the respiratory device can serve as a passive, oscillatory PEP device for use by a patient at virtually any location. In addition, when connected to a positive pressure gas source, the respiratory therapy device provides active therapy. In some embodiments, the interrupter valve assembly includes a drive mechanism akin to a reverse roots blower, utilizing forced air (e.g., either the patient's exhaled airflow or airflow from a separate positive gas source) to cause rotation of the roots blower lobes, that in turn cause the valve body to periodically open and close the control port. In other embodiments, the device can provide or facilitate one or more additional therapies such as continuous PEP, CPAP, delivery of aerosolized medication, etc.

Other aspects in accordance with the present disclosure relate to a method of providing respiratory therapy to a patient during at least a portion of a patient breathing cycle including an inspiratory phase and an expiratory phase. The method includes providing a respiratory therapy device including a housing and an interrupter valve assembly. The housing includes a patient inlet, an exhaust outlet, and a pressurized fluid supply inlet. The interrupter valve assembly is adapted to selectively interrupt fluid flow to or from the patient inlet. A source of pressurized fluid is fluidly coupled to the fluid supply inlet. Continuous high frequency oscillation treatment is administered to the patient via the therapy device, with the therapy device operating in an active mode. Fluid flow from the source of pressurized fluid to the fluid supply inlet is discontinued. The patient is then prompted to repeatedly perform a patient breathing cycle using the therapy device. In this regard, the therapy device administers an oscillatory positive expiratory pressure treatment to the patient while operating in a passive mode. In some embodiments, the passive mode of operation is characterized by the level of oscillatory positive expiratory pressure treatment being a function of a breathing effort of the patient, whereas the active mode of operation is characterized by a level of continuous high frequency oscillation treatment being independent of the patient's breathing effort. In yet other embodiments, the method further includes administering one or more additional therapies to the patient via the device, such as CPAP, continuous PEP, delivery of aerosolized medication, etc.

BRIEF DESCRIPTION OF THE DRAWINGS

FIG. 4A is a longitudinal, cross-sectional view of the housing of FIG. 3A taken along a patient supply inlet;

FIG. 4C is a longitudinal, cross-sectional view of the housing of FIG. 3A taken along a drive supply inlet;

FIG. 5A is an exploded, perspective view of a drive mechanism portion of the device of FIG. 2;

FIG. 6A is a perspective view illustrating partial assembly of the device of FIG. 2;

FIGS. 7A and 7B illustrate use of the device of FIG. 2 in a passive mode;

FIG. 12 is a exploded, perspective view illustrating assembly of the device of FIG. 9;

FIG. 13A is a perspective view of the device of FIG. 9;

FIG. 13B is a longitudinal, perspective view of the device of FIG. 9;

FIGS. 14A and 14B illustrate use of the device of FIG. 9 in which airflow passes from a patient inlet to a chamber;

FIGS. 15A and 15B illustrate use of the device of FIG. 9 in which airflow is obstructed from a patient inlet to a chamber;

FIG. 16 is a simplified, side sectional view of an alternative respiratory therapy device in accordance with principles of the present disclosure;

FIG. 23B is a perspective, cutaway view of the device of FIG. 23A upon final assembly;

DETAILED DESCRIPTION OF THE INVENTION

In general terms, aspects of the present disclosure relate to respiratory therapy devices and related methods of use that are: 1) capable of operating in either of an active mode (e.g., CHFO) or a passive mode (e.g., oscillatory PEP); or 2) improved passive-only oscillatory PEP devices; or 3) improved active-only devices (CHFO and/or CPAP). As used throughout this specification, an "active" therapy device is in reference to a device that requires a separate source of positive pressure fluid to effectuate a designated respiratory therapy, whereas a "passive" therapy device is in reference to a device that delivers a designated respiratory therapy in and of itself (i.e., a separate source of positive pressure fluid is not necessary). Thus, an "active-only" therapy device is one that must be connected to a separate source of positive pressure fluid. Conversely, a "passive-only" therapy device is one that is not configured to receive pressurized fluid from a separate source. Given these definitions, several of the embodiments associated with this disclosure have base constructions appropriate for passive-only, oscillatory PEP applications, as well as modified base constructions that promote use of the device as either an oscillatory PEP therapy device or, when fluidly connected to a source of pressurized fluid, as a CHFO therapy device. In yet other embodiments, the base construction can be employed with an "active only" therapy device that provides CHFO therapy (and, in some embodiments, other respiratory therapies such as CPAP) when connected to a source of positive pressure fluid. With any of these embodiments, optional features can be included to facilitate delivery of aerosolized medication.

Figure 1:
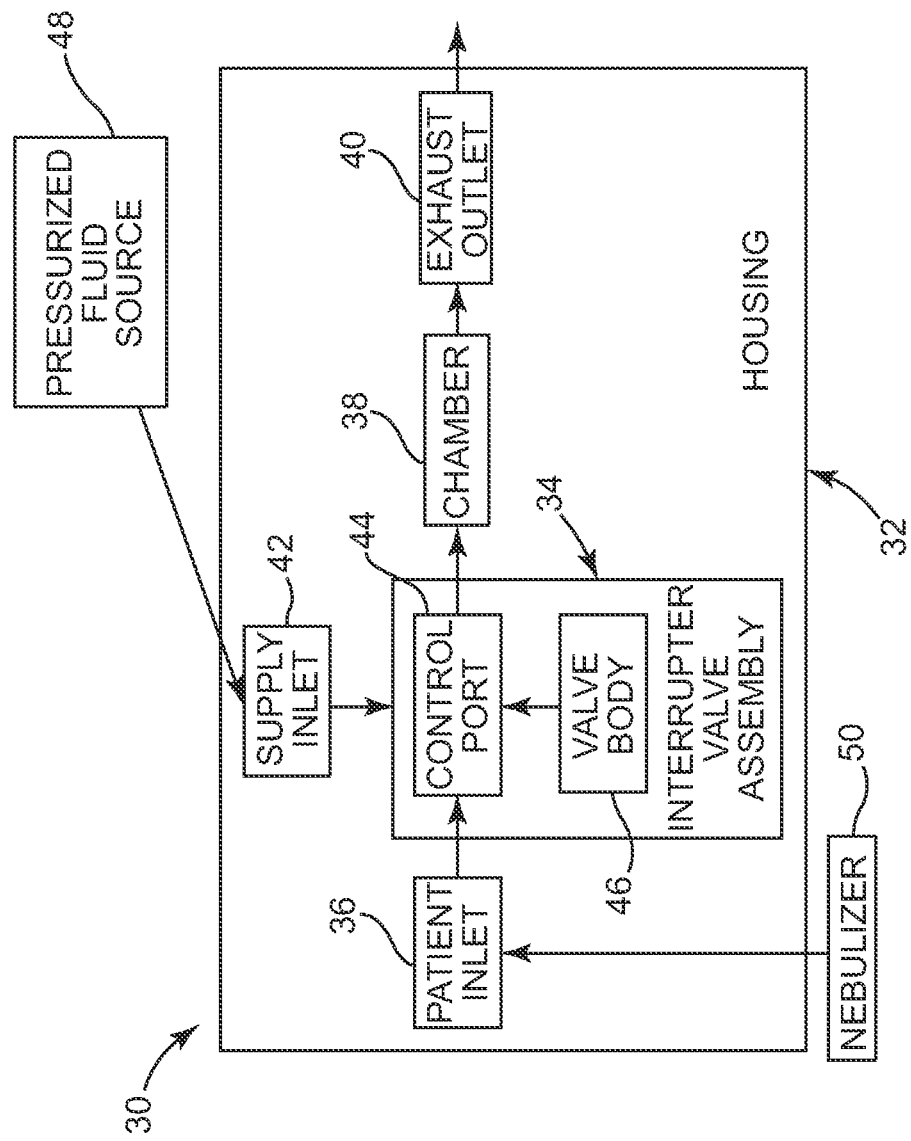
FIG. 1 is a block diagram illustrating a respiratory therapy device in accordance with principles of the present disclosure.

With the above understanding in mind, FIG. 1 is a block diagram illustrating features of a respiratory therapy device 30 in accordance with some aspects of the present disclosure. In general terms, the respiratory therapy device 30 is adapted to operate in a passive mode (e.g., oscillatory PEP) and an active mode (e.g., CHFO and optionally CPAP), and generally includes a housing 32 and an interrupter valve assembly 34. The housing 32 forms or maintains a patient inlet 36, at least one chamber 38, an exhaust outlet 40, and at least one pressurized fluid supply inlet 42. The interrupter valve assembly 34 includes at least one control port 44 and a valve body 46. The control port(s) 44 fluidly connects the patient inlet 36 and the chamber 38, whereas the valve body 46 is adapted to selectively obstruct or interrupt fluid flow through the control port(s) 44. Details on the various components are provided below. In general terms, however, by controlling or operating the valve body 46 to selectively obstruct (partially or completely) the control port(s) 44, the interrupter valve assembly 34 alters airflow/pressure characteristics to and/or from the patient inlet 36. For example, where the supply inlet 42 is not connected to a separate source of pressurized fluid 48, as a patient (not shown) exhales into the patient inlet 36, the interrupter valve assembly 34 operates to periodically at least partially close the control port(s) 44, thereby establishing a resistance to airflow or back pressure in the patient inlet 36. This periodic back pressure, in turn, provides an oscillatory PEP therapy. In addition, when the supply inlet 42 is fluidly connected to the pressurized fluid source 48, the interrupter valve assembly 34 operates to periodically at least partially interrupt fluid flow from the supply inlet 42 to the patient inlet 36. This interrupted supply of pressure toward the patient serves as a CHFO therapy. As described below, the device 30 can optionally include features that selectively disable all or a portion of the interrupter valve assembly 34 in conjunction with the supply of pressurized fluid to the supply inlet 42 in providing a CPAP therapy (either along or simultaneous with CHFO therapy).

In light of the above, the respiratory therapy device 30 provides both active and passive modes of operation, allowing the patient (not shown) to receive oscillatory PEP treatments with the device 30 at virtually any location, as well as CHFO treatments (and optionally other active treatments such as CPAP) when the patient is at a location at which the pressurized fluid source 48 is available. The respiratory therapy device 30 can further be configured to facilitate additional respiratory therapy treatments, such as delivery of aerosolized medication (for example via a nebulizer 50). The nebulizer 50 can be connected to a port (not shown) provided by the housing 32, or can include an appropriate connection piece (e.g., T-connector or line) that is fluidly connected to the housing 32 (e.g., to the patient inlet 36) when desired. Finally, while the pressurized fluid source 48 is shown apart from the housing 32, in other embodiments, the pressurized fluid source 48 can be attached to, or carried by, the housing 32 (e.g., a pressurized canister mounted to the housing 32).

Figure 2:
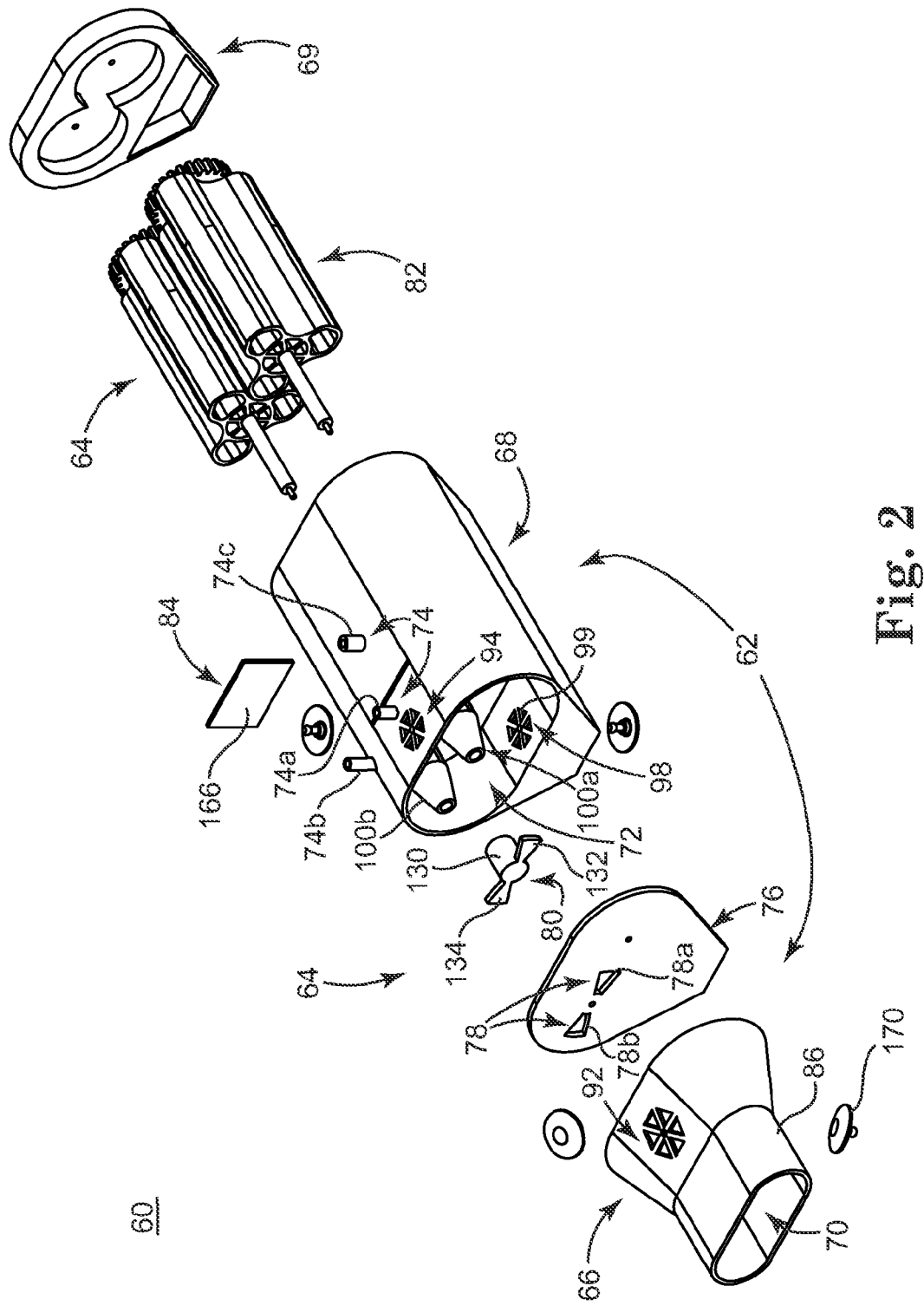
FIG. 2 is an exploded, perspective view of a respiratory therapy device in accordance with principles of the present disclosure.

With the above in mind, the respiratory therapy device 30 can assume a variety of forms capable of operating in a passive mode (e.g., oscillatory PEP therapy) and an active mode (e.g., CHFO therapy). One embodiment of a respiratory therapy device 60 providing these features is shown in FIG. 2. The therapy device 60 generally includes a housing 62 (referenced generally) and an interrupter valve assembly 64 (referenced generally). The housing 62 includes a leading section 66, a trailing section 68, and an end plate 69. The leading section 66 defines a patient inlet 70, whereas the trailing section 68 defines a first chamber 72, a second chamber (hidden in the view of FIG. 2), an exhaust outlet (hidden in FIG. 2), and one or more supply inlets 74. The interrupter valve assembly 64 includes a plate 76 forming one or more control ports 78 (e.g., the control ports 78a, 78b), a valve body 80, and a drive mechanism 82. Details on the various components are provided below. In general terms, however, the drive mechanism 82 is retained within the second chamber of the housing 62 and is assembled to the valve body 80 for causing rotation thereof. The valve body 80, in turn, is located in close proximity to the control ports 78 such that rotation of the valve body 80 selectively opens and closes (e.g., partial or complete obstruction) the control ports 78 relative to the first chamber 72 and the patient inlet 70. Finally, the supply inlet(s) 74 are fluidly connected to distribution points within the housing 62. During use, and in a passive mode of operation, the therapy device 60 generates oscillatory PEP via operation of the drive mechanism 82 in response to the patient's exhaled breath. In addition, the therapy device 60 provides an active mode of operation in which the interrupter valve assembly 64 causes delivery of CHFO fluid flow to the patient inlet 70 in acting upon positive fluid flow from the supply inlet(s) 74. In this regard, a control means 84 (referenced generally) can be provided that facilitates operation of the therapy device 60 in a desired mode.

Figure 3A:
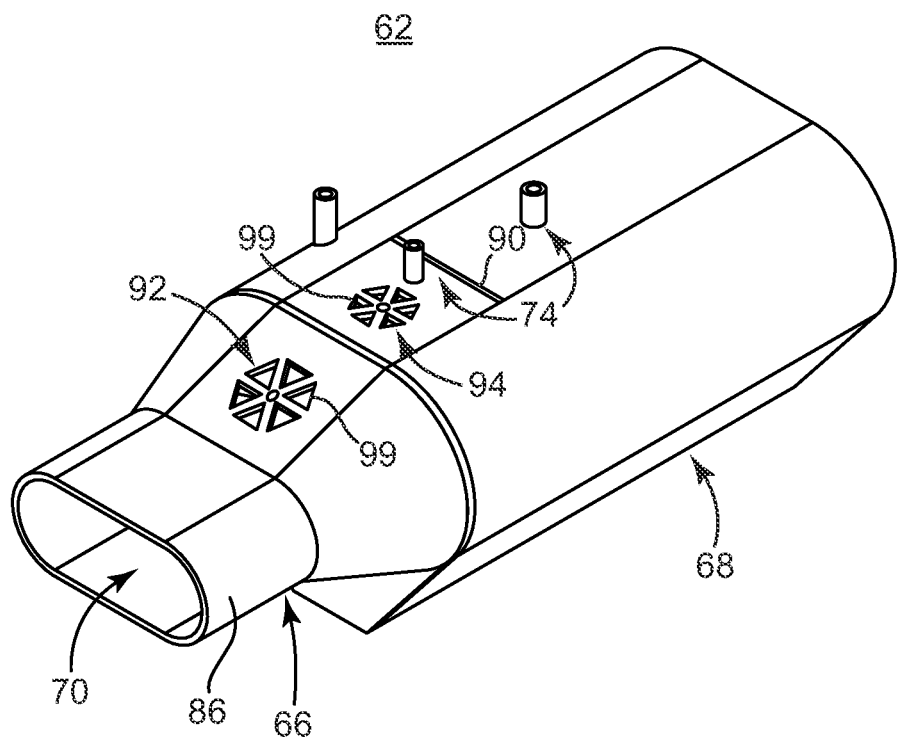
FIG. 3A is a perspective view of a housing portion of the device of FIG. 2.
Figure 3B:
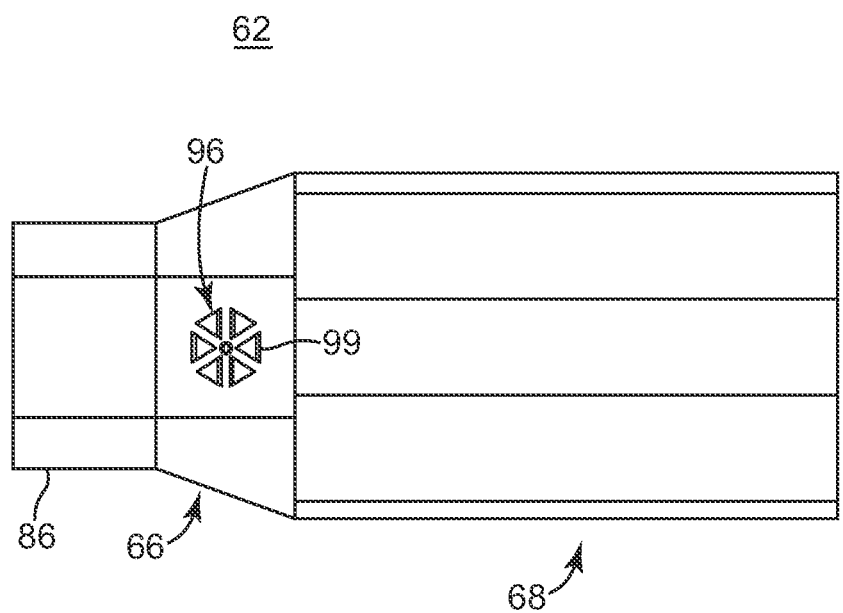
FIG. 3B is a bottom view of the housing of FIG. 3A.

The housing 62 is shown in greater detail in FIGS. 3A and 3B upon final assembly. The housing 62 is generally sized and shaped for convenient handling by a patient, with the leading section 66 forming a mouthpiece 86 sized for placement in the patient's mouth and through which the patient's respiratory cycle interacts with the patient inlet 70. The mouthpiece 86 can be integrally formed with one or more other component(s) of the housing 62, or can be separately formed and subsequently assembled thereto.

The housing 62 can form or define fluid flow features in addition to the supply inlets 74. For example, and as best shown in FIG. 3A, the trailing section 68 forms a slot 90 as part of the control assembly 84 (FIG. 2). As described below, the control assembly 84 can assume a variety of forms, but in some embodiments includes a body slidably disposed with the slot 90. With alternative constructions, however, the slot 90 can be eliminated.

Relative to the top perspective view of FIG. 3A, the housing 62 can further form first and second relief port arrangements 92, 94. A third relief port arrangement 96 can also be provided as shown in the bottom view of FIG. 3B. Finally, as best shown in FIG. 2, a fourth relief port arrangement 98 is provided within an interior of the housing 62. Operation of the therapy device 60 in connection with the relief port arrangements 92-98 is described in greater detail below. In general terms, however, the relief port arrangements 92-98 each include one or more apertures 99, and are adapted to maintain a valve structure (not shown), such as a one-way umbrella valve, that permits fluid flow into or out of the aperture(s) 99 of the corresponding port arrangement 92-98 in only a single direction. As such, the relief port arrangements 92-98 can assume a variety of configurations differing from those illustrated. Similarly, additional relief port arrangements can be provided, and in other embodiments one or more of the relief port arrangements 92-98 can be eliminated.

Returning to FIG. 2, the supply inlets 74, otherwise carried or formed by the housing 62, include, in some embodiments, first and second patient supply inlets 74a, 74b, as well as a drive supply inlet 74c. The patient supply inlets 74a, 74b are fluidly connected to first and second nozzles 100a, 100b, respectively, each positioned to direct fluid flow toward a corresponding one of the control ports 78a, 78b (otherwise formed by the plate 76). A relationship of the nozzles 100a, 100b and the control ports 78a, 78b relative to the internal features of the housing 62 is provided below. It will be understood at the outset, however, that while two of the control ports 78a, 78b are shown and described, in other embodiments, one or three (or more) control ports are also acceptable. Similarly, a nozzle/patient supply inlet need not be provided for each of the control ports 78a, 78b (e.g., the patient supply inlet 74b/nozzle 100b can be eliminated), or two or more supply inlet/nozzles can be directed toward a single one of the control ports 78. Even further, two or more supply inlets 74 can be fluidly associated with a single nozzle 100.

With the above in mind, FIG. 4A is a longitudinal cross-sectional view of the housing 62 upon final assembly taken through the first patient supply inlet 74a. The leading portion 66, the trailing portion 68 and the end plate 69 are generally assembled to one another as shown. As a point of reference, the view of FIG. 4A further illustrates the control means 84 in an open position relative to the housing 62, and reflects that the plate 76 can be an integral component of the housing 62. Regardless, the housing 62 is shown in FIG. 4A as defining the first chamber 72, as well as a second chamber 101, and an exhaust chamber 102. The first chamber 72 is defined, in part, by the plate 76 and an intermediate wall 104, with the plate 76 fluidly separating the patient inlet 70 from the first chamber 72. In this regard, the patient inlet 70 is fluidly connected to the first chamber 72 via the control ports 78 (it being understood that only the first control port 78a is visible in FIG. 4A). The first chamber 72 is separated from the second chamber 101 by the intermediate wall 104, with fluid connection between the chambers 72, 101 being provided by a passage 106. As described in greater detail below, the passage 106 can be fluidly closed via operation of the control means 84. Regardless, the second chamber 101 is fluidly connected to the exhaust chamber 102 via an outlet opening 108. The first chamber 72 is also fluidly connected to the exhaust chamber 102, via the fourth relief port arrangement 98. As a point of reference, FIG. 4A reflects that a one-way valve structure 110 is associated with the fourth relief port 98 and is configured such that fluid flow can only occur from the first chamber 72 to the exhaust chamber 102. Finally, the exhaust chamber 102 terminates at an exhaust outlet 112 that is otherwise open to ambient.

With the above conventions in mind, the first nozzle 100a is positioned within the first chamber 72, and includes or defines an inlet end 114 and an outlet end 116. The inlet end 114 is fluidly connected to the first patient supply inlet 74a such that fluid flow through the first patient supply inlet 74a is directed toward the outlet end 116. The outlet end 116, in turn, is aligned with the first control port 78a so as to direct fluid flow from the first nozzle 100a to the first control port 78a. In some embodiments, the first nozzle 100a tapers in diameter from the inlet end 114 to the nozzle end 116, such that a jet-like fluid flow from the first patient supply inlet 74a to the first control port 78a is established. In this regard, ambient air can be entrained into the fluid flow from the nozzle 100a (as well as the nozzle 100b) via the second relief port arrangement 94. A one-way valve structure 118 is illustrated in FIG. 4A as applied to the relief port arrangement 94, and dictates that ambient air can only enter the first chamber 72 (and thus the nozzle 100 fluid flow). Though not shown, operation of the valve structure 118 can be further controlled by a control mechanism that serves to selectively maintain the valve structure 118 in a closed state (e.g., during a passive mode of operation as described below). In other embodiments, entrained ambient airflow within the first chamber 72 can be provided in a different manner (e.g., not including the relief port arrangement 94), or can be eliminated.

Figure 4B:
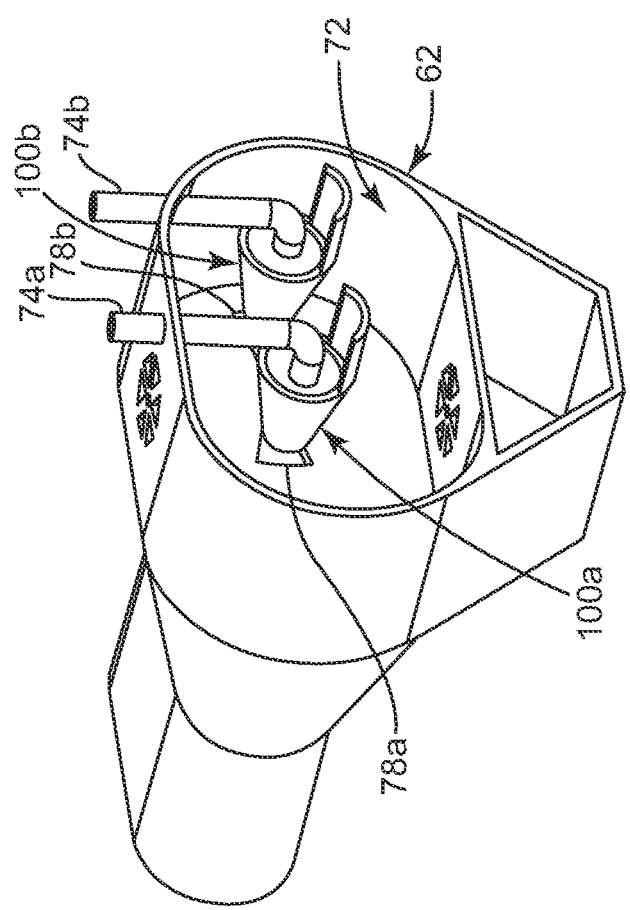
FIG. 4B is a rear, perspective view of a leading portion of the housing of FIG. 3A.

Regardless of whether ambient air is introduced into the first chamber 72, a gap 120 (referenced generally) is established between the outlet end 116 and the plate 76 (and thus the first control port 78a). As described in greater detail below, the gap 120 is sized to facilitate assembly and movement of the valve body 80 (FIG. 2). Though not shown, the second patient supply inlet 74b/second nozzle 100b (FIG. 2) has a similar construction and relationship relative to the plate 76/second control port 78b. Thus, and as best shown in FIG. 4B, the first patient supply inlet 74a/nozzle 100a directs positive pressure fluid from a separate source toward the first control port 78a, and the second patient supply inlet 74b/nozzle 100b directs positive pressure fluid toward the second control port 78b.

The drive supply inlet 74c (FIG. 2) is similarly fluidly connected to an interior of the housing 62. In particular, the drive supply inlet 74c is fluidly connected to the second chamber 101 as shown in FIG. 4C. As described in greater detail below, a portion of the drive mechanism 82 (FIG. 2) is retained within the second chamber 101, with fluid flow from the drive supply inlet 74c serving to actuate or drive the drive mechanism 82 during an active mode of operation.

Returning to FIG. 2, the interrupter valve assembly 64 again includes the valve body 80 that is driven by the drive mechanism 82. In some embodiments, the valve body 80 has a propeller-like construction, and includes a base 130, a first valve plate segment 132, and a second valve plate segment 134. The base 130 is configured for assembly to a corresponding portion of the drive mechanism 82 as described below. The plate segments 132, 134 extend in a radial fashion from the base 130, and each have a size and shape commensurate with a size and shape of a corresponding one the control ports 78a, 78b. For example, a size and/or shape of the valve plate segments 132, 134 can be identical, slightly smaller or slightly larger than a size and/or shape of the control ports 78a, 78b. Further, in some embodiments, a circumferential position of the plate segments 132, 134 relative to the base 130 corresponds with that of the control ports 78a, 78b such that when the base 130 is centrally positioned between the control ports 132, 134, the control port 78a, 78b can be simultaneously obstructed by the plate segments 132, 134. Thus, with the one embodiment of FIG. 2, the control ports 78a, 78b are symmetrically opposed, and the valve plate segments 132, 134 are similarly oriented. Alternatively, a position of the valve plate segments 132, 134 can be spatially offset relative to a position of the control ports 78a, 78b; with this alternative construction, the control ports 78a, 78b are not simultaneously obstructed during movement of the valve body 80.

While the valve body 80 is shown as including two of the valve plate segments 132, 134, any other number, either greater or lesser is also acceptable, and the number of plate segment(s) 132, 134 provided need not necessarily equal the number of control ports 78. In other embodiments, for example, the valve body 80 is configured and positioned so as to fluidly interface with only one of the control ports 78 as described below. Even further, the valve body 80 can have configurations differing from the propeller-like construction shown. Regardless, the valve body 80 is constructed such that all of the control port(s) 78 can simultaneously be obstructed (e.g., completely blocked or less than completely blocked) by the valve body 80 in some embodiments.

The drive mechanism 82 is shown in greater detail in FIG. 5A. In some embodiments, the drive mechanism 82 is akin to a reverse roots blower device and includes first and second lobe assemblies 140, 142, and first and second gears 144, 146. The lobe assemblies 140, 142 can be identical, with the first lobe assembly 140 including a lobe body 150 and a shaft 152. The lobe body 150 includes three longitudinal lobe projections 154, adjacent ones of which are separated by a valley 156. Although three of the lobe projections 154/valleys 156 are illustrated in FIG. 5A, any other number is also acceptable; however, preferably at least two of the lobe projections 154/valleys 156 are provided. Regardless, the shaft 152 is, in some embodiments, coaxially mounted within the lobe body 150, extending from a first end 158 to a second end 160. The first end 158 is sized for assembly to the valve body base 130 (FIG. 2), whereas the second end 160 is sized for assembly to the first gear 144. Other constructions are also contemplated such as integrally molding or forming two or more of the lobe body 150, shaft 154, and/or gear 140. The second lobe assembly 142 is similarly constructed, and generally includes a lobe body 162 coaxially maintained by a shaft 164 that in turn is sized for assembly to and/or formed as part of the second gear 146.

Figure 5B:
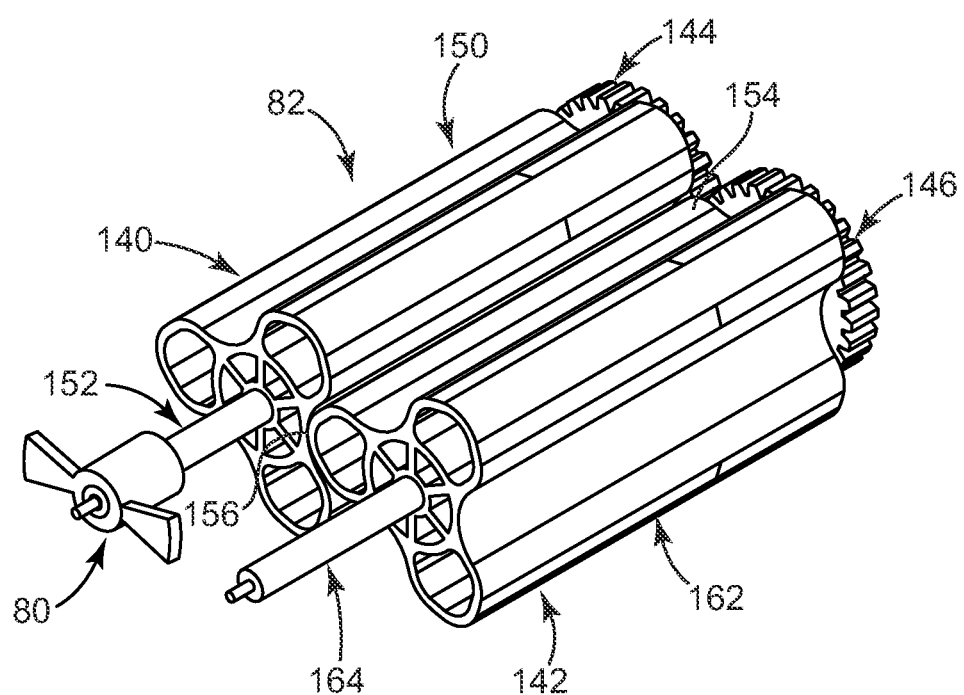
FIG. 5B is a perspective view of the drive mechanism of FIG. 5A upon final assembly.

As shown in FIG. 5B, the lobe bodies 150, 162 are configured for meshed engagement (e.g., one of the lobe projections 154 of the second lobe body 162 nests within one of the valleys 156 of the first lobe body 160), as are the first and second gears 144, 146 (it being understood that upon final assembly meshed engagement between the lobe bodies 150, 162 and between the gears 144, 146 is simultaneously achieved). With this construction, then, the lobe assemblies 140, 142 rotate in tandem, but in opposite directions (e.g., relative to the orientation of FIG. 5B, clockwise rotation of the first lobe body 150 translates into counterclockwise rotation of the second lobe body 162). The shafts 152, 164 are affixed to the corresponding lobe body 150, 162, respectively, such that rotation of the lobe bodies 150, 162 is translated directly to the gears 144, 146, respectively, via the shafts 152, 164. Thus, the gears 144, 146 serve to maintain a desired intermeshing relationship between the lobe bodies 150, 162. With the reverse roots blower configuration of the drive mechanism 82, a relatively small force (e.g., fluid flow) is required to initiate and maintain movement of the lobe assemblies 140, 142 at a desired rotational speed. In other embodiments, the number of lobe projections 154 can be increased so that the lobe bodies 150, 162 effectively interface as gears such that the gears 144, 146 can be eliminated. Regardless, upon final assembly, rotation of the first lobe assembly 140 translates into rotation of the valve body 80.

Figure 6B:
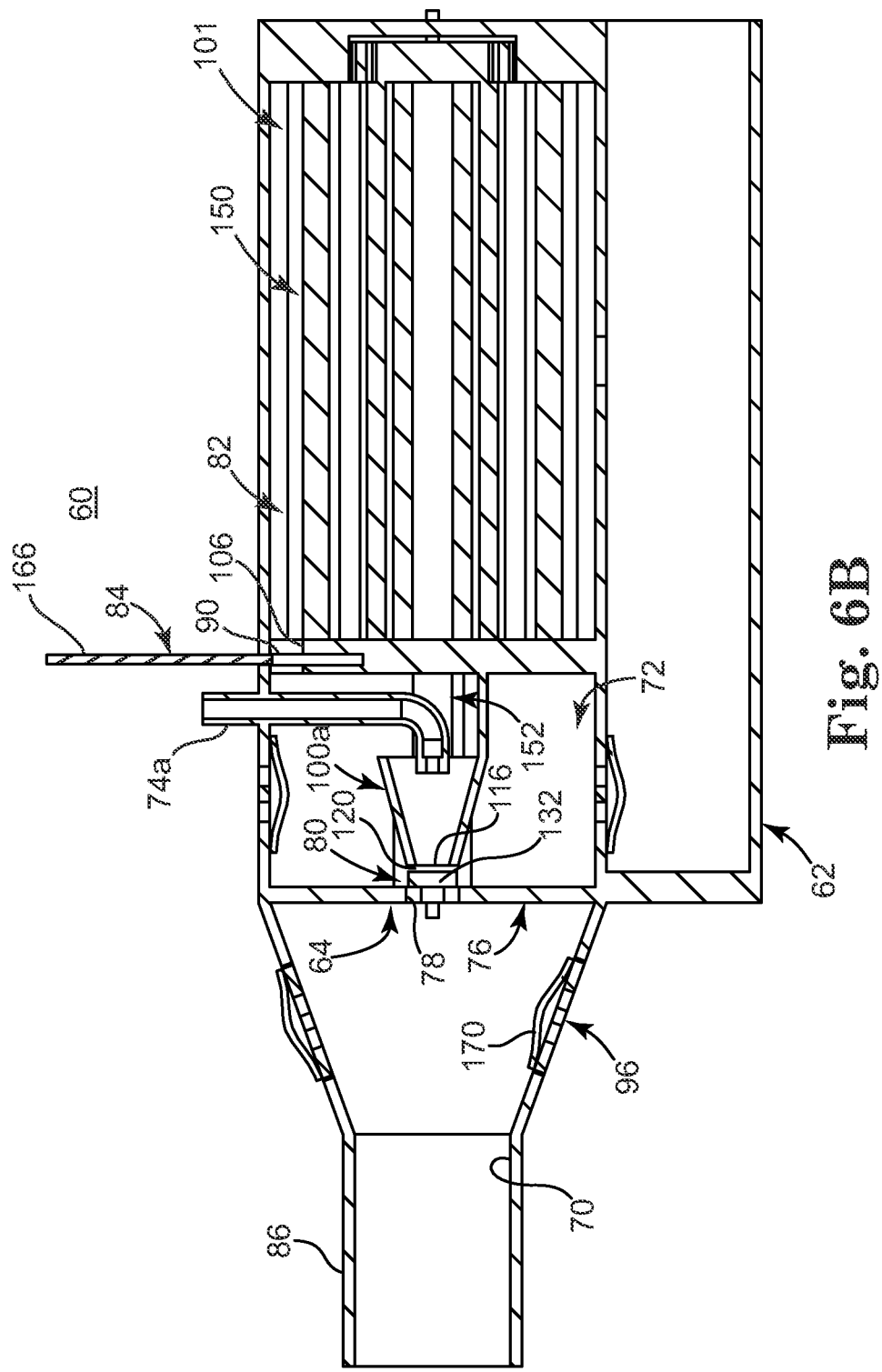
FIG. 6B is a longitudinal, cross-sectional view of the device of FIG. 2 upon final assembly, taken along a patient supply inlet.

Assembly of the interrupter valve assembly 64 to the housing 62 is partially shown in FIG. 6A. In particular, the valve body 80 is maintained immediately adjacent the nozzles 100a, 100b via the shaft 152 that otherwise extends into the first chamber 72. The shaft 164 of the second lobe assembly 142 (referenced generally in FIG. 6A, shown in greater detail in FIG. 5A) also extends into, and is supported at, the first chamber 72 (it being understood that the opposite end of each of the shafts 152, 164 is also supported, for example at or by the end plate 69 (FIG. 2)). As shown in FIG. 6B, that otherwise is a longitudinal cross-sectional view taken through the first patient supply inlet 74a, the first lobe body 150 is maintained within the second chamber 101, as is the second lobe body 162 (hidden in the view of FIG. 6B). The shaft 152 maintains the valve body 80 such that the valve plate segments 132, 134 (it being understood that the second plate segment 134 is hidden in the view of FIG. 6B) are located in the gap 120 between the outlet end 116 of the first nozzle 100a and the plate 76 (as well as between the second nozzle 100b, that is otherwise hidden in the view of FIG. 6B, and the plate 76). With rotation of the valve body 80 (via the drive mechanism 82), the valve plate segments 132, 134 repeatedly obstruct and "open" the control ports 78 relative to the first chamber 72. In other words, the interrupter valve assembly 64 (referenced generally in FIG. 6B) operates to periodically stop or substantially stop fluid flow between the patient inlet 68 and the first chamber 72 as described below. While the valve body 80 has been described as being assembled to the first shaft 152, in other embodiments, the second shaft 164 rotates the valve body 80. In other embodiments, each of the shafts 152, 164 can maintain a valve body.

With the above understanding in mind, forced movement of the drive mechanism 82 can occur in one of two manners that in turn are a function of whether the device 60 is operating in a passive mode (e.g., oscillatory PEP) or an active mode (e.g., CHFO). For example, in the passive mode, the respiratory therapy device 60, and in particular the drive mechanism 82, operates solely upon the patient's exhaled air or breath. In this regard, and with reference to FIGS. 2 and 6B, in the passive mode, the control means 84 is positioned such that the passage 106 is open and fluidly connects the first and second chambers 72, 101. In some embodiments, the control means 84 includes a tab 166 slidably positioned within the slot 90; in the "open" state of FIGS. 2 and 6B, the tab 166 is retracted from the slot 90. The control means 84 can assume a wide variety of other forms also capable of selectively opening or closing the passage 106. The supply inlets 74a-74c are fluidly closed or otherwise fluidly isolated from any external positive pressure fluid source (e.g., the pressurized fluid source 48 of FIG. 1 is disconnected from the respiratory therapy device 60; fluid flow from the pressurized fluid source 48 is diverted from the supply inlets 74a-74c; etc.). To this end, in some embodiments the supply inlets 74a-74c can be exteriorly closed (for example, by a cap assembly (not shown)).

With the therapy device 60 configured as described above, the passive mode of operation can entail the mouthpiece 86 (or other patient interface piece (not shown) otherwise attached to the mouthpiece 86) is inserted into the patient's mouth, and the patient being prompted to breathe through the therapy device 60. During an inspiratory phase of the patient's breathing cycle, ambient air is readily drawn into the housing 62 via the third relief port arrangement 96 (that otherwise includes a one-way valve structure 170 (FIG. 6B) controlling airflow therethrough). Thus, the patient can easily and readily inhale air.

During the expiratory phase, exhaled airflow is directed from the patient/mouthpiece 86, through the patient inlet 68, and toward the plate 76. The exhaled air can fluidly pass or flow from the patient inlet 68 to the first chamber 72 via the control ports 78 when the control ports 78 are otherwise not completely obstructed by the valve body 80 (and in particular the valve plate segments 132, 134). An example of this relationship is shown in FIG. 7A whereby the valve body 80 has been rotated such that the plate segments 132, 134 are "away" from the control port 78a (as well as the control port 78b (hidden in the view of FIG. 7A)). Thus, the exhaled air flows through the control ports 78 and into the first chamber 72 (represented by arrows in FIG. 7A).

Figure 7B:
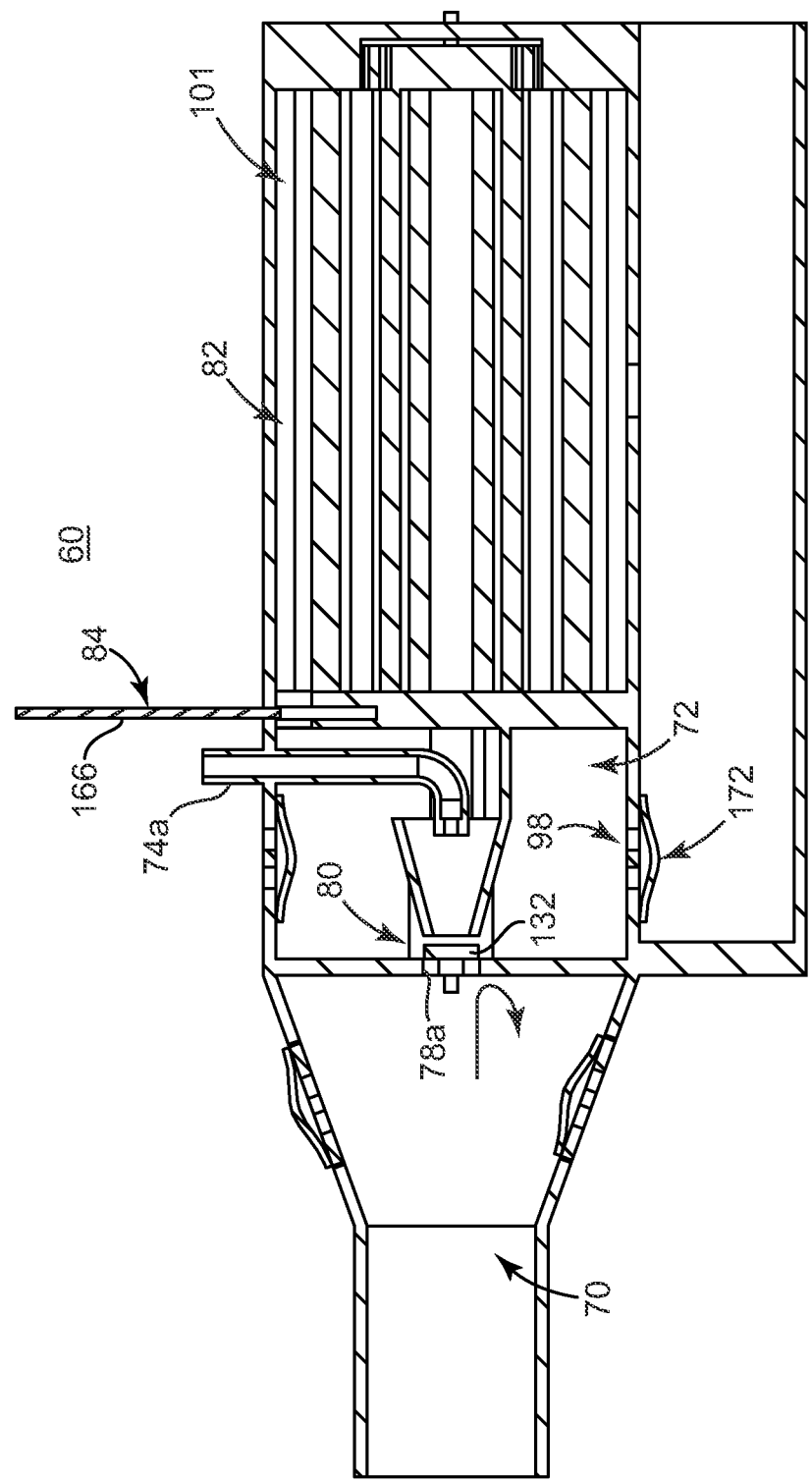

When the airflow into the first chamber 72 is at a pressure below the opening pressure of a valve structure 172 associated with the fourth relief port arrangement 98, the apertures 99 of the relief port arrangement 98 remain fluidly closed, and all of the airflow through the first chamber 72 flows into the second chamber 101 via the passage 106 (shown by arrows in FIG. 7A). Conversely, where the pressure within the first chamber 72 is above the bypass pressure associated with the valve structure 172, the valve structure 172 "opens" to allow a portion of the airflow within the first chamber 72 to flow into the exhaust chamber 102. In this manner, the pressure drop across the second chamber 101 remains approximately equal with the opening pressure associated with the valve structure 172. Alternatively, other valving and/or flow dimensions can also be employed Airflow from the first chamber 72 into the second chamber 101 (via the passage 106) serves to drive the drive mechanism 82. In particular, airflow within the second chamber 101 acts upon the lobe assemblies 140, 142 (the lobe assembly 142 being hidden in FIG. 7A), causing operation thereof as a rotary positive blower. In general terms, and with additional reference to FIG. 5B, airflow through the second chamber 101 causes the lobe bodies 150, 162 to rotate, with airflow flowing through or between the lobe bodies 150, 162, and then to the outlet opening 108. In this regard, the lobe assemblies 140, 142 operate as a roots blower, creating a pressure drop across the second chamber 101. As shown in FIG. 7B, when the control ports 78 are periodically "covered" by the valve plate segments 132, 134, airflow through the control ports 78 is restricted, creating a resistance to flow, or back pressure within the patient inlet 68. This resistance to flow/back pressure occurs periodically (i.e., when the valve plate segments 132, 134 are rotated away from the control ports 78, back pressure within the patient inlet 68 is released through the control ports 78). As a result, a desired oscillatory PEP effect is created. Notably, the lobe assemblies 140, 142 continue to rotate even as airflow through the passage 106 is periodically interrupted due to inertia. Along these same lines, the lobe assemblies 140, 142 can be configured to act as a fly wheel, thereby reducing sensitivity to an opening time of the control ports 78.

In some embodiments, dimensional characteristics of the drive mechanism 82 are correlated with the valve body 80 and the control port(s) 78 such that a flow rate of 10 lpm at 100 Pa, the valve body 80 generates approximately 15 pulses per second at the control ports 78, with the pressure pulses at approximately 3,000 Pa. At flow rates above 10 lpm, the valve structure 172 will open and may flutter to maintain inlet pressure to the drive mechanism 82. The fourth relief port arrangement 98 can be configured set to flow up to 20 lpm at 100 Pa (e.g., when the valve structure 172 is "open") so as to keep the back pressure and speed approximately consistent from 10 lpm to 30 lpm. Alternatively, however, the therapy device 60 can be configured to exhibit other operational characteristics.

Figure 8A:
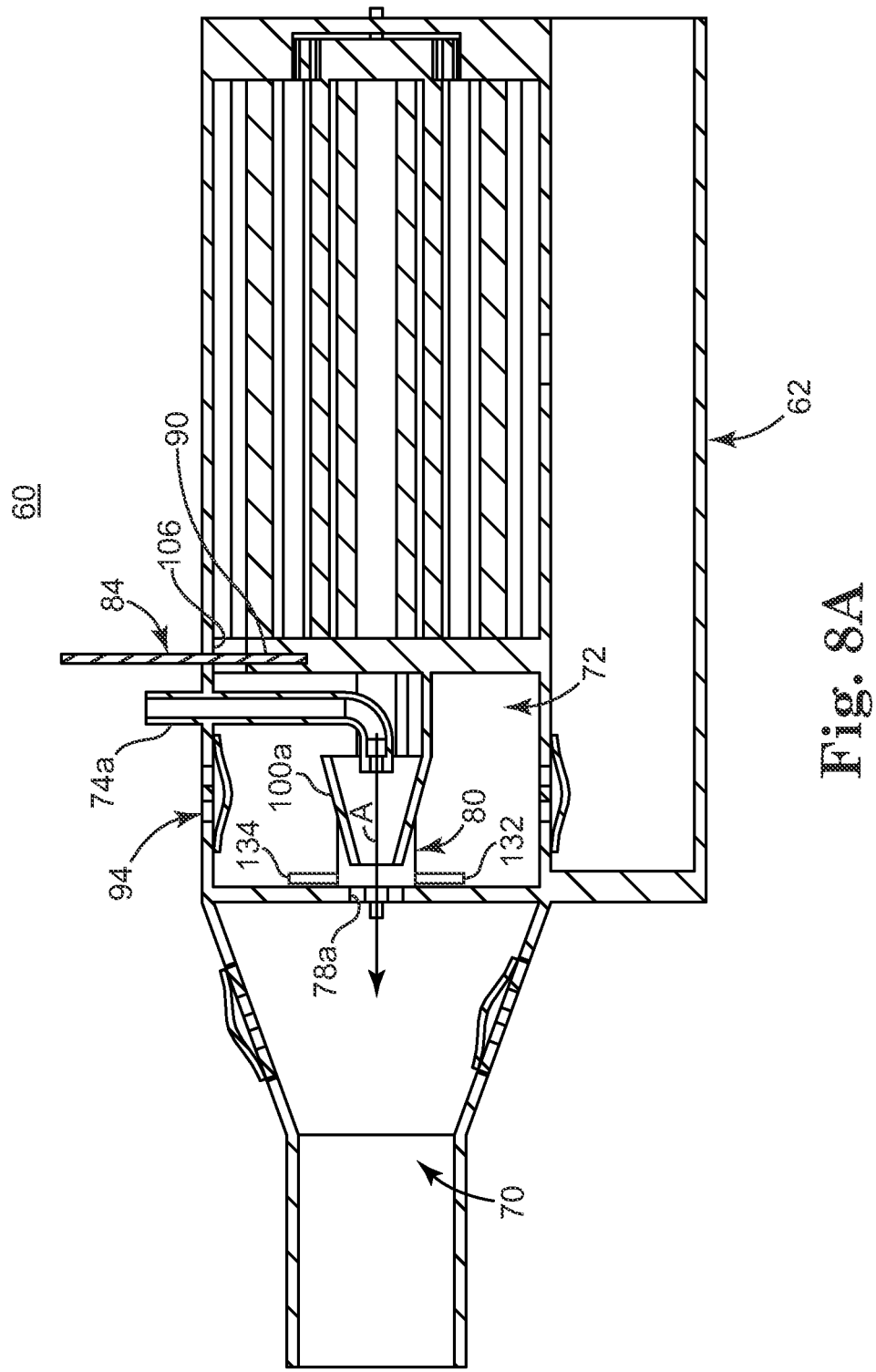
FIGS. 8A-8C illustrate use of the device of FIG. 2 in an active mode.

With reference to FIGS. 2 and 8A, in the active mode of operation, the control means 84 is operated to fluidly "close" the passage 106 (e.g., the tab 166 is fully inserted into the slot 90). Further, the inlets 74a-74c are fluidly connected to the pressurized fluid source 48 (FIG. 1). For example, in some embodiments, a flow diverter assembly (not shown) can be employed to fluidly connect a single pressurized fluid source (e.g., positive pressure gas such as air, oxygen, etc.) to each of the supply inlets 74a-74c; alternatively, two or more fluid sources can be provided. Regardless, air, oxygen, or other gas is forced or directed into the supply inlets 74a-74c. With specific reference to FIG. 8A, fluid flow into the first patient supply inlet 74a is illustrated with an arrow A and is directed by the nozzle 100a toward the control port 78a. Ambient air is entrained into the flow generated by the nozzle 100a via the second relief port arrangement 94 as previously described. In instances where the valve body 80, and in particular the valve plate segments 132, 134, does not otherwise obstruct the control port 78a (relative to the nozzle 100a), airflow continues through the control port 78a and into the patient inlet 68. Though hidden in the view of FIG. 8A, a similar relationship is established between the second patient supply inlet 74b/second nozzle 100b and the second control port 78a.

Figure 8B:
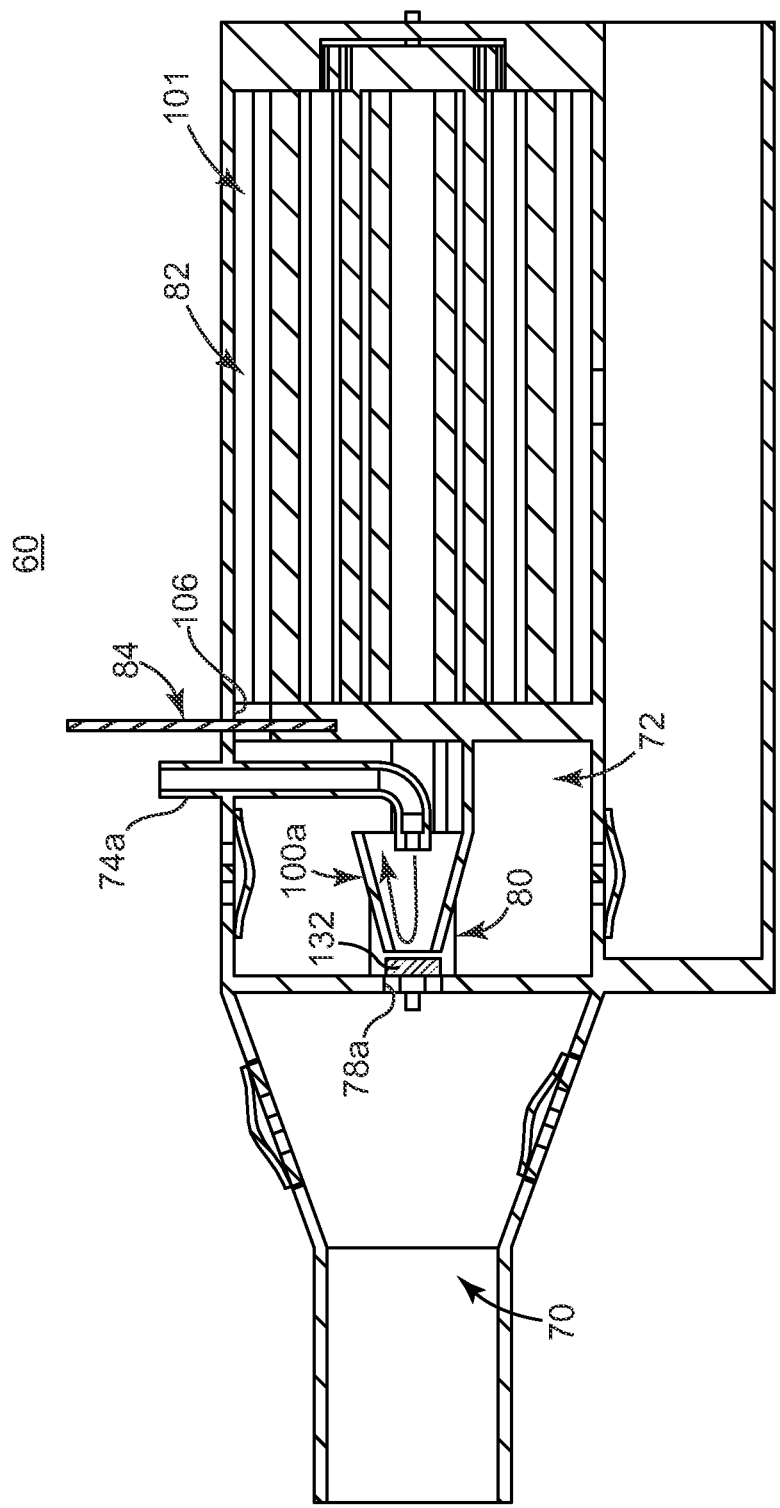

Conversely, and as shown in FIG. 8B, when the control port 78a and the control port 78b (hidden in FIG. 8B) are obstructed or "closed" via the valve plate segments 132, 134, airflow from the nozzles 100a, 100b to the patient inlet 68 is effectively stopped (it being understood that in the view of FIG. 8B, only the first patient supply inlet 74a/nozzle 100a, the first control port 78a, and the first valve plate segment 132 are visible). Once again, the drive mechanism 82 operates to continually rotate the valve body 80 relative to the control ports 78a, 78b, such that positive airflow from the supply inlets 74 to the patient inlet 68 is "chopped" or oscillated so as to establish a CHFO treatment during the patient's breathing cycle (including at least the patient's inspiratory phase).

Figure 8C:
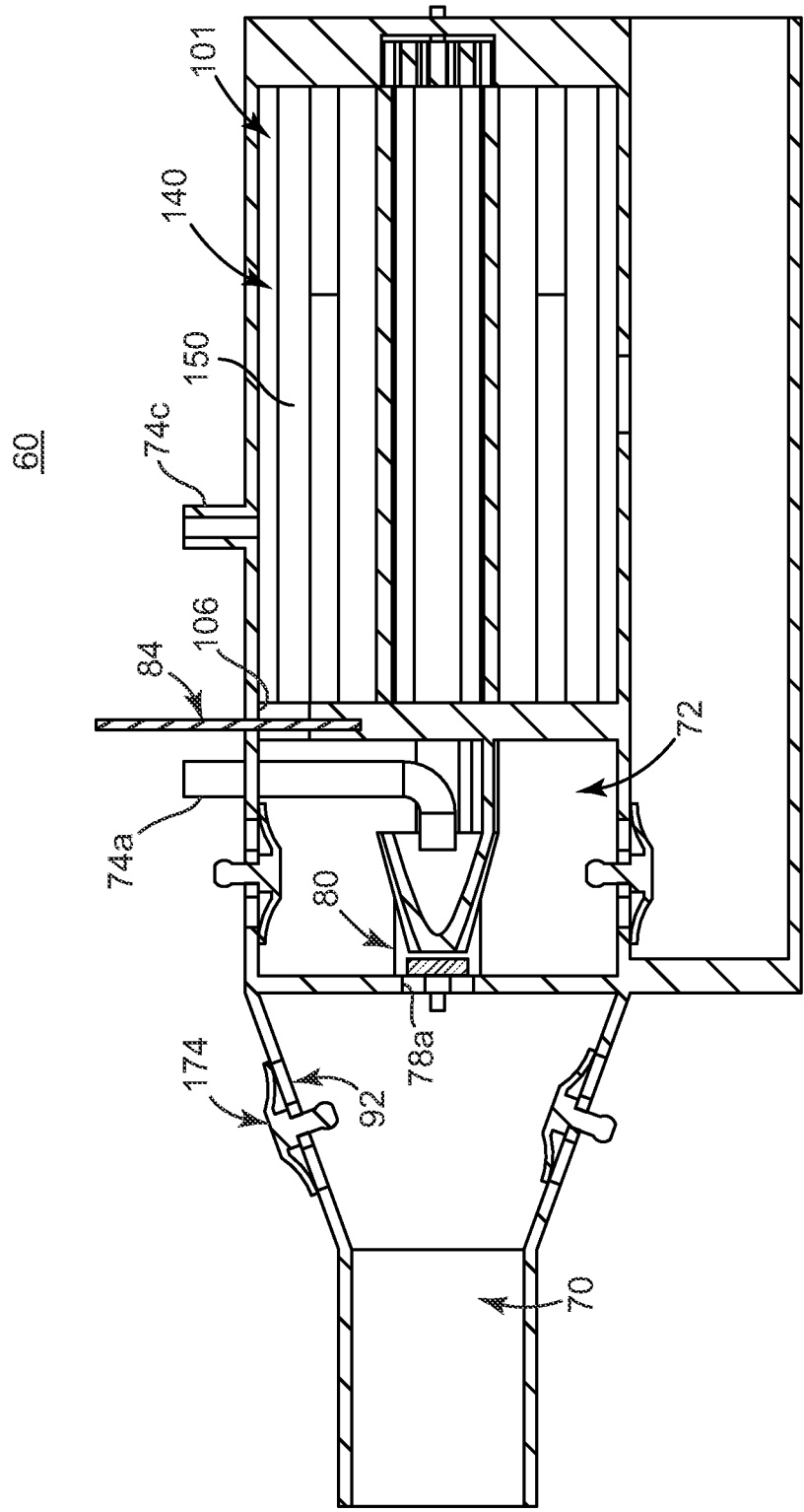

To better ensure positive airflow toward the patient inlet 68 (and thus the patient), the control means 84 closes the passage 106 such that all air within the first chamber 72 is forced through the control ports 78. In this regard, the drive mechanism 82, and in particular the lobe assemblies 140, 142, are acted upon and driven via fluid flow through the drive supply inlet 74c as shown in FIG. 8C. In particular, forced fluid flow from the pressurized fluid source 48 (FIG. 1) enters the second chamber 101 via the drive supply inlet 74c and acts upon the lobe bodies 150, 162 as previously described. In other words, operation of the therapy device 60 in the active mode is independent of the patient's breathing. Further, during the expiratory phase of the patient's breathing cycle, pulsed gas flow from the nozzles 100a, 100b to the patient inlet 70 continues, creating an oscillatory PEP effect. As a point of reference, to minimize possible occurrences of stacked breaths, exhaled air from the patient can be exhausted from the patient inlet 70 via the first relief port arrangement 92. For example, a one-way valve structure 174 can be assembled to the relief port arrangement 92, operating (in the active mode) to permit airflow through the relief port arrangement 92 to occur only outwardly from the patient inlet 70, thus freely permitting exhalation during periods when the control ports 78a, 78b are blocked. An additional control mechanism (not shown) can further be provided that fluidly "closes" the relief port arrangement 92/valve structure 174 when the device 60 operates in the passive mode described above (i.e., all exhaled air from the patient passes through the control ports 78a, 78b). Alternatively, the device 60 can include other features (not shown) that facilitate exhausting of exhaled air from the patient inlet 70, and/or the first relief port arrangement 92 can be eliminated. Along these same lines, in the active mode, the third relief port arrangement 96/valve structure 170 can be permanently "closed" such that all inspiratory airflow is provided via the control ports 78a, 78b.

While the device 60 has been described above as providing CHFO therapy via essentially identical fluid flow from both of the patient inlets 74a, 74b, in other embodiments, the device 60 can be configured to provide a user with the ability to select or change the level of CHFO. For example, a mechanism (not shown) can be provided that causes fluid flow from one of the supply inlets 74a or 74b to not occur (where a lower level of CHFO is desired) and continuously "blocks" the corresponding control port 78a or 78b (e.g., the supply inlet 74a or 74b can be fluidly uncoupled from the pressure source, and a closure means (not shown) actuated relative to the corresponding control port 78a or 78b). Even further, the device 60 can be modified to incorporate three of the supply inlets/nozzles 74/100 and three of the control ports 78, with respective ones of the supply inlets/nozzles 74/100 being selectively activated/deactivated and the corresponding control ports 78 being selectively blocked so as to provide three levels of CHFO. Alternatively, the three supply inlets 74 can merge into a single nozzle 100, again allowing a user to select a desired CHFO level by "activating" a desired number of the supply inlets 74.

In addition to the passive (e.g., oscillatory PEP) and active (e.g., CHFO) modes described above, the therapy device 60 can further be configured to provide additional forms of respiratory therapy. For example, and returning to FIG. 1, the nebulizer 50 (FIG. 1) can be fluidly connected to (and optionally disconnected from) the patient inlet 36 for providing aerosolized medication and other treatment to the patient. With respect to the exemplary therapy device 60 of FIG. 2, then, the housing 62 can form or include an additional port (not shown) to which the nebulizer 50 is fluidly connected. In some embodiments, the nebulizer port is provided at or adjacent the mouthpiece 86 such that nebulizer flow is directly to the patient and is not acted upon by the interrupter valve assembly 64. Alternatively, the nebulizer port can be formed at the end plate 69, or at any other point along the housing between the end plate 69 and the mouthpiece 86. In other embodiments, one or more of the inlet ports 74a-74c can serve as a nebulizer port. In yet other embodiments, the nebulizer 50 can include a connection piece that is physically attached to the mouthpiece 86. Regardless, nebulized air can be provided during operation of the interrupter valve assembly 64 (in either passive or active modes). Alternatively, the respiratory therapy device 60 can be configured such that when in a nebulizer mode of operation, the interrupter valve assembly 64 is temporarily "locked" such that the valve body 80 does not rotate and the valve plate segments 132, 134 do not obstruct the control ports 78.

Alternatively or in addition, the therapy device 60 can be adapted to provide CPAP therapy (with or without simultaneous aerosolized drug treatment) when desired by fluidly connecting the pressurized fluid source 48 (FIG. 1) to one or both of the patient supply inlets 74a, 74b, while again "locking" the interrupter valve assembly 64. In particular, the interrupter valve assembly 64 is held in a locked position whereby the valve body 80 does not rotate, and the control ports 78a, 78b are not obstructed by the valve plate segments 132, 134 such that positive airflow to the patient occurs continuously. For example, and with reference to FIGS. 5A and 8A, one or more mechanisms can be provided that, when actuated, decouple the first drive shaft 152 from the first lobe body 150 (so that the drive shaft 152 does not rotate with rotation of the lobe body 150), and retains the valve body 80 in the "open" position of FIG. 8A (e.g., magnet, body that captures one or both of the valve plate segments 132, 134, etc.). Along these same lines, the device 60 can be modified to deliver a constant, baseline pressure CPAP therapy with or without simultaneous CHFO treatment. For example, the interrupter valve assembly 64 can be configured such that the valve body 80 only affects fluid flow from the first supply inlet 74a, whereas fluid flow from second supply inlet 74b is continuously supplied to the patient inlet 70. With this approach, the second supply inlet 74b provides a specific, baseline pressure (e.g., 5 cm water) as CPAP therapy, whereas the interrupter valve assembly 64 acts upon fluid flow from the first supply inlet 74a in creating a CHFO effect as described above. In this regard, the interrupter valve assembly 64 can be "locked" as described above during periods where CHFO therapy is not desired. In yet another, related embodiment, the device 60 can be configured to provide a varying, selectable level of CPAP. For example, a mechanism (not shown) can be included that partially restricts (on a continuous basis) the inlet end 114 (FIG. 4A) and/or the exit end 116 (FIG. 4A) of the nozzle(s) 100, or the corresponding supply inlet 74, a desired extent (thus dictating a level of delivered CPAP). Alternatively, a controlled leak can be introduced into the system (e.g., a relief port arrangement and corresponding control valve that exhausts to ambient can be provided at one or both of the patient inlet 70 and/or the first chamber 72). Even further, one or both of the patient inlets 74 can be selectively "activated" to provide CPAP therapy as described above (it being understood that the level of CPAP will be greater where fluid flow is provided through both of the patient inlets 74 as compared to just one of the patient inlets 74).

In yet other embodiments, the device can be configured to optionally provide a continuous PEP therapy in the passive mode. In particular, the interrupter valve assembly 64 is "locked" in an open state as previously described, and the supply inlets 74 are disconnected from the pressurized fluid source 48 (FIG. 1). As a result, the control ports 78 serve as flow restrictors to exhaled air, thus creating or delivering the PEP effect.

Regardless of whether the additional modes of operation are provided, the therapy device 60 provides a marked advantage over previous designs by being operable in both the passive and active modes. For example, a patient can be given the therapy device 60 immediately following surgery, admission to the caregiver's facility (e.g., hospital), etc., and instructed to use the therapy device 60 in the passive mode. This allows the patient to begin receiving oscillatory PEP therapy treatments immediately. Subsequently, upon observation (x-rays, breath sounds, blood analysis, etc.) by the caregiver that a more aggressive oscillatory therapy is required to aide with airway clearance and/or airway expansion, the therapy device 60 can then be connected to a pressurized source (e.g., the pressurized fluid source 48 of FIG. 1) and switched to the active mode. Following the active treatment, the therapist can leave the therapy device 60 with a patient to allow the patient to continue the passive therapy without the caregiver needing to be present. In other words, the patient can continue to use the same therapy device 60 at virtually any location away from the caregiver's facility.

Although the respiratory therapy device 60 has been described as providing both passive and active modes of operation, in other embodiments in accordance with the present disclosure, similar principles of operation can be employed in a passive-only or oscillatory PEP device (that otherwise interacts with the patient's breathing). For example, an alternative embodiment respiratory therapy device 186 is shown in exploded form in FIG. 9. The therapy device 186 is similar in many respects to the respiratory therapy device 60 (FIG. 2) previously described, and includes a housing 188 (referenced generally) and an interrupter valve assembly 190. The housing 188 includes a leading section 192, an intermediate plate 194, a trailing section 196, and an end plate 198. The interrupter valve assembly 190 includes one or more control ports 200a, 200b, a valve body 202, and a drive mechanism 204. As described in greater detail below, the drive mechanism 204 rotates the valve body 202 in response to exhaled airflow from the patient to periodically obstruct or close the control ports 200a, 200b.

The leading section 192 of the housing 188 includes a tapered mouthpiece 208, and forms or defines a patient inlet 210, whereas the trailing section 196 forms a first chamber 212. The plate 194 separates the patient inlet 210 and the first chamber 212, and forms the one or more control ports 200a, 200b. As with previous embodiments, while two of the control ports 200a, 200b are shown, any other number, either lesser or greater, is also acceptable. Regardless, fluid flow between the patient inlet 210 and the first chamber 212 is via the control port(s) 200a, 200b.

Figure 9:
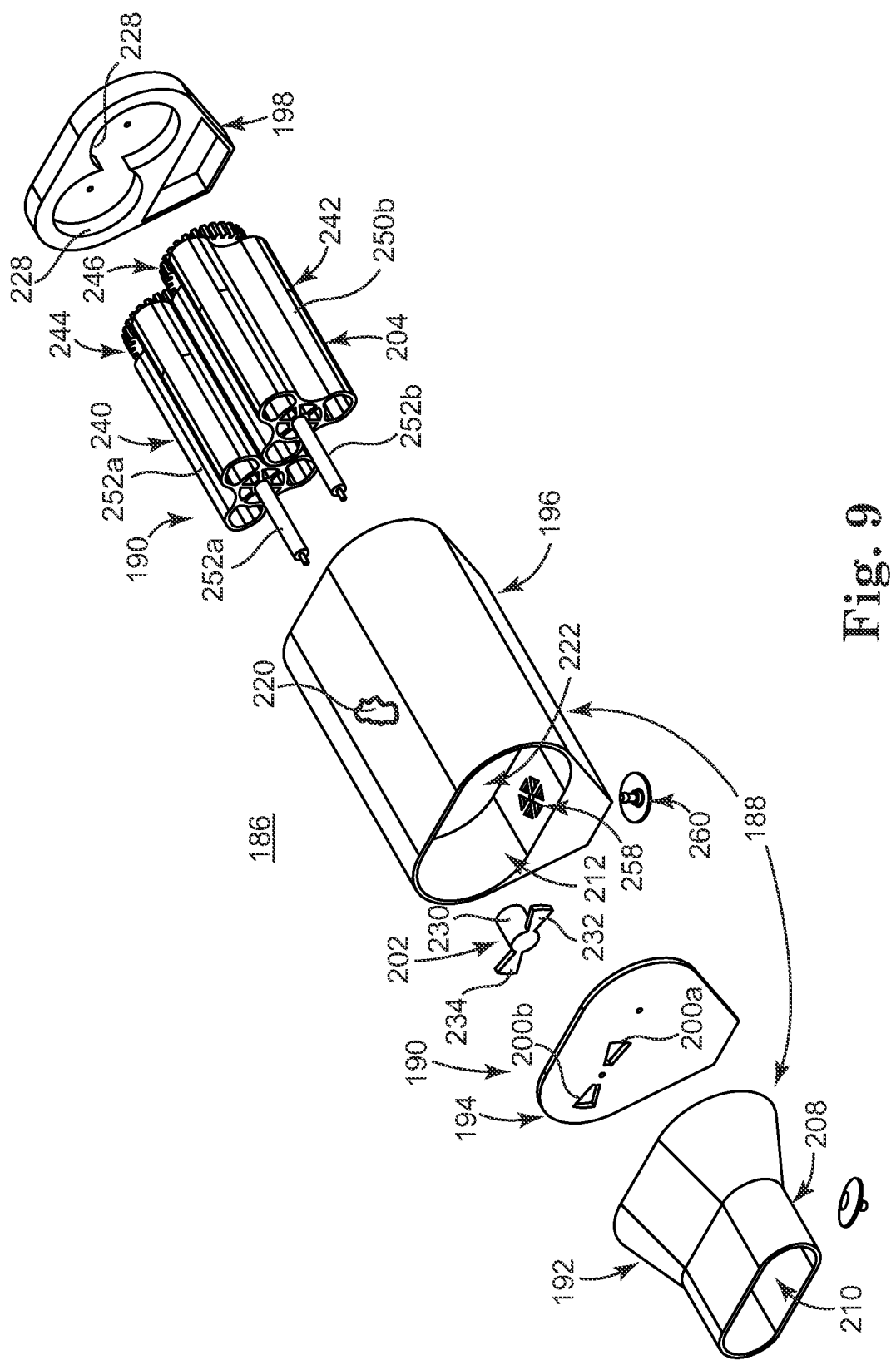
FIG. 9 is an exploded, perspective view of an alternative respiratory therapy device in accordance with principles of the present invention.
Figure 10:
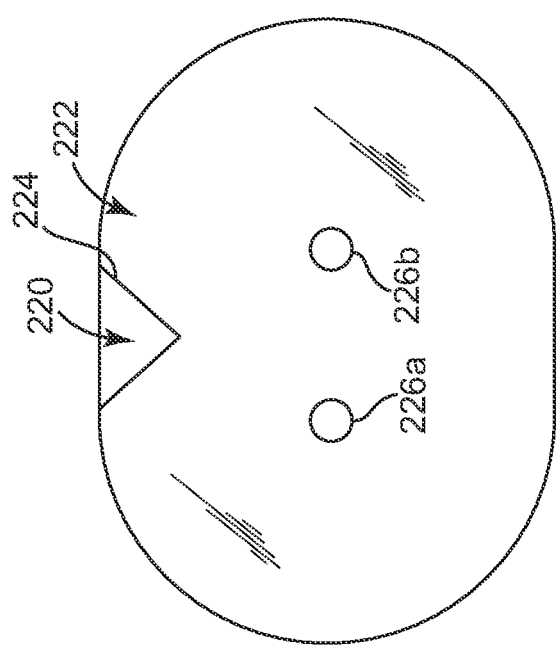
FIG. 10 is a front, plan view of a trailing housing portion of the device of FIG. 9.

The trailing section 196 further forms a second chamber 220 and, in some embodiments, an exhaust chamber (hidden in the view of FIG. 9). The second chamber 220 is sized to receive a corresponding portion of the drive mechanism 204 as described below, and is fluidly isolated from the first chamber 212 by an intermediate wall 222. In this regard, and as best shown in FIG. 10, the intermediate wall 222 forms a passage 224 through which fluid flow from the first chamber 212 (FIG. 9) to the second chamber 220 (referenced generally in FIG. 10) can occur. In addition, the intermediate wall 222 defines first and second holes 226a, 226b sized to receive corresponding components of the drive mechanism 204 as described below. Finally, and returning to FIG. 9, the end plate 198 is adapted for assembly to the trailing section 196, and serves to close the second chamber 220. As shown, the end plate 198 can form grooves 228 sized to rotatably retain corresponding components of the drive mechanism 204 as described below.

The valve body 202 is similar to the valve body 80 (FIG. 2) previously described, and in some embodiments includes a base 230, a first valve plate segment 232, and a second valve plate segment 234. The valve plate segments 232, 234 are shaped and sized in accordance with the control ports 200a, 200b such that when aligned, the valve plate segments 232, 234 can simultaneously obstruct or "block" the control ports 200a, 200b. Regardless, the valve plate segments 232, 234 extend radially from the base 230 that is otherwise configured for affixment to a corresponding component of the drive mechanism 204.

The drive mechanism 204 is akin to a reverse roots blower assembly, and includes first and second lobe assemblies 240, 242, and first and second gears 244, 246. The lobe assemblies 240, 242 each include a lobe body 250a, 250b coaxially mounted to, or integrally formed with, a shaft 252a, 252b, respectively. The shafts 252a, 252b, in turn, are assembled to, or integrally formed with, a respective one of the gears 244 or 246, with the valve body 202 being mounted to the shaft 252a of the first lobe assembly 240. Upon final assembly, the lobe bodies 250a, 250b interface with one another in a meshed fashion, as do the gears 244, 246.

Figure 11:
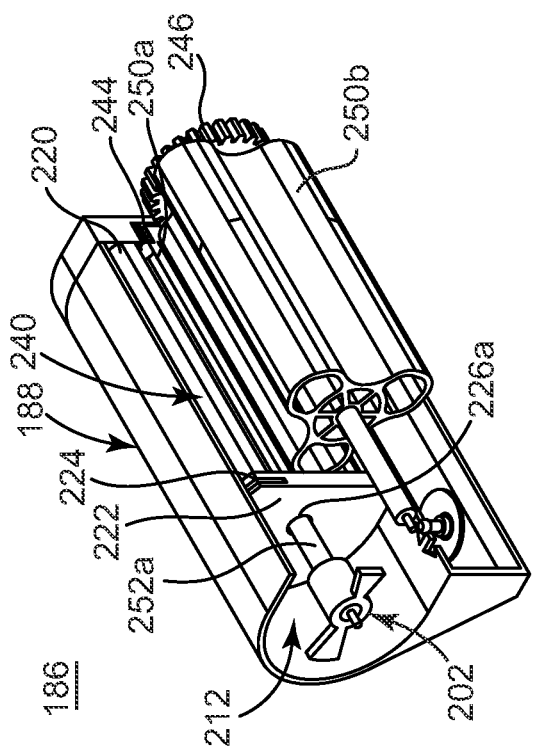
FIG. 11 is a perspective, cutaway view of a portion of the device of FIG. 9 upon final assembly.

With initial reference to FIG. 11, assembly of the respiratory therapy device 186 includes placement of the lobe bodies 250a, 250b/gears 244, 246 within the second chamber 220 defined by the housing 188. As shown, the shafts 252a, 252b extend from the second chamber 220 and into the first chamber 212. The valve body 202 is assembled to the shaft 252a of the first lobe assembly 240 (or the shaft 252b of the second lobe assembly 242), and is thus located with the first chamber 212. The intermediate wall 222 serves to fluidly isolate the first and second chambers 212, 220, except at the passage 224.

The intermediate plate 194 and the leading section 192 are then assembled to the trailing section 196 as shown in FIG. 12 (it being understood that in some embodiments, the leading section 192 and the plate 194 can be integrally formed). In particular, upon assembly of the leading section 192/plate 194, the valve body 202 is associated with the control port(s) 200a, 200b. For example, the valve body 202 is positioned such that the valve plate segments 232, 234 selectively align with respective ones of the control ports 200a, 200b with rotation of the valve body 202. FIG. 13A illustrates the therapy device 186 upon final assembly.

A relationship of the various components of the therapy device 186 are best shown in the cross-sectional view of FIG. 13B. Once again, the patient inlet 210 is fluidly connected to the first chamber 212 via the control ports 200a, 200b (it being understood that only the first control port 200a is visible in FIG. 13B). The valve body 202 is maintained in the first chamber 212 such that the valve plate segments 232, 234 (it being understood that only the first valve plate segment 232 is seen in the view of FIG. 13B) are selectively aligned with the control ports 200a, 200b so as to obstruct fluid flow between the patient inlet 210 and the first chamber 212. The first chamber 212 is fluidly connected to the second chamber 220 via the passage 224. The second chamber 220 maintains the lobe assemblies 240, 242 (it being understood that only the first lobe assembly 240 is visible in the view of FIG. 13B). Further, the second chamber 220 is fluidly connected to an exhaust chamber 254 via an outlet opening 256. The first chamber 212 is also fluidly connected to the exhaust chamber 254 via a relief port arrangement 258 to which a valve assembly 260 (e.g., a one-way, umbrella valve) is assembled. Finally, the exhaust chamber 254 is open to ambient at an exhaust outlet 262. As a point of reference, the exhaust chamber 254 serves to minimize the opportunity for one or both of the outlet opening 256 and/or the relief port arrangement 258 to inadvertently be obstructed during use. In other embodiments, however, the exhaust chamber 254 can be eliminated.

During use, operation of the interrupter valve assembly 190 includes the lobe assemblies 240, 242 rotating in response to airflow entering the second chamber 220 as described in greater detail below. Rotation of the first lobe assembly 240 causes the valve body 202 to similarly rotate, thus periodically moving the valve plate segments 232, 234 into and out of alignment with corresponding ones of the control ports 200a, 200b, creating an oscillatory PEP effect in the patient inlet 210 as the patient exhales.

Figure 14B:
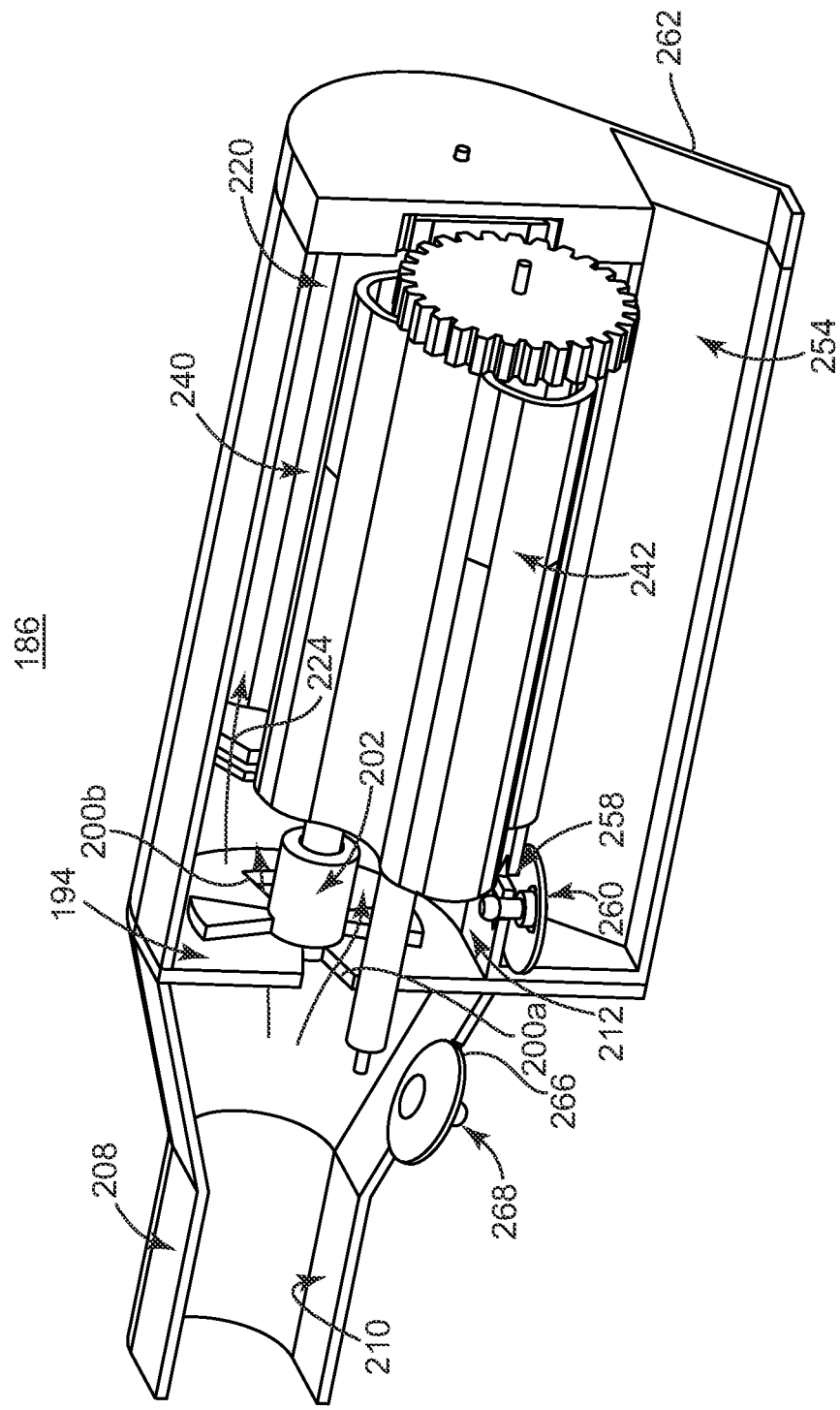

For example, with reference to FIGS. 14A and 14B, the mouthpiece 208 (or other component attached to the mouthpiece 208, such as a nebulizer connector) is placed in the patient's mouth (not shown) and the patient performs a breathing cycle through the patient inlet 210. During the inspiratory phase, ambient air readily enters the patient inlet 210 via a relief port arrangement 266, the flow through which is controlled by a one-way valve structure 268 (such as an umbrella valve). During the expiratory phase, exhaled air from the patient is directed through the patient inlet 210 and toward the plate 194. With the valve body 202 arrangement relative to the control ports 200a, 200b of FIGS. 14A and 14B, the valve plate segments 232, 234 are not aligned with the control ports 200a, 200b such that the patient's exhaled air flows from the patient inlet 210 through the control ports 200a, 200b, and into the first chamber 212. This flow pattern is represented by arrows in FIGS. 14A and 14B. Airflow within the first chamber 212 flows through the passage 224 and into the second chamber 220, and then interacts with the lobe assemblies 240, 242. In particular, airflow within the second chamber 220 causes the lobe assemblies 240, 242 to rotate, with the airflow then exiting the second chamber 220 (at the outlet opening 256 of FIG. 14A) to the exhaust chamber 254. Air within the exhaust chamber 254 is then exhausted to the environment via the exhaust outlet 262.

As shown in FIGS. 14A and 14B, the valve structure 260 controls fluid flow through the relief port arrangement 258 between the first chamber 212 and the exhaust chamber 254. In some embodiments, the valve structure 260 is a one-way bypass valve having a predetermined opening or bypass pressure. With this in mind, so long as airflow within the first chamber 212 is below the opening pressure of the valve structure 260, the valve structure 260 remains closed, such that all air flows into the second chamber 220 as described above. Where, however, pressure within the first chamber 212 is above the opening pressure of the valve structure 260, the valve structure 260 will "open" and allow a portion of the air within the first chamber 212 to bypass the second chamber 220/lobe assemblies 240, 242 and flow directly into the exhaust chamber 254 via the relief port arrangement 258. In this manner, the pressure drop across the second chamber 220 remains approximately equal to the opening pressure of the valve structure 260.

Figure 15B:
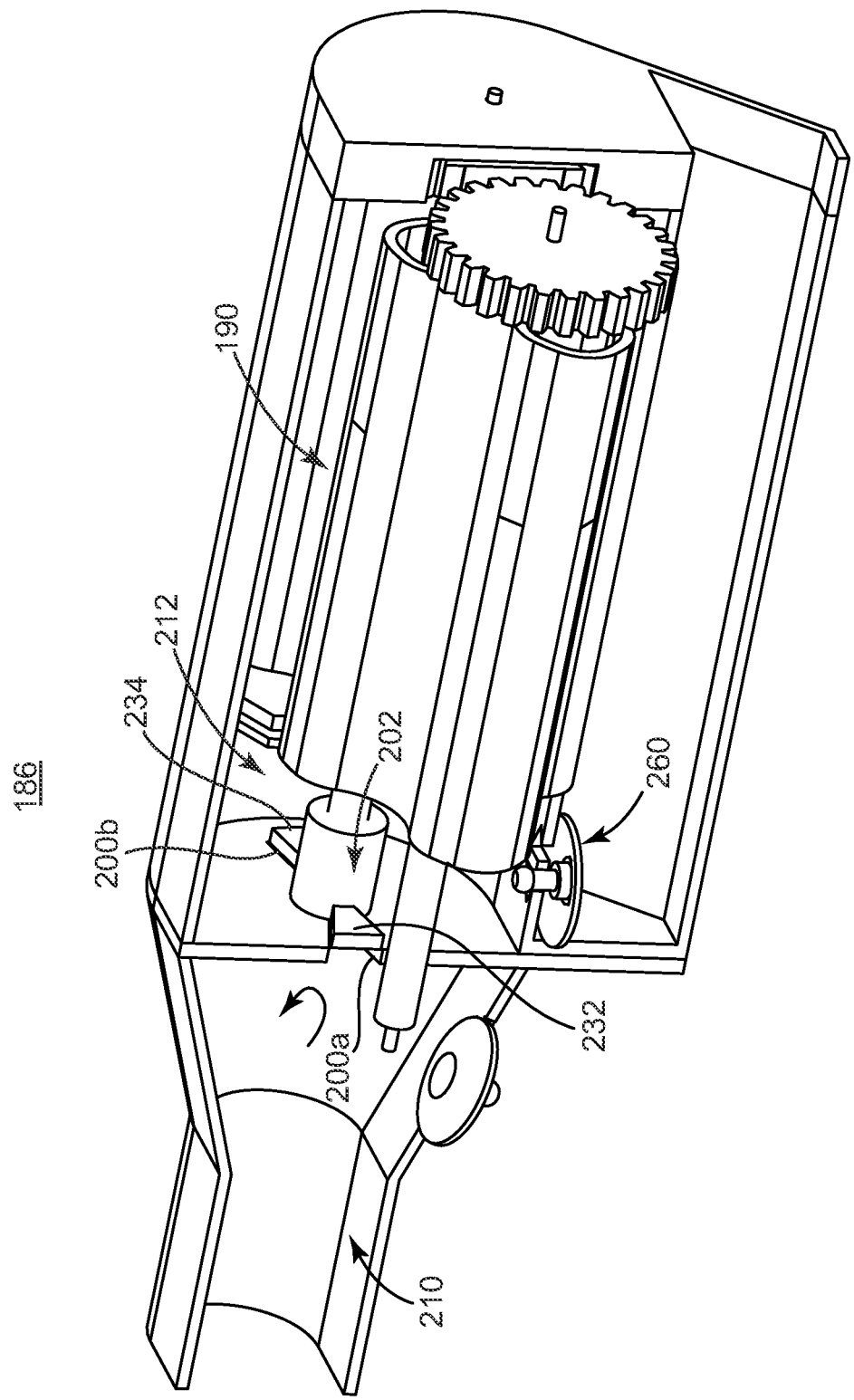

With rotation of the lobe assemblies 240, 242 in response to exhaled air entering the second chamber 220, the valve body 202 is caused to rotate. To account for instances in which the valve body 202 is initially aligned with control ports 200a, 200b (and thus may impede desired airflow into the second chamber 200 sufficient to initiate rotation of the lobe assembles 240, 242), means (not shown) can be provided by which a user can self-actuate movement of the valve body 282, a valved conduit can be provided that directly fluidly connects the patient inlet 210 with the second chamber 220, etc. Regardless, the valve plate segments 232, 234 will periodically be aligned with a respective one of the control ports 200a, 200b as shown, for example in FIGS. 15A and 15B. When so-aligned, exhaled air from the patient at the patient inlet 210 is substantially prevented from passing through the control ports 200a, 200b. As a result, a back pressure is generated within the patient inlet 210 that in turn is imparted upon the patient. This airflow is represented by arrows in FIGS. 15A and 15B. Because the valve body 202 is essentially continuously rotating in response to exhaled air, this back pressure is created on a periodic or oscillating basis. In other words, back pressure "pulses" are established within the patient inlet 210, with the back pressure being "released" from the patient inlet 210 as the valve plate segments 232, 234 move away from the control ports 200a, 200b. In some embodiments, the respiratory therapy device 186 is configured such that at an exhaled airflow rate of 10 lpm at 100 Pa drives the interrupter valve assembly 190 to create 15 pulses per second at the control ports 200a, 200b, with the pressure pulses being at approximately 3,000 Pa. At flow rates above 10 lpm, the valve structure 260 will open and may flutter to maintain inlet pressure to the drive mechanism 204. In related embodiments, the valve structure 260 is configured to establish flow of up to 20 lpm at 100 Pa, which substantially maintains the desired back pressure in the patient inlet 210 and a rotational speed constant in the range of 10 lpm-30 lpm. Alternatively, however, the respiratory therapy device 186 can be configured to exhibit a number of performance characteristics differing from those described above.

Another embodiment respiratory therapy device 280 is shown generally in FIG. 16, and is similar in construction to the device 60 (FIG. 2) previously described. In particular, the device 280 includes a housing 282 and an interrupter valve assembly 284. The housing 282 is akin to the housing 62 (FIG. 2 previously described), and generally defines a patient inlet 286, a first chamber 288, a second chamber 290, and supply inlets 292 (one of which is shown in FIG. 16). As compared to the housing 62, the first and second chambers 288, 290 are permanently fluidly isolated from one another (i.e., the notch 106 (FIG. 4A) is not provided). The interrupter valve assembly 284 is akin to the interrupter valve assembly 64 (FIG. 2), and includes control ports 294 (one of which is shown) between the patient inlet 286 and the first chamber 288, a valve body 296 and a drive mechanism 298.

In general terms, the device 280 operates as an "active-only" configuration, whereby the ability to disconnect the pressurized fluid source 48 (FIG. 1) from the supply inlets 292 and perform a manual, passive oscillatory PEP therapy is not provided. However, CHFO (and optionally CPAP) therapy is achieved as previously described in a manner representing a marked improvement over existing CHFO devices. For example, the device 280 can be directly connected to virtually any pressurized fluid source and still provide CHFO therapy (i.e., a separate "driver" unit is not required as the device 280 itself modifies incoming, constant pressure fluid flow into oscillatory flow to the patient). Similarly, and unlike existing designs, the device 280 can be modified as previously described with respect to the device 60 (FIG. 2) to provide additional modes of operation such as delivery of aerosolized medication, CPAP, etc., separately or simultaneously with CHFO treatment.

Figure 17:
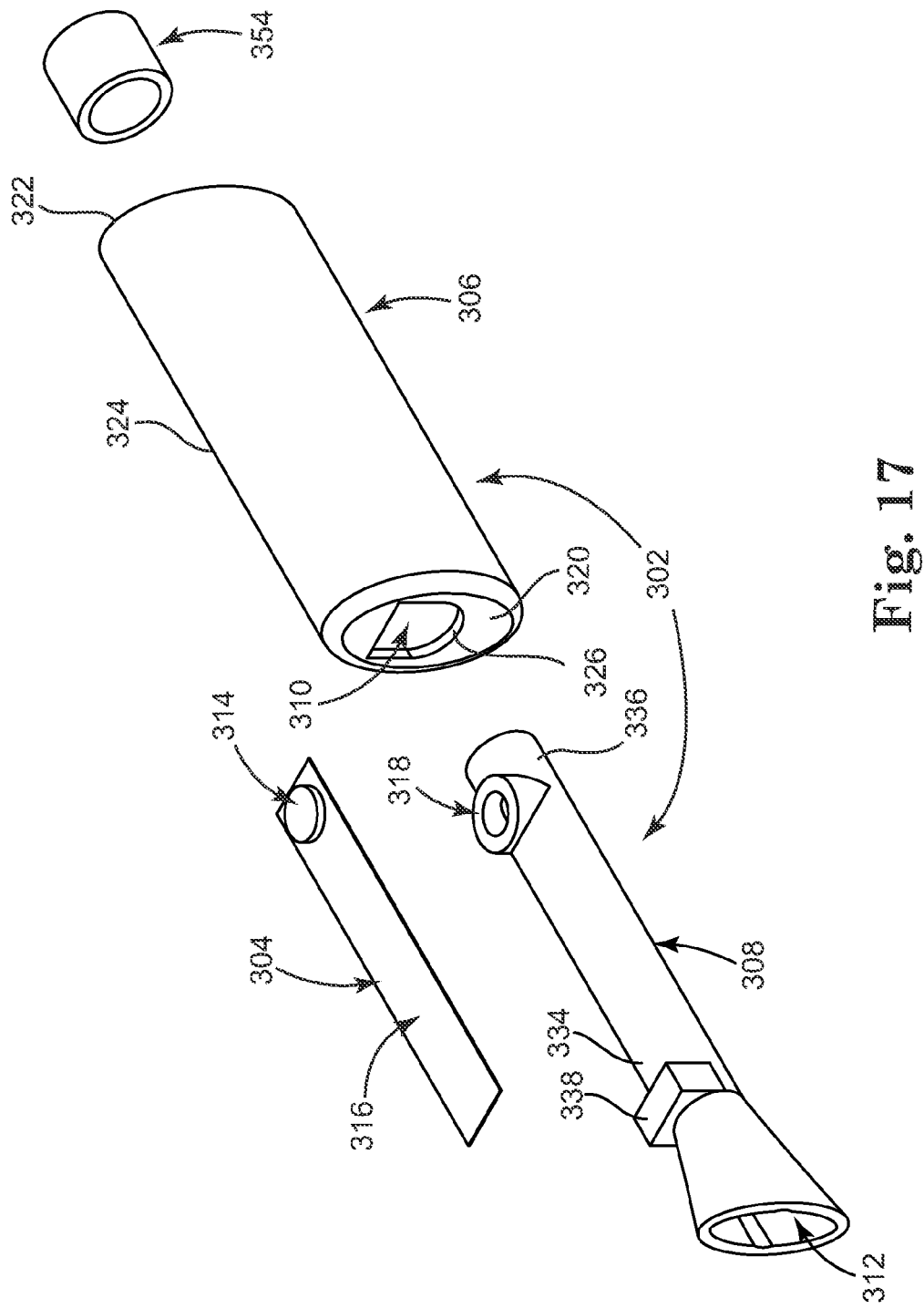
FIG. 17 is an exploded, perspective view of another embodiment respiratory therapy device in accordance with principles of the present disclosure.

Yet another alternative embodiment respiratory therapy device 300 in accordance with principles of the present disclosure is shown in FIG. 17. The respiratory therapy device 300 includes a housing 302 (referenced generally) and an interrupter valve assembly 304. The housing 302 generally includes an outer housing portion 306 and an inner housing portion 308 that combine to define a first chamber 310 (referenced generally in FIG. 17 relative to the outer housing portion 306) and a patient inlet 312. The interrupter valve assembly 304 includes a valve body 314, a drive mechanism 316 and a control port 318. Details on the various components are provided below. In general terms, however, upon final assembly, the valve body 314 is selectively associated with the control port 318 (otherwise formed by the inner housing portion 308). The drive mechanism 316 selectively controls movement of the valve body 314 toward and away from the control port 318, for example in response to air exhaled by a patient during an expiratory phase of a breathing cycle, so as to establish a periodic back pressure within the patient inlet 312. This back pressure, in turn, provides an oscillatory PEP therapy to the patient.

The outer housing portion 306 is cylindrical and is sized to receive and maintain the inner portion 308. With additional reference to FIG. 18A, the outer housing portion 306 defines a first end 320, a second end 322, and an intermediate section 324. The first end 320 forms a passage 326 having a diameter or major dimension commensurate with that of a corresponding segment of the inner housing portion 308 such that upon assembly, the outer portion 306 and the inner portion 308 are fluidly sealed at the first end 320. Conversely, the second end 322 forms an opening 328 having a diameter or major dimension greater than a corresponding dimension of the inner housing portion 308 (and any other components attached thereto). With this configuration, the housing 302 is fluidly open to ambient at the second end 322. Finally, the intermediate segment 324 similarly defines a diameter or major dimension greater than that of the inner housing portion 308 so as to define the first chamber 310 between the inner housing portion 308 and the intermediate segment 304 of the outer housing portion 306.

The inner housing portion 308 includes, in some embodiments, a mouthpiece 330 and a tube 332. The mouthpiece 330 is adapted for convenient placement within a patient's mouth (or assembly to separate component (e.g., a nebulizer connection piece) that in turn is adapted for placement on a patient's mouth and thus can have, in some embodiments, an oval-like shape as shown in FIG. 17. Regardless, the mouthpiece 330 is connected to the tube 332, with the components combining to define the patient inlet 312 in the form of a continuous passage.

Figure 18A:
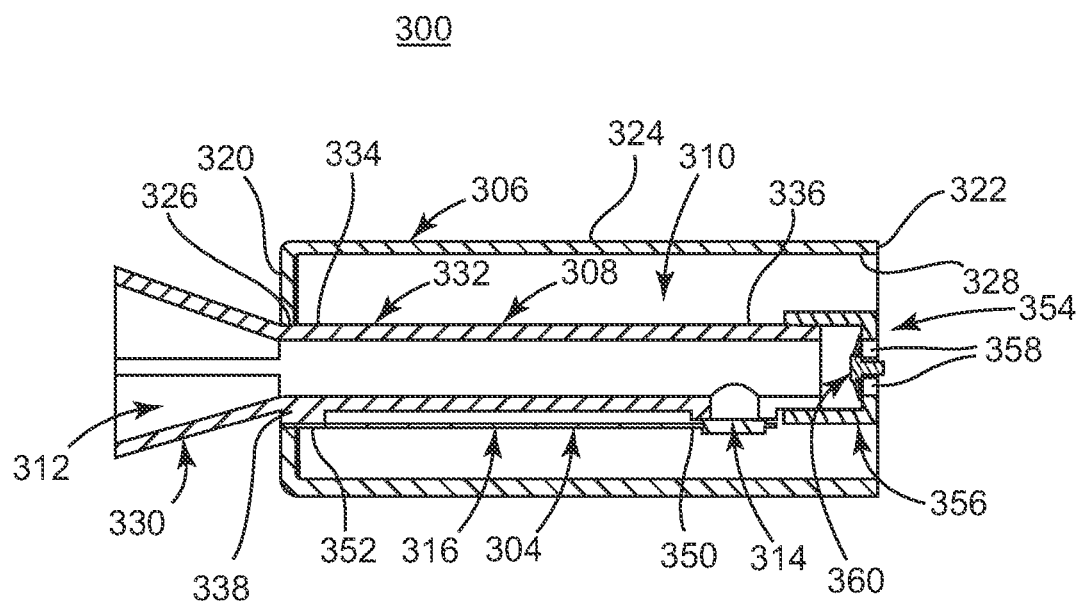
FIG. 18A is a longitudinal, cross-sectional view of the device of FIG. 17.

The tube 332 can assume a variety of different constructions, and includes or defines a proximal section 334 and a distal section 336. As shown in FIGS. 17 and 18A, the tube 332 includes an exterior shoulder 338 at the proximal section 334. As described in greater detail below, the shoulder 338 serves as a support or fulcrum for the drive mechanism 316 upon final assembly. Regardless, the control port 318 is formed at or adjacent the distal section 336, and establishes a fluid connection between the patient inlet 312 and the chamber 310. While shown as being part of the inner housing portion 308, then, the control port 318 is effectively part of the interrupter valve assembly 304.

Figure 18B:
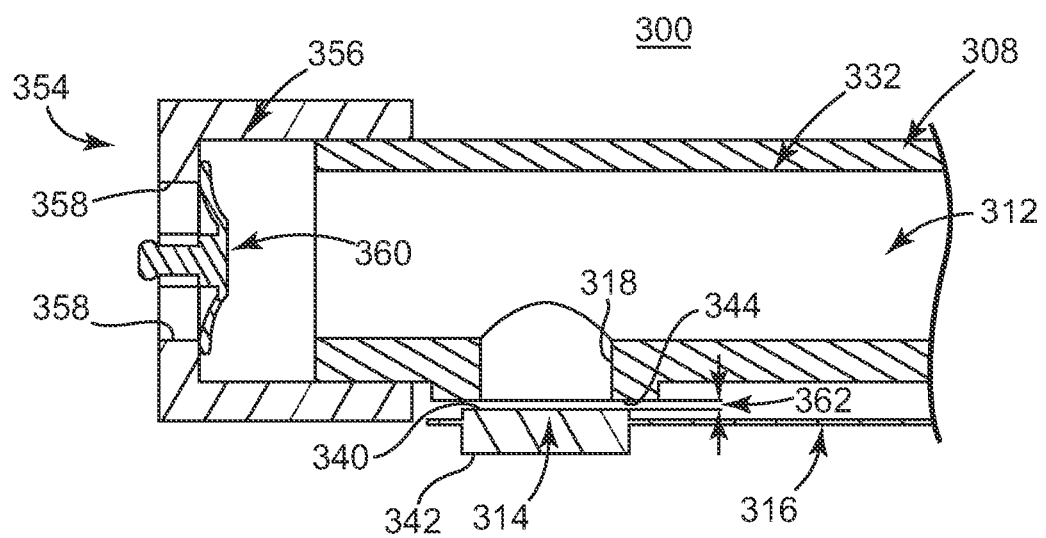
FIG. 18B is an enlarged view of a portion of FIG. 18A.

In addition to the control port 318, the interrupter valve assembly 304 includes the valve body 314 and the drive mechanism 316 as shown in FIG. 18A. The valve body 314 is, in some embodiments, a disc having a size and shape commensurate with a size and shape of the control port 318 (e.g., the valve body 314 can have the same shape dimensions as the control port 318, or can be larger or smaller than the control port 318). In some embodiments, the valve body disc 314 is sized to be slightly larger than the control port 318 to better achieve a more complete, selective obstruction of the control port 318. As best shown in FIG. 18B, the valve body disc 314 defines opposing first and second major surfaces 340, 342. With the one embodiment of FIG. 18B, the first surface 340 is flat. In other embodiments, however, the first surface 340 can assume a different shape, such as a hemispherical, conical, etc. Regardless, the first surface 340 is configured to generally mate with an exterior surface 344 of the inner housing portion 308 at which the control port 318 is defined.

Returning to FIG. 18A, the drive mechanism 316 is, in some embodiments, akin to a beam or other cantilevered-type device, and includes a leading end 350 and a trailing end 352. The leading end 350 is affixed to the valve body 314, whereas the trailing end 352 is adapted for assembly to the shoulder 338 of the inner housing portion 308. As described below, the drive mechanism 316 serves as a cantilever beam, and thus exhibits a desired stiffness for repeated, cyclical deflection. With this in mind, in some embodiments, the drive mechanism/beam 316 is formed of a steel spring, although other materials are also acceptable.

Finally, and as shown in FIGS. 17-18B, in some embodiments the respiratory therapy device 300 further includes a valve assembly 354 mounted to the inner housing portion 308. The valve assembly 354 can assume a variety of configurations, and can be akin to a one-way valve (e.g., flap or umbrella check valve). Thus, in some embodiments, the valve assembly 354 includes a frame 356 forming one or more apertures 358, along with a valve structure 360 that selectively obstructs the apertures 358. With this configuration, the valve assembly 354 permits ambient airflow into the tube 332/patient inlet 312, but restricts or prevents airflow outwardly from the tube 332/patient inlet 312.

Assembly of the respiratory therapy device 300 includes affixment of the valve assembly 354 to the distal section 336 of the inner housing portion 308. The trailing end 352 of the drive mechanism beam 316 is assembled (e.g., welded, bonded, etc.) to the shoulder 338 of the inner housing portion 308. As shown in FIG. 18A, upon assembly, the drive mechanism beam 316 is substantially straight and positions or aligns the valve body 314 with or "over" the control port 318.

In the neutral or resting state of FIG. 18A, then, the valve body 314 is in highly close proximity to the control port 318 so as to overtly restrict fluid flow through the control port 318. In some embodiments, and as best shown in FIG. 18B, the drive mechanism 316 is configured such that with the drive mechanism beam 316 in the neutral or resting state, a slight gap 362 is established between the valve body 314 and the exterior surface 344 of the inner housing portion 308 (otherwise defining the control port 318). A size of the gap 362 dictates a level of pressure drop within the patient inlet 312, with a dimension of the gap 362 having an inverse relationship to pressure drop within the patient inlet 312. With this in mind, in some embodiments, the gap 362 is less than 0.1 inch; and in other embodiments, less than 0.08 inch, and in yet other embodiments, is less than 0.04 inch. Alternatively, however, other dimensions are also acceptable, including elimination of the gap 362. It has surprisingly been found, for example, that where the control port 318 has a diameter on the order of 0.28 inch, the valve body 314 is a disc having a diameter on the order on 0.36 inch and a mass of 11.6 grams, where the drive mechanism beam 316 is formed of stainless steel and has a length on the order of 2.5 inches, a desired pressure drop/response of the respiratory therapy device 300 at 20 lpm flow rate is achieved with a dimension of the gap 362 being 0.011 inch. In particular, the respiratory therapy device 300 exhibited, in some embodiments, a pressure drop at 20 lpm flow rate in the range of 100-2,500 Pa.

During use, the therapy device 300 is provided to a patient along with instructions on desired orientation during use. In this regard, and in some embodiments, the therapy device 300 provides optimal performance when the control port 318 is spatially positioned at a "side" of the therapy device 300 as held by a patient. The oval or oblong shape of the mouthpiece 330 provides the patient with a visual clue of this desired orientation. While the therapy device 300 can operate when spatially oriented such that the control port 318 is facing "downwardly" (e.g., in the orientation of FIGS. 18A and 18B), or "upwardly," an upright orientation may better account for the effects of gravity during operation of the interrupter valve assembly 304.

Figure 19A:
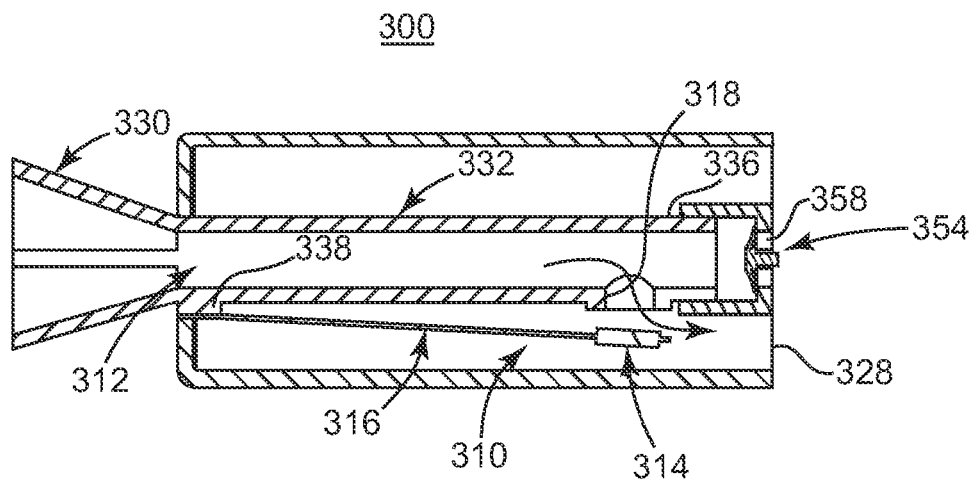
FIGS. 19A and 19B illustrate use of the device of FIG. 17.
Figure 19B:
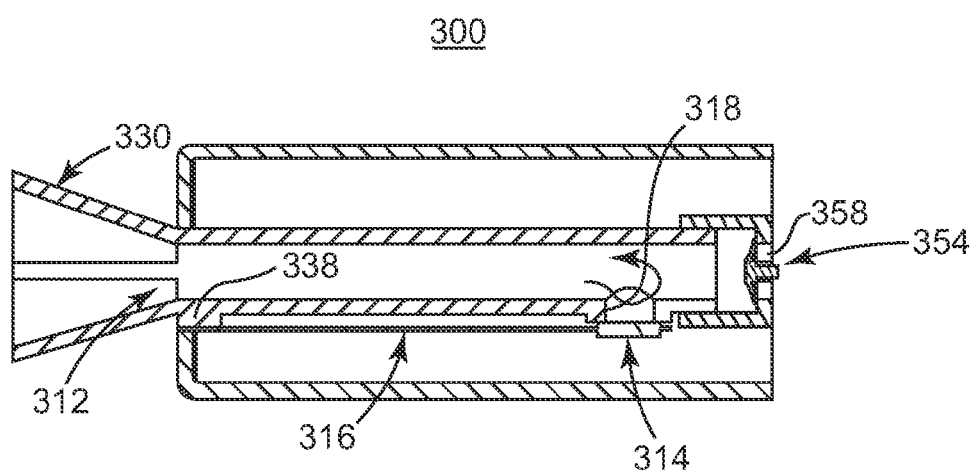

Notwithstanding the above, operation of the therapy device 300 is described with reference to FIGS. 19A and 19B with the therapy device 300 in an otherwise "downward" orientation for ease of illustration. It will be understood, however, that in other embodiments, the therapy device 300 is preferably spatially held by a patient such that the control port 318/valve body 314 is at a "side" of the therapy device as held (i.e., into the page of FIGS. 19A and 19B). With this in mind, following insertion of the mouthpiece 330 (or other component assembled to the mouthpiece 330) into the patient's mouth, the patient performs multiple breathing cycles. During the inspiratory phase, ambient airflow readily enters the patient inlet 312 via the aperture 358/valve assembly 354. During the expiratory phase, exhaled air from the patient is forced through the patient inlet 312 and toward the distal section 336 of the tube 332. The valve assembly 354 prevents exhaled air from exiting the tube 332 via the apertures 358. Instead, the exhaled airflow is directed to and through the control port 318; airflow exiting the control port 318 exerts a force onto the valve body 314 in a direction away from the tube 332 (and thus away from the control port 318), as shown by arrows in FIG. 19A. The drive mechanism beam 316 deflects to permit movement of the valve body 314 in response to the force, pivoting at the shoulder 338. As the valve body 314 moves away from the control port 318, pressure drops within the patient inlet 312, and the airflow proceeds to the chamber 310 and then to ambient environment via the opening 328.

The drive mechanism beam 316 is configured to deflect only a limited extent in response to expected forces on the valve body 314 (i.e., expected airflow pressures at the control port 318 in connection with an adult patient's expiratory phase of breathing), and thus resists overt movement of the valve body 314 away from the control port 318. In addition, as the valve body 314 is further spaced from the control port 318, the force placed upon the valve body 314 by airflow/pressure from the control port 318 inherently decreases due to an increased area of the gap 362. At a point of maximum deflection (FIG. 19A), a spring-like attribute of the drive mechanism beam 316 subsequently forces the valve body 314 back toward the control port 318, such that the valve body 314 again more overtly obstructs airflow through the control port 318. The drive mechanism beam 316 ultimately returns to the near-neutral position of FIG. 19B in which the valve body 314 substantially closes the control port 318, and a back pressure is again established within the patient inlet 312. The attendant force on the valve body 314 then increases, causing the drive mechanism beam 316 to again deflect as described above. This cyclical movement of the interrupter valve assembly 304 continues throughout the expiratory phase, thereby creating a periodically-occurring back pressure within the patient inlet 312. The patient, in turn, experiences an oscillatory PEP treatment, with the patient's exhaled air serving as the sole input force to the driving mechanism beam 316.

Figure 20:
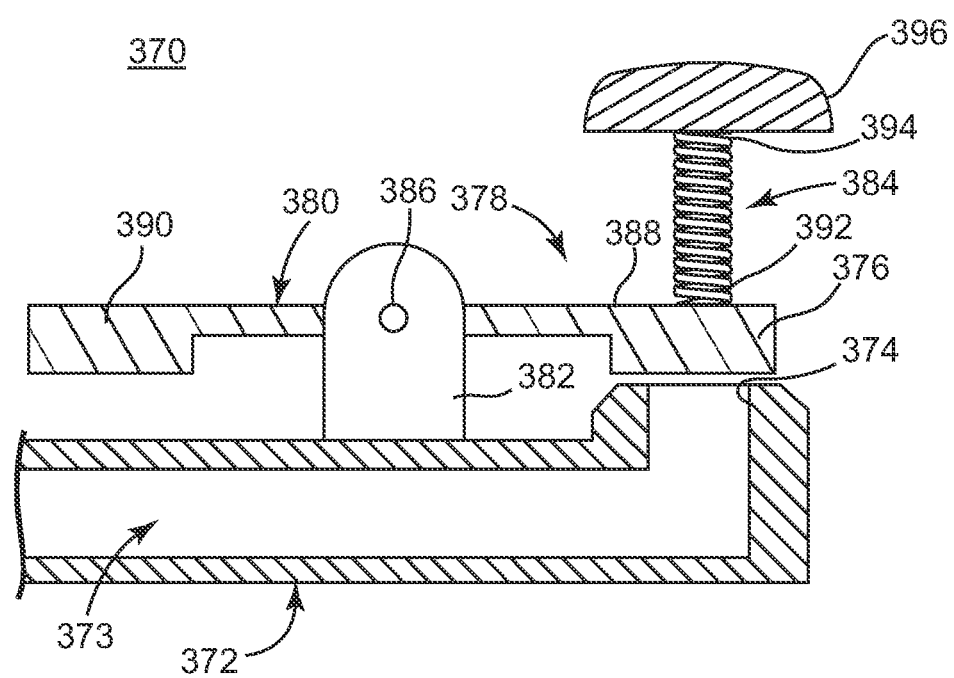
FIG. 20 is a schematic illustration of an interrupter valve assembly useful with the device of FIG. 17.

Although the respiratory therapy device 300 has been described in connection with a cantilever-type resonator interrupter valve assembly 304, in other embodiments, a differing configuration can be employed. For example, FIG. 20 schematically illustrates an alternative embodiment interrupter valve assembly 370 in connection with a tube 372 otherwise forming a patient inlet 373 and a control port 374. As a point of reference, the tube 372 of FIG. 20 is akin to the tube 332 of FIG. 18A. Regardless, the interrupter valve assembly 370 employs a rocker-type arrangement, and includes a valve body 376 and a drive mechanism 378. The valve body 376 is sized in accordance with a size of the control port 374 (e.g., identical, slightly smaller, or slightly larger), and is maintained or driven by the drive mechanism 378. In this regard, the drive mechanism 378 includes an arm 380, a support 382, and a biasing device 384.

The arm 380 maintains the valve body 376 and is pivotally mounted to the support 382 at a pivot point 386. The arm 380 includes a first side 388 at which the valve body 376 is formed or affixed, and an opposite, second side 390. As shown, the second side 390 is configured to provide additional mass to offset a mass of the valve body 376. Regardless, the support 382 pivotally maintains the arm 380 and can be assembled to, or formed as part of, the tube 372.

The biasing device 384 exerts a biasing force onto the valve body 376 opposite the control port 374. In some embodiments, the biasing device 384 is a coil spring secured at a first end 392 to the valve body 376/arm 380 and at an opposite, second end 394 to a support structure 396 (drawn generally in FIG. 20). As a point of reference, in some embodiments, the support structure 396 can be formed by, or provided as part of, the outer housing portion 306 (FIG. 18A).

Regardless of exact construction, the interrupter valve assembly 370 provides a balanced rocker arrangement, with the biasing device 384 serving as a stiffness element. During use, the valve body 376 limits airflow from the patient inlet 373/control port 374, with the distance or gap between the valve body 376 and the control port 374 (and thus the resistance to expiratory airflow) being cyclically dictated by the biasing device 384. Once again, as the valve body 376 approaches the control port 374, a back pressure is created within patient inlet 373 (in conjunction with continued airflow from the patient during the expiratory phase of breathing). With this arrangement, then, an oscillatory PEP therapy can be delivered, with the interrupter valve assembly 370 operating independent of a spatial orientation of the corresponding respiratory therapy device/housing. Though not shown, an additional nebulizer port(s) can be provided with, or formed by, the housing 302 through which aerosolized medication can be delivered to the patient.

Figure 21A:
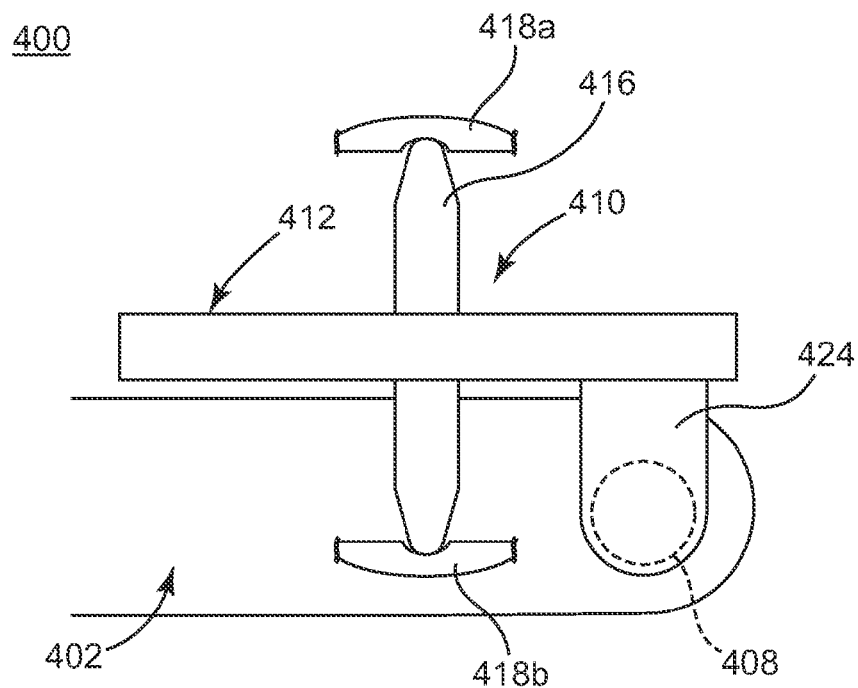
FIGS. 21A and 21B are simplified, schematic illustrations of an alternative interrupter valve assembly useful with the device of FIG. 17.
Figure 21B:
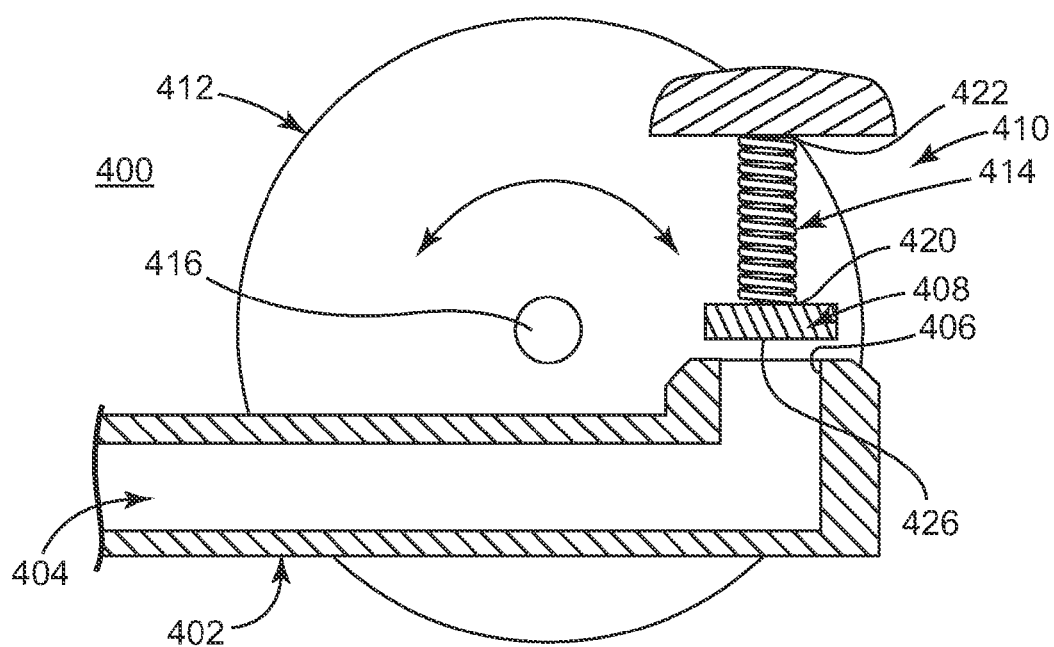

Yet another alternative embodiment interrupter valve assembly 400 is shown schematically in FIGS. 21A and 21B. As best shown in FIG. 21B, the interrupter valve assembly 400 is associated with a tube 402 that is akin to the tube 332

(FIG. 18A) previously described, and otherwise defines a patient inlet 404 and a control port 406.

With the above conventions in mind, the interrupter valve assembly 400 includes the control port 406, a valve body 408, and a drive mechanism 410. Once again, the valve body 408 is sized and shaped in accordance with the size and shape of the control port 406, as previously described (e.g., identical, slightly larger, slightly smaller, etc.). With the embodiment of FIGS. 21A and 21B, the drive mechanism 410 is akin to a proportional spring mass system and includes a fly wheel 412 and a biasing device 414. The fly wheel 412 is rotatably mounted relative to the tube 402, for example by a spindle 416. As shown in FIG. 21A, for example, the spindle 416 can be mounted or held by various surfaces 418a, 418b provided with a housing (not shown) of the corresponding therapy device. Regardless, the fly wheel 412 can freely rotate.

The biasing device 414 defines a first end 420 and a second end 422. The first end 420 is secured to the valve body 408, whereas the second end 422 is secured to the fly wheel 412, for example by a finger 424 as shown in FIG. 21A. In some embodiments, the biasing device 414 is a linear spring, but in other embodiments can take other forms, such as a coiled torsional spring.

Regardless of exact construction, during use the valve body 408 serves to restrict airflow from the patient inlet 404 through the control port 406. In this regard, a level of resistance to airflow (and thus back pressure created within the patient inlet 404 during expiratory phase of a patient's breathing cycle) is a function of a gap 426 (FIG. 21B) between the valve body 408 and the control port 406. The drive mechanism 410, in turn, dictates a size or dimension of this gap. In particular, as exhaled air is directed through the control port 406, the valve body 408 is forced away from the control port 406, with the biasing device 414 providing a resistance to the airflow force placed upon the valve body 408. Further, as the valve body 408 is moved away from the control port 406, the force is translated onto the biasing device 414, and then onto the fly wheel 412. As a result, the fly wheel 412 slightly rotates (e.g., counterclockwise relative to the orientation of FIG. 21B). At a certain point, a spring force of the biasing device 414 overcomes a force of the airflow through the control port 406, such that the biasing device 414 forces the valve body 408 back toward the control port 406. In this regard, the fly wheel 412 serves as a guide for movement of the valve body 408, ensuring that the valve body 408 moves back toward alignment with the control port 406. In this manner then, a periodic back pressure is created within the patient inlet 404, thus effectuating an oscillatory PEP therapy to the patient during the patient's expiratory phase of breathing.

Figure 22:
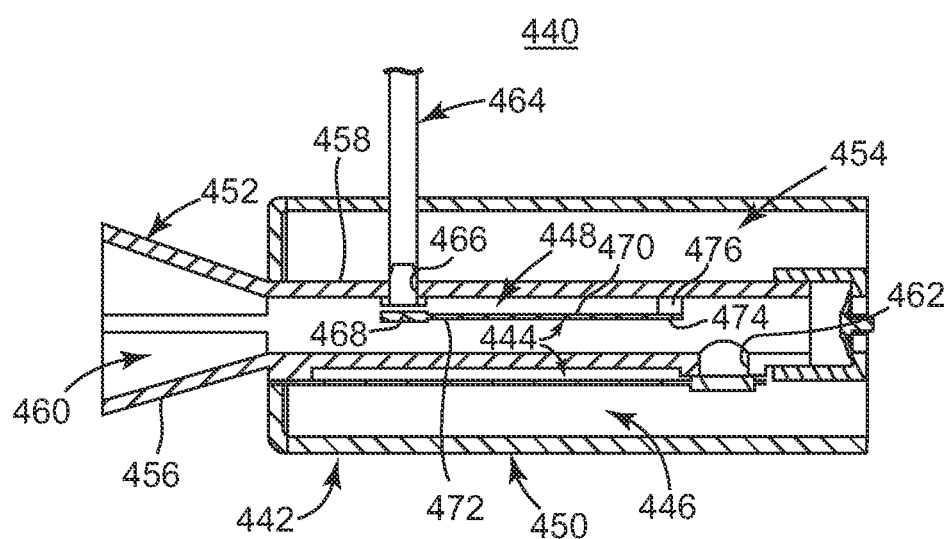
FIG. 22 is a longitudinal, cross-sectional view of another embodiment respiratory therapy device in accordance with principles of the present disclosure.

Although the respiratory therapy device 300 (FIG. 17), along with the various interrupter valve assemblies 370 (FIG. 20), 400 (FIGS. 21A, 21B), has been described in the context of a passive-only device (e.g., providing oscillatory PEP therapy in response to the patient's exhaled breath), in other embodiments, similar design configurations can be employed to provide a respiratory therapy device capable of operating in both a passive mode (e.g., oscillatory PEP) and an active mode (e.g., CHFO). For example, FIG. 22 illustrates another alternative embodiment respiratory therapy device 440 in accordance with aspects of the present invention. The respiratory therapy device 440 is highly similar to the respiratory therapy device 300 (FIG. 17) previously described, and includes a housing 442 and an interrupter valve assembly 444 including a first interrupter valve sub-assembly 446 and a second interrupter valve sub-assembly 448. Once again, the housing 442 includes an outer portion 450 and an inner portion 452 that combine to define a chamber 454. The inner portion 452 includes a mouthpiece 456 and a tube 458 that combine to define a patient inlet 460. Further, the tube 458 forms a first control port 462 fluidly connecting the patient inlet 460 and the chamber 454. In this regard, the first interrupter valve sub-assembly 446 is akin to the interrupter valve assembly 304 (FIG. 17) previously described, and provides oscillatory back pressure within the patient inlet 460 in response to exhaled air. In other words, the first interrupter valve sub-assembly 446 operates as previously described, establishing oscillatory PEP therapy.

In addition to the above, the housing 442 includes a supply inlet 464 extending from the inner housing portion 452 and exteriorly from the outer housing portion 450. The supply inlet 464 is configured for fluid connection to an external source of pressurized fluid (not shown, but akin to the pressurized fluid source 48 of FIG. 1), and is fluidly connected to a second control port 466 formed by, or connected to, the tube 458.

With the above in mind, the second interrupter valve sub-assembly 448 is akin to the first interrupter valve sub-assembly 446 and includes the second control port 466, a valve body 468 and a drive mechanism 470. The valve body 468 has a size and shape commensurate with a size and shape of the second control port 466, such that the valve body 468 can obstruct fluid flow through the second control port 466. Though not shown, various relief port arrangement(s) and related valve structure(s) can further be included in connection with the second interrupter valve sub-assembly 448 to ensure adequate pressure is reached to produce desired pressure pulse/volume, and/or entrainment of ambient air.

The drive mechanism 470 is, in some embodiments, an elongated beam having a first end 472 and a second end 474. The first end 472 maintains the valve body 468, whereas the second end 474 is configured for mounting to an interior shoulder 476 that in some embodiments is formed or provided by the tube 458.

Upon final assembly, then, the valve body 468/drive mechanism 470 are interiorly positioned within the tube 458, with the valve body 468 being aligned with the second control port 466. During use, positive airflow is established within the patient inlet 460, with the fluid flow being directed to the second control port 466. The second interrupter valve sub-assembly 448 operates to periodically interrupt fluid flow through the second control port 466 and into the patient inlet 460. In particular, and as previously described, the drive mechanism beam 470 moves the valve body 468 in a cyclical fashion relative to the second control port 466, thereby creating a varying obstruction to fluid flow into the patient inlet 460. Thus, when operating in an active mode (i.e., when the therapy device 440 is connected to the source of pressurized fluid 48 of FIG. 1), the respiratory therapy device 440 provides CHFO treatment to the patient during the patient's breathing cycle (including the inspiratory phase). Conversely, the therapy device 440 can be disconnected from the source of pressurized fluid (and the supply inlet 464 fluidly closed) and operate in the passive mode to provide oscillatory PEP therapy. Though not shown, the therapy device 440 can incorporate additional features that facilitate use of the therapy device 440 to deliver aerosolized medication, CPAP therapy (constant or variable), etc., as described above with respect to the device 60 (FIG. 2). Even further, the therapy device 440 can be modified to serve as an "active-only" device, for example by eliminating the first interrupter valve sub-assembly 446.

Figure 23A:
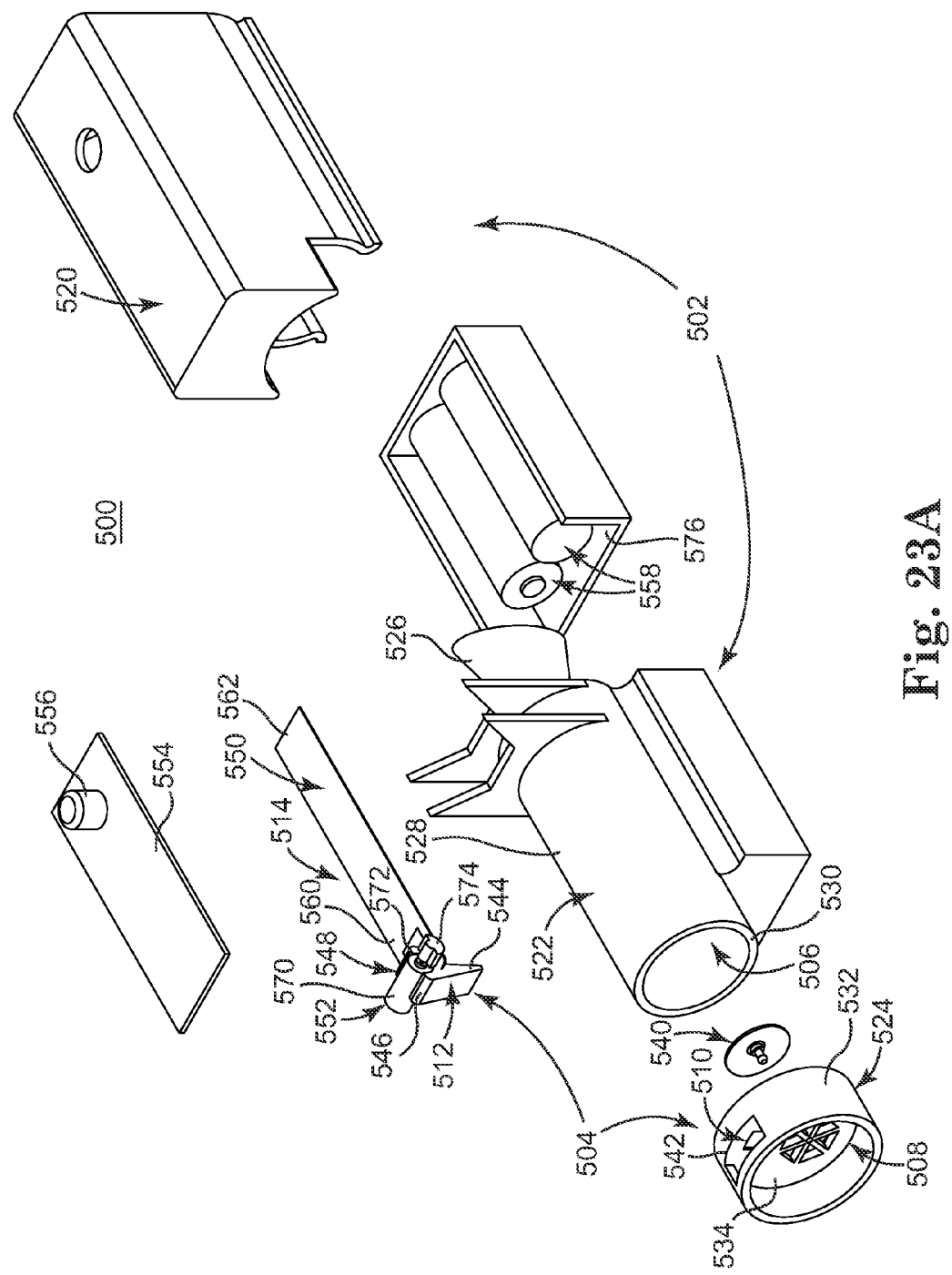
FIG. 23A is an exploded, perspective view of another embodiment respiratory therapy device in accordance with principles of the present disclosure.

Yet another alternative embodiment respiratory therapy device 500 is shown in FIGS. 23A and 23B. The respiratory therapy device 500 includes a housing 502 (referenced generally) and an interrupter valve assembly 504 (referenced generally). Details on the various components are provided below. In general terms, however, the housing 502 maintains the interrupter valve assembly 504, and forms a patient inlet 506 fluidly connected to a chamber 508 via a control port 510. The interrupter valve assembly 504 includes a valve body 512 and a drive mechanism 514 (referenced generally). During use, the drive mechanism 514 moves the valve body 512 relative to the control port 510 such that the valve body 512 variably restricts airflow through the control port 510. In this way, a pulsed back pressure is created within the patient inlet 506, thereby delivering an oscillatory PEP therapy.

The housing 502 includes an outer portion 520, an inner portion 522, and an orifice body 524. The outer portion 520 provides an exterior frame contoured for convenient handling of the therapy device 500 by a user, and maintains the various components thereof.

The inner housing portion 522 includes a mouthpiece 526 and a tube 528. The mouthpiece 526 is sized and shaped for convenient placement within a patient's mouth (or assembly to a separate component adapted for placement in a patient's mouth, such as a nebulizer connector piece), and can be integrally formed with the tube 528. Regardless, the mouthpiece 526 and the tube 528 combine to define the patient inlet 506 through which airflow to and from the patient directly occurs. In this regard, the tube 528 extends from the mouthpiece 526 to a trailing side 530.

Figure 24:
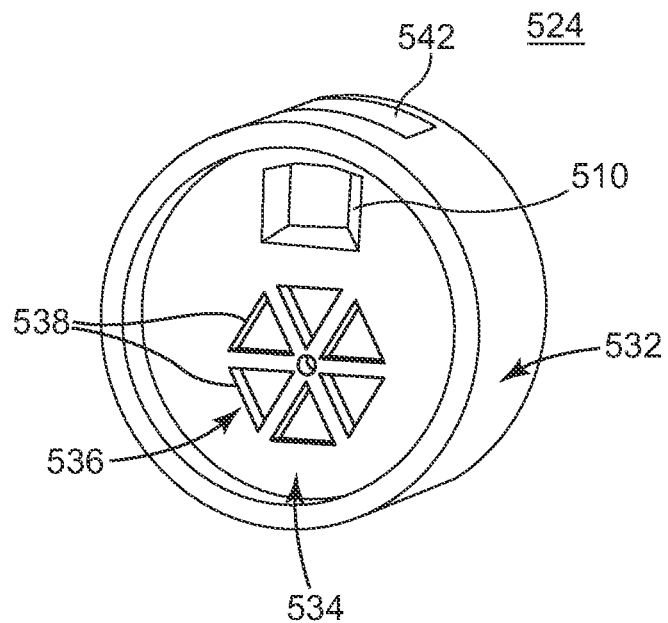
FIG. 24 is an enlarged, perspective view of an orifice assembly portion of the device of FIG. 23A.

With additional reference to FIG. 24, the orifice body 524 is assembled to, or formed as part of the tube 528 at the trailing side 530 thereof. The orifice body 524 includes a rim 532 and a wall 534. As best shown in FIG. 24, the control port 510 is formed in the wall 534. In addition, the wall 534 forms a relief port arrangement 536, consisting of one or more apertures 538. The relief port arrangement 536 maintains a valve structure 540 that otherwise allows airflow through the apertures 538 in only a single direction. Regardless, the rim 532 forms a slot 542 that is adjacent the control port 510. With this configuration, a body inserted through the slot 542 can selectively obstruct all or a portion of the control port 510.

Returning to FIGS. 23A and 23B, the valve body 512 is sized for slidable insertion within the slot 542 and includes a leading segment 544 and a trailing segment 546. The leading segment 544 is sized for slidable placement within the slot 542, and in some embodiments has a tapered shape. Regardless, the trailing segment 546 is configured for attachment to corresponding components of the drive mechanism 514 as described below.

With the embodiment of FIGS. 23A and 23B, the drive mechanism 514 is configured to operate as an EMF resonator and includes a resonator system 548 (comprised of a beam 550 and a micromotor assembly 552), control circuitry 554, an actuator 556, and a power source 558. In general terms, the power source 558 powers the micromotor assembly 552. In response to a user prompt at the actuator 556, the circuitry 554 activates the micromotor 552 that in turn causes the beam 550 to resonate, in some embodiments at a natural frequency of the beam. Regardless, the beam 550 vibrates, causing the attached valve body 512 to move relative to the control port 510.

The beam 550 is relatively thin and is formed from a stiff material. In some embodiments, the beam 550 is formed of steel that otherwise exhibits low damping characteristics; alternatively, other materials such as plastic, ceramic, etc., may also be employed. For example, where the beam 550 is formed of steel, it can have a thickness on the order of 0.01 inch. Where differing materials are employed, a nominal thickness of the beam 550 may be increased or decreased.

As described in greater detail below, during use, the beam 550 is subjected to a vibrational force, causing a leading portion 560 thereof to resonate (whereas a trailing portion 562 is held stationary). With this in mind, in some embodiments, the beam 550 is constructed (e.g., in terms of material and dimensions) so as to not only fit within a desired footprint of the housing outer portion 520, but also to exhibit a natural frequency above a desired level such that when the micromotor assembly 552 and the valve body 512 are attached to the leading section 560, the resultant natural frequency of the resonator system 548 will approximate a desired natural frequency. For example, in some embodiments, a desired natural frequency of the resonator system 548 (at the leading section 560 of the beam 550) is approximately 15 Hz. In the absence of a mass of the micromotor assembly 552 and the valve body 512, then, the beam 550 exhibits, in some embodiments, a natural frequency well above 15 Hz (for example, on the order of 40-80 Hz). With a mass of the valve body 512 and the micromotor assembly 552 in mind, then, additional mass can be added to the beam 550 to "fine tune" the overall natural frequency of the resonator system 548 to approximate 15 Hz. Of course, in other embodiments, other frequencies exhibited by the beam 550 alone and/or in combination with the micromotor assembly 552 and the valve body 512 are also acceptable.

As best shown in FIG. 23A, the micromotor assembly 552 includes a variable speed micromotor 570 that rotates an output shaft 572. An unbalanced mass 574 is mounted to the output shaft 572. With this configuration, then, operation of the micromotor assembly 552 generates a vibrational force load at the running frequency. The micromotor 570 can assume a wide variety of forms, and in some embodiments micromotor is a brushed, direct current (DC) motor, adapted to rotate the output shaft 572 at a rotational speed proportional to the input voltage supplied to the micromotor 570. For example the micromotor 570 can be akin to a micromotor used in cell phone application for generating a vibrational force, for example a micromotor manufactured by Maduchi Motor Co. under the trade designation Model RF-J2WA. Regardless, the micromotor 570 is electronically connected to the circuitry 554 that in turn regulates voltage supply to the micromotor 570 from the power source 558.

Figure 25:
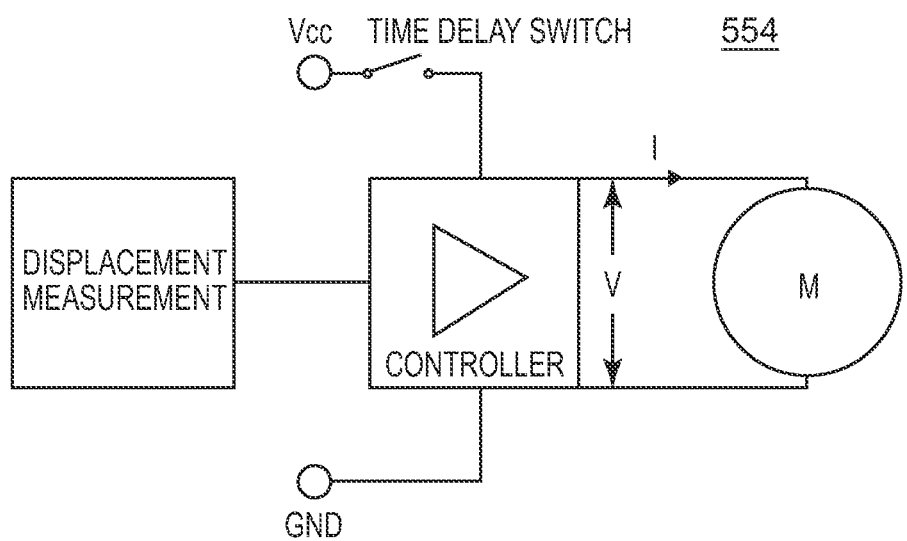
FIG. 25 is a schematic, electrical diagram of control circuitry useful with the device of FIG. 23A.

The control circuitry 554 is, in some embodiments, a control chip or circuit board adapted to regulate the voltage applied to the micromotor 570 and limit current to the micromotor 570 based on displacement and frequency of the valve body 512/beam 550. In this regard, the control circuitry 554 is adapted to monitor the beam 550, effectively viewing the beam 550 as a capacitor. With this approach, a measurement of both displacement and frequency can be made. More particularly, the frequency measurement can be used to control the output voltage to the micromotor 570 and maintain a desired speed, while the displacement measurement can be used to shift the speed of the micromotor 570 to avoid hitting "hard" stops on the beam 550. As a point of reference, if the beam 550 hits a "hard" stop, the beam 550 will stop oscillating and will require time to regain the correct valve opening and frequency. One exemplary schematic configuration of the control circuitry 554 is provided in FIG. 25. It will be understood, however, that this is but one acceptable configuration.

Returning to FIGS. 23A and 23B, the actuator 556 is configured to prompt the control circuitry 554 to initiate or stop delivery of power to the micromotor 570. In this regard, the actuator 556 can assume a variety of forms, and in some embodiments is a button or similar body projecting from the housing outer portion 520. Alternatively, the actuator 556 can assume a variety of other forms, for example a membrane-based sensor, wireless actuator, etc.

Finally, the power source 558 provides appropriate power to the micromotor 570 and the control circuitry 554. In some embodiments, the power source 558 is carried within a compartment 576 of the housing 502, and can assume any appropriate form (e.g., one or more batteries).

Figure 26A:
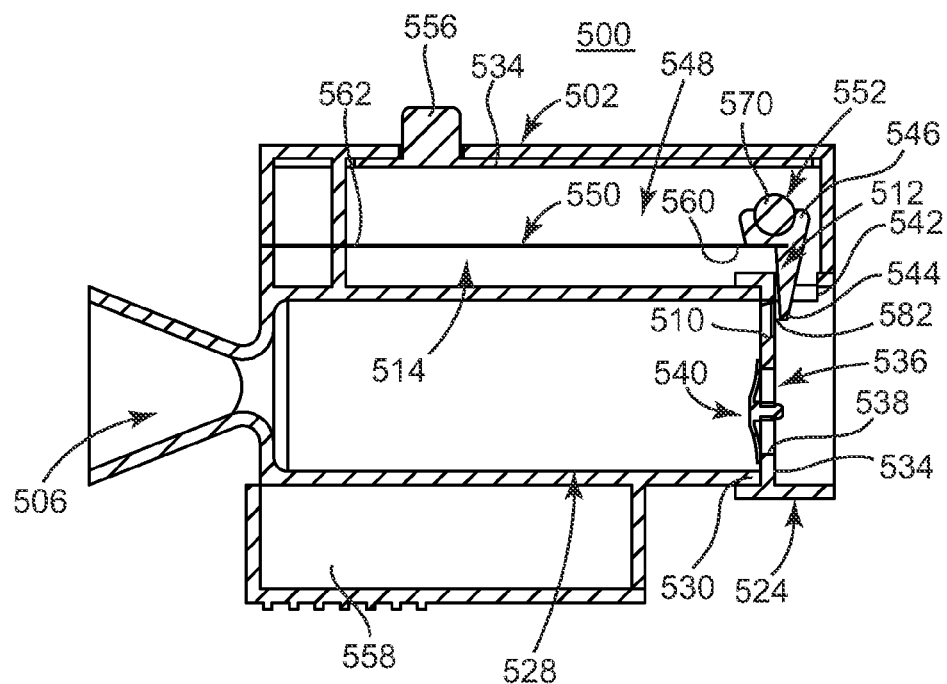
FIGS. 26A and 26B illustrate the device of FIG. 23A upon final assembly.
Figure 26B:
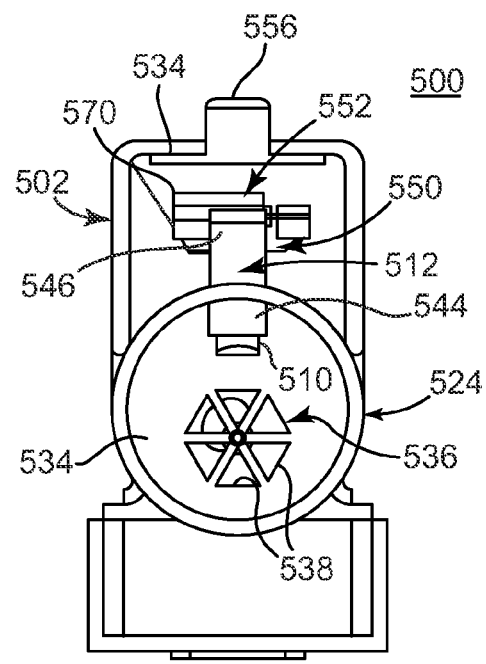

The respiratory therapy device 500 is shown in assembled forms in FIGS. 26A and 26B. In particular, the valve body 512 is assembled to the leading section 560 of the beam 550 such that the leading segment 544 extends away from the beam 550. The micromotor assembly 552 is mounted to the trailing segment 546 of the valve body 512 as best shown in FIG. 26A. In this regard, while the trailing segment 546 is adapted to receive the micromotor assembly 552, in other embodiments, the micromotor assembly 552 can be mounted directly to the beam 550.

The orifice body 524 is coupled to the trailing side 530 of the tube 528 such that the wall 534 extends across the tube 528. As shown in FIG. 26A, the one-way valve structure 540 is assembled to the relief port arrangement 536 so as to control fluid flow through the apertures 538.

The beam 550 is then assembled to the housing 502 such that the trailing section 562 is affixed relative to the housing 502, and the valve body 512 slidably extends within the slot 542 of the orifice body 524. As best shown in FIG. 26B, in a natural state of the beam 550, the leading segment 544 of the valve body 512 partially obstructs the control port 510. Further, and as best shown in FIG. 26A, a slight gap 582 (referenced generally) is established between the valve body 512 and the wall 534 of the orifice body 524 (and thus the control port 510).

The power source 558 is assembled to the housing 502 as shown, and electrically connected to the control circuitry 554 and the micromotor 570, for example via wiring (not shown). The control circuitry 554, as well as the actuator 556, are similarly assembled to the housing 502.

During use, the micromotor assembly 552 is operated to resonate the beam 550, and thus the valve body 512. As indicated above, in some embodiments, the resonator system 548 (i.e., the beam 550, micromotor 552, and the valve body 512) is constructed to exhibit a natural resonation frequency approximating a desired frequency of movement of the valve body 512 relative to the control port 510. By exciting the resonator system 548 (and thus the beam 550) at the selected natural frequency, the input force and function can be smaller than the force required to deflect the beam 550 alone, thus resulting in reduced power requirements. Thus, as the motor assembly 552 vibrates, the beam 550 resonates, causing the valve body 512 to move back and forth (e.g., up and down relative to the orientation of FIG. 26B) relative to the control port 510. As such, with resonation of the beam 550, the valve body 512 selectively "opens" and obstructs the control port 510 in an oscillating fashion.

Figure 27A:
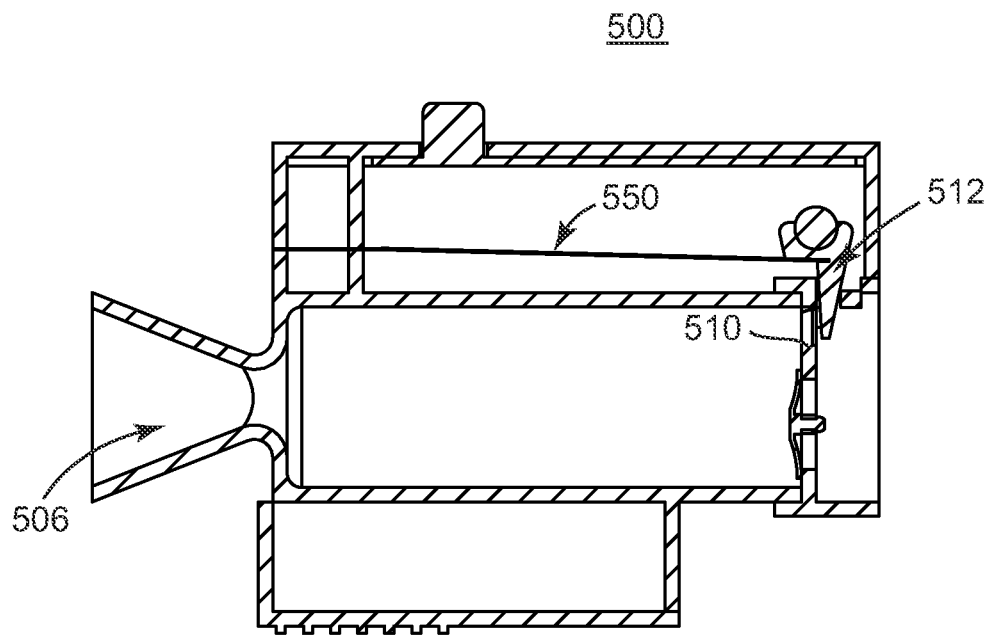
FIGS. 27A and 27B illustrate use of the device of FIG. 23A.
Figure 27B:
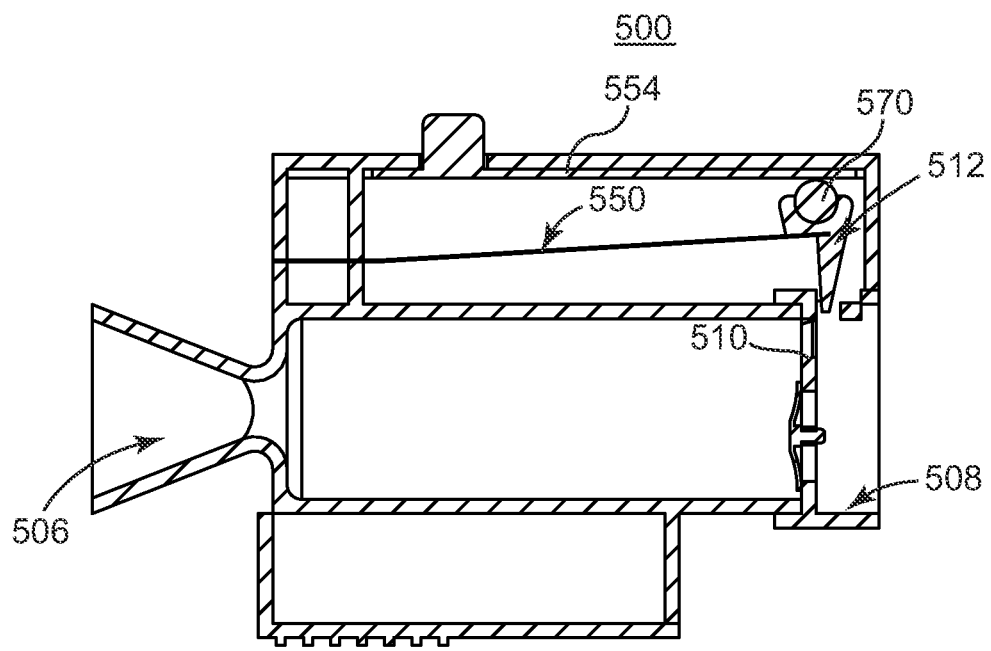

Regardless of whether the micromotor 570 is powered, during the inspiratory phase of a patient's breathing cycle, ambient air readily enters the patient inlet 506 via the relief port arrangement 536. During the expiratory phase (and with appropriate activation of the drive mechanism 514 via the actuator 556), the drive mechanism 514 causes the valve body 512 to open and close the control port 510 in an oscillating fashion. For example, and with reference to FIG. 27A, as the beam 550 resonates downwardly (relative to the orientation of FIG. 27A), the valve body 512 essentially closes the control port 510 such that exhaled airflow within the patient inlet 506 cannot flow through the control port 510. As a result, a back pressure is created within the patient inlet 506. Conversely, and as shown in FIG. 27B, as the beam 550 resonates upwardly (relative to the orientation of FIG. 27B), the valve body 512 is radially displaced from the control port 510, such that airflow within the patient inlet 506 easily passes through the control port 510 and into the chamber 508 (and thus is exhausted to ambient). In this regard, the control circuitry 554 operates to regulate power supply to the motor assembly 570 so as to consistently resonate the beam 550 at a desired frequency (e.g., 15 Hz). Regardless, the periodic back pressure created within (and release from) the patient inlet 506 during the expiratory phase of the patient's breathing cycle effectuates an oscillatory PEP treatment for the patient. In other embodiments, one or more nebulizer port(s) (not shown) can be provided with, or formed by, the housing 502 to facilitate delivery of aerosolized medication to the patient. Similarly, a nebulizer connection piece (not shown) can be fluidly connected in-line to the mouthpiece 526.

Figure 28:
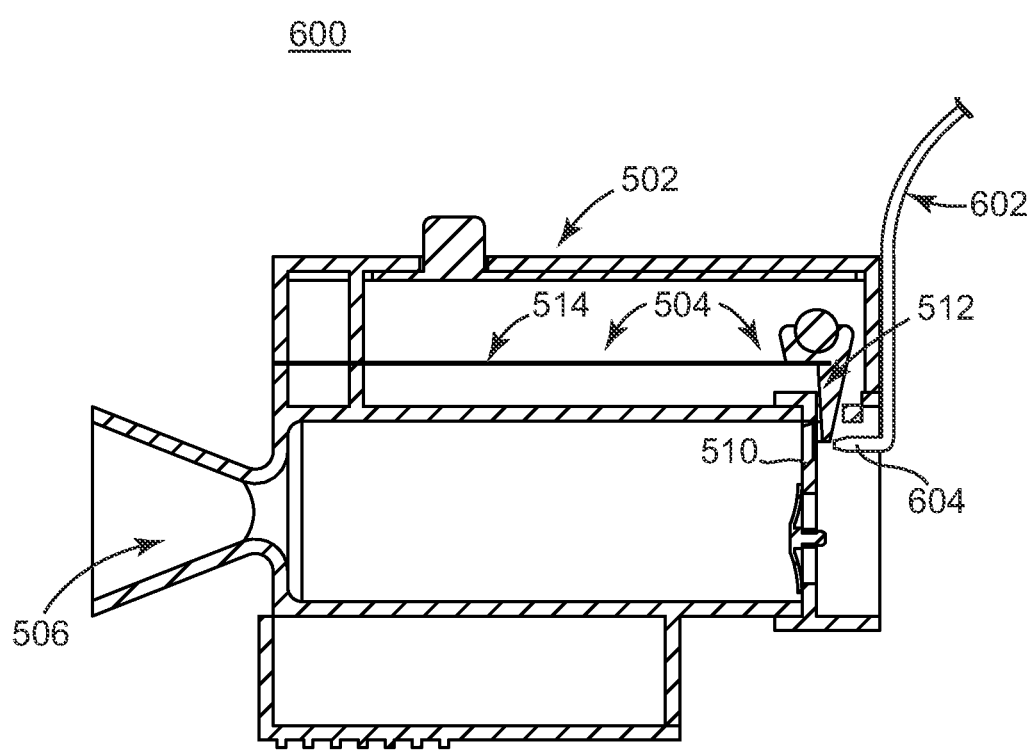
FIG. 28 is a longitudinal, cross-sectional view of another embodiment respiratory therapy device in accordance with principles of the present disclosure.

Although the respiratory therapy device 500 has been described as operating or providing only a passive mode (e.g., oscillatory PEP), in other embodiments, similar design characteristics can be employed in providing a therapy device capable of operating in both a passive mode as well as an active mode (e.g., CHFO). For example, FIG. 28 illustrates another embodiment respiratory therapy device 600 that is highly similar to the therapy device 500 (FIG. 22A) previously described. More particularly, the respiratory therapy device 600 includes the housing 502 and the interrupter valve assembly 504 components as previously described, as well as a supply inlet 602. The supply inlet 602 is adapted for fluid connection to an external source of pressurized fluid (not shown, but akin to the pressurized fluid source 48 of FIG. 1), and terminates at a nozzle end 604. As shown, the nozzle end 604 directs fluid flow from the supply inlet 602 toward the control port 510. Further, a position of the nozzle end 604 relative to an exterior of the housing 502 allows for entrainment of ambient air into the fluid flow from the nozzle end 604. Additional valving (not shown) can optionally be provided to prevent occurrences of stacked breaths.

In a passive mode of operation (i.e., the supply inlet 602 is disconnected from the pressurized fluid source), the therapy device 600 operates as previously described (e.g., during the expiratory phase of the patient's breathing cycle, the drive mechanism 514 resonates the valve body 512 relative to the control port 510 so as to establish a periodic back pressure within the patient inlet 506 in providing oscillatory PEP therapy). In an active mode of operation, positive fluid flow is forced through the supply inlet 602 and directed by the nozzle end 604 toward the control port 510. In connection with this forced supply of airflow, the drive mechanism 514 again causes the valve body 512 to resonate relative to the control port 510, thus cyclically interrupting fluid flow from the nozzle end 604 through the control port 510, and thus into the patient inlet 506. Thus, in the active mode of operation, the respiratory therapy device 600 operates to provide CHFO treatment to the patient during an entirety of the breathing cycle (including at least the inspiratory phase of breathing). Though not shown, the therapy device 600 can incorporate additional features that facilitate use thereof to delivery aerosolized medication, CPAP therapy, etc., as described above with respect to the device 60 (FIG. 2). Even further, the therapy device 600 can be modified to serve as an "active-only" device, for example by providing an exhaust valve arrangement between the mouthpiece 506 and the control port 510.

The respiratory therapy device of the present invention provides a marked improvement over previous designs. In some embodiments, a standalone respiratory therapy device is provided, capable of operating in a passive mode and an active mode. In the passive mode, the therapy device effectuates an oscillatory PEP treatment to the patient, and with many embodiments does so solely in response to the patient's exhaled breath. In the active mode of operation, an external source of pressurized fluid is connected to the device with the device independently affecting fluid flow from the external source to provide CHFO treatment. Unlike existing configurations, embodiments of the present disclosure providing an active mode of operation can be connected to virtually any pressurized fluid source (e.g., regulated or non-regulated wall source, home compressor, oxygen tank, a mechanical/pneumatic flow interrupter or "driver," standalone ventilator system, etc.). In this regard, when connected to an existing flow interrupter/driver that otherwise generates pressurized fluid in pulsed form, the driver can provide the ability to "tailor" the actual therapy delivered to a particular patient. In yet other embodiments, the respiratory therapy device provides passive therapy (e.g., oscillatory PEP) in a manner not previously considered. In yet other embodiments, an improved "active-only" therapy device is provided. Further, with any of the embodiments, additional therapies can be provided, such as CPAP and/or nebulizer treatments.

Although the present invention has been described with respect to preferred embodiments, workers skilled in the art will recognize that changes can be made in form and detail without departing from the spirit and scope of the present invention.

What is claimed is:

1. A device for providing respiratory therapy to a patient during at least a portion of a patient breathing cycle including an inspiratory phase and an expiratory phase, the device comprising:
    a housing including a patient inlet, an exhaust outlet, a first chamber fluidly disposed between the patient inlet and the exhaust outlet, a second chamber adjacent the first chamber, a first pressurized fluid supply inlet fluidly coupled to the first chamber and a second pressurized fluid supply inlet fluidly coupled to the second chamber; and
    an interrupter valve assembly associated with the housing and disposed within the first chamber, the interrupter valve assembly including a control port fluidly connecting the patient inlet and the first chamber, and a valve body adapted to selectively obstruct fluid flow through the control port, wherein the interrupter valve assembly further includes a drive shaft carrying the valve body such that with movement of the drive shaft, the valve body selectively covers the control port, and a drive mechanism for moving the drive shaft; and
    wherein the device is adapted such that fluid flow from the second pressurized fluid supply inlet to the second chamber drives the drive mechanism.

2. The device of claim 1, wherein the interrupter valve assembly includes a plurality of control ports, and the valve body is configured to selectively obstruct respective ones of the control ports.

3. The device of claim 1, wherein the drive mechanism includes first and second lobe bodies.

4. The device of claim 3, wherein the first and second chambers are fluidly connected by an aperture such that fluid flow from the first chamber to the second chamber acts upon the lobe bodies to cause rotation thereof.

5. The device of claim 4, wherein the second chamber forms an outlet opening fluidly connected to the exhaust outlet.

6. The device of claim 4, wherein the housing further forms a relief port arrangement in the first chamber apart from the control port, the device further including a valve structure controlling fluid flow through the relief port arrangement such that when a fluid pressure within the first chamber exceeds a predetermined level, the valve structure fluidly opens the relief port arrangement.

7. The device of claim 6, wherein the housing further forms an exhaust chamber defining the exhaust outlet and fluidly connected to the first chamber via the relief arrangement.

8. The device of claim 7, wherein the exhaust chamber is fluidly connected to the second chamber via an outlet opening.

9. The device of claim 1, wherein the device further includes a nozzle having an inlet side fluidly open to the first pressurized fluid inlet and an outlet side fluidly open to the control port, and further wherein the valve body is movable between the nozzle outlet side and the control port to selectively obstruct fluid flow from the nozzle outlet side to the control port.

10. The device of claim 1, further comprising:
    a plate disposed between the first and second chambers, the plate forming a passage fluidly connecting the first and second chambers; and
    control means associated with the passage for selectively opening and closing the passage.

11. The device of claim 1, wherein the device is configured such that a level of the continuous high frequency oscillation effect is independent of the breathing effort of the patient.

12. The device of claim 1, wherein the housing further forms an inhalation relief port arrangement and the device further includes a one-way valve structure assembled to the inhalation relief port arrangement for permitting flow of ambient air into the patient inlet during the inspiratory phase.

13. The device of claim 1, wherein the interrupter valve assembly is configured to be held in an open position in which the control port is open such that the device is operable in a continuous mode in which positive fluid flow to the pressurized fluid supply inlet occurs to create a continuous positive airway pressure effect.

* * * * *